(12) United States Patent
Takeya et al.

(10) Patent No.: US 9,537,110 B2
(45) Date of Patent: Jan. 3, 2017

(54) CHALCOGEN-CONTAINING ORGANIC COMPOUND AND USE THEREOF

(71) Applicant: JNC CORPORATION, Tokyo (JP)

(72) Inventors: Junichi Takeya, Osaka (JP); Toshihiro Okamoto, Osaka (JP); Tauto Nakanishi, Chiba (JP)

(73) Assignee: JNC CORPORATION, Tokyo (JP)

( * ) Notice: Subject to any disclaimer, the term of this patent is extended or adjusted under 35 U.S.C. 154(b) by 34 days.

(21) Appl. No.: 14/378,684

(22) PCT Filed: Feb. 20, 2013

(86) PCT No.: PCT/JP2013/054223
§ 371 (c)(1),
(2) Date: Aug. 14, 2014

(87) PCT Pub. No.: WO2013/125599
PCT Pub. Date: Aug. 29, 2013

(65) Prior Publication Data
US 2015/0014673 A1    Jan. 15, 2015

(30) Foreign Application Priority Data
Feb. 22, 2012 (JP) ................................ 2012-036201

(51) Int. Cl.
| | | |
|---|---|---|
| *C07D 333/50* | (2006.01) | |
| *C07D 345/00* | (2006.01) | |
| *C07D 409/14* | (2006.01) | |
| *C07D 417/14* | (2006.01) | |
| *C07D 307/77* | (2006.01) | |

(Continued)

(52) U.S. Cl.
CPC ......... *H01L 51/0073* (2013.01); *C07D 307/77* (2013.01); *C07D 333/50* (2013.01); *C07D 345/00* (2013.01); *C07D 409/14* (2013.01); *C07D 417/14* (2013.01); *H01L 51/0068* (2013.01); *H01L 51/0069* (2013.01);
(Continued)

(58) Field of Classification Search
CPC ............................ C07D 333/50; C07D 409/14
See application file for complete search history.

(56) References Cited

U.S. PATENT DOCUMENTS 7,834,198 B2   11/2010  Takimiya et al.
7,989,644 B2   8/2011   Tanabe et al.
(Continued)

FOREIGN PATENT DOCUMENTS

JP   2007-197400   *  8/2007
JP   2007-217340      8/2007
(Continued)

OTHER PUBLICATIONS

Buu-Hoi, Croatica Chimica Acta, Orientation in Friedel-Crafts Acetylation of Neroline and Its 6-Alkyl Homologues, 1957, 29 pp. 291-295.*

(Continued)

*Primary Examiner* — Paul A Zucker
(74) *Attorney, Agent, or Firm* — Wenderoth, Lind & Ponack, L.L.P.

(57) ABSTRACT

An organic compound represented by formula (1) or formula (2) that is easy to synthesize, and has excellent chemical stability, semiconductor characteristics (high carrier mobility) and high solubility in a solvent.

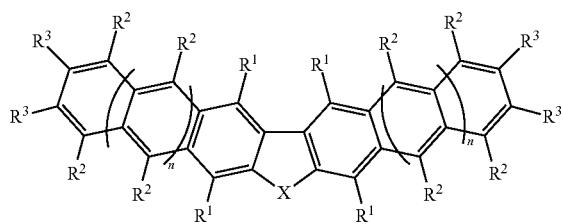

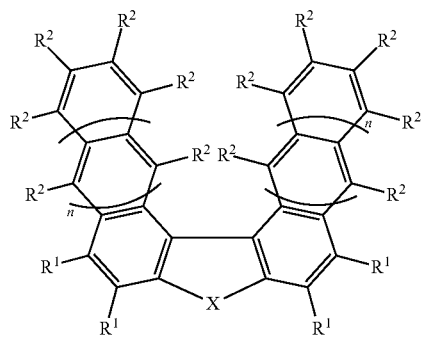

in formula (1), X is oxygen, sulfur or selenium; n is 0 or 1; $R^1$ to $R^3$ are hydrogen, fluorine, alkyl having 1 to 20 carbons, aryl, pyridyl, furyl, thienyl, thiazolyl or the like. However, except for a case where X is selenium, a case where all of $R^1$ to $R^3$ are simultaneously hydrogen is excluded, and a case where X is sulfur and all of $R^1$ are simultaneously butyl is also excluded. In formula (2), X is oxygen, sulfur or selenium; n is 0 or 1; $R^1$ to $R^2$ are hydrogen, alkyl having 1 to 20 carbons, aryl, pyridyl, furyl, thienyl, thiazolyl or the like; however, a case where all of $R^1$ to $R^2$ are simultaneously hydrogen is excluded.

8 Claims, 32 Drawing Sheets

(51) Int. Cl.
  *H01L 51/00* (2006.01)
  *H01L 51/05* (2006.01)
(52) U.S. Cl.
  CPC ...... *H01L 51/0074* (2013.01); *H01L 51/0512* (2013.01); *H01L 51/0558* (2013.01)

(56) References Cited

U.S. PATENT DOCUMENTS

| | | | |
|---|---|---|---|
| 8,110,714 | B2 | 2/2012 | Nagata et al. |
| 8,232,546 | B2 | 7/2012 | Takimiya et al. |
| 2008/0061287 | A1 | 3/2008 | Nagata et al. |
| 2009/0001357 | A1 | 1/2009 | Takimiya et al. |
| 2009/0131673 | A1 | 5/2009 | Tanabe et al. |
| 2009/0261300 | A1 | 10/2009 | Watanabe |
| 2010/0065826 | A1 | 3/2010 | Takimiya et al. |
| 2010/0072887 | A1 | 3/2010 | Kwong et al. |
| 2012/0273768 | A1 | 11/2012 | Ikeda et al. |

FOREIGN PATENT DOCUMENTS

| | | |
|---|---|---|
| JP | 2008-81494 | 4/2008 |
| JP | 2008-545729 | 12/2008 |
| JP | 2009-215425 | 9/2009 |
| JP | 2010-53094 | 3/2010 |
| JP | 2011-178985 | 9/2011 |
| JP | 2012-503889 | 2/2012 |
| JP | 2014-133713 | 7/2014 |
| KR | 2012/0104067 | 9/2012 |
| WO | 2005/080304 | 9/2005 |
| WO | 2006/077888 | 7/2006 |
| WO | 2008-050726 | 5/2008 |
| WO | 2008/050726 | 5/2008 |
| WO | 2010/036765 | 4/2010 |
| WO | 2011/055529 | 5/2011 |

OTHER PUBLICATIONS

Buu-Hoi et al, Croatica Chimica Acta, Orientation in Friedel-Crafts Acetylation of Neroline and Its 6-Alkyl Homologues, 1957, 29 pp. 291-295.*

Royer, Annali de Chimica Applicata, Contribution A La Chimie Du Methyl-6 Naphtol-2, 1946, 1, pp. 395-445.*

Extended European Search Report issued Oct. 19, 2015 in corresponding European patent application No. 13 75 1708.

Veaceslav Coropceanu et al., "Vibronic Coupling in Organic Semiconductors: The Case of Fused Polycyclic Benzene-Thiophene Structures", Chemistry-A European Journal, vol. 12, No. 7, Feb. 20, 2006, pp. 2073-2080.

Marvin L. Tedjamulia et al., "The synthesis of dinaphthothiophenes", Journal of Heterocyclic Chemistry, vol. 20, No. 5, Sep. 1, 1983, pp. 1143-1148.

International Search Report issued Apr. 16, 2013 in International (PCT) Application No. PCT/JP2013/054223.

N. P. Buu-Hoi et al., "Orientation in Friedel-Crafts Acetylation of Neroline and its 6-Alkyl Homologues", Croatica Chemica Acta, vol. 29, pp. 291-295, 1957.

B. J. Morrison et al., "Condensations of Thiophene with Ketones", Journal of the Chemical Society, Perkin Trans., vol. 1, pp. 1944-1947, 2002.

R. Royer, "Contribution A La Chimie Du Methyl-6 Naphtol-2", Annali de Chimica Applicata, vol. 1, pp. 395-445, 1946.

I. Skoric et al., "Photochemical Dimerization of Styrylnaphthofurans-II", Heterocycles, vol. 53, No. 1, pp. 55-68, 2000.

J. E. Anthony et al., "Functionalized Pentacene: Electronic Properties from Control of Solid-State Order", J. Am. Chem. Soc. vol. 123, pp. 9482-9483, 2001.

R. Wilputte et al., "(Poly)Benzo-9-Thiafluorenes et Anhydride Thianaphtene-4,5-Dicarboxylique", Bull. Soc. Chim Belg., vol. 65, pp. 874-898, 1956.

R. F. Curtis et al., "The Synthesis of 2 : 3-6 : 7-Dibenzodiphenylene", Journal of the Chemical Society, pp. 1670-1676, 1959.

H. J. Barber et al., "Cyclic Disulphides Derived from Diphenyl", Journal of the Chemical Society, pp. 1141-1149, 1928.

W. Knecht et al., "α- und β-Dinaphtylenoxyd", Chemische Berichte, vol. 13, pp. 1724-1726, 1880.

R. K. De et al., "Sulfur Containing Stable Unsubstituted Heptacene Analogs", Organic Letters, vol. 14, No. 1, pp. 78-81, 2012.

Y. Ni et al., "Zirconium-Mediated Coupling Reaction for Synthesis of Substituted Thiophene-Fused Acenes", Organic Letters, vol. 11, No. 16, pp. 3702-3705, 2009.

* cited by examiner

Figure 4
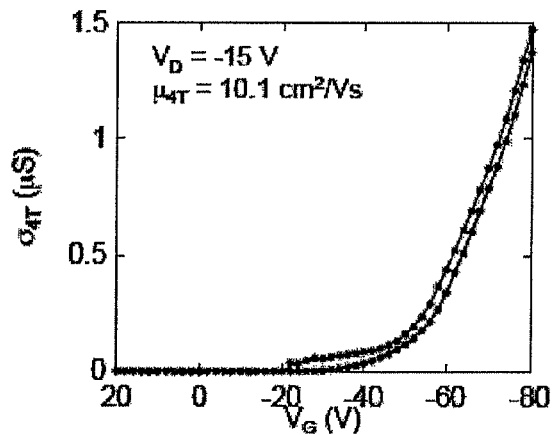
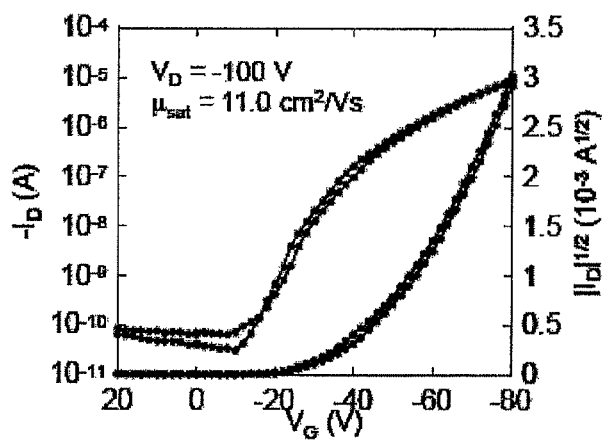
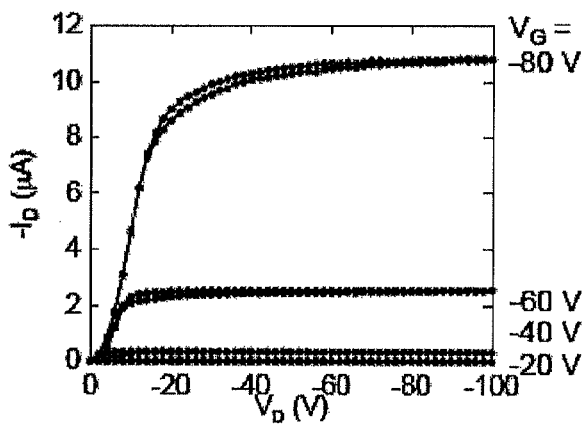

89%

CHALCOGEN-CONTAINING ORGANIC COMPOUND AND USE THEREOF

TECHNICAL FIELD

The present invention relates to a novel chalcogen-containing organic compound and a use thereof. More specifically, the invention relates to a novel chalcogen-containing organic compound and a method for manufacturing the same, an organic semiconductor material composed of the organic compound, an organic semiconductor film including the organic semiconductor material and an organic field effect transistor (FET) having the organic semiconductor film.

BACKGROUND ART

In recent years, organic compounds having semiconductor characteristics have attracted attention. Among the organic compounds, a polyacene compound such as pentacene and tetracene has been known as an organic semiconductor material due to high carrier mobility thereof for many years. In addition, "carrier mobility" herein is used in a broad sense, including electron mobility and hole mobility.

However, publicly known polyacene compounds have low solubility in a solvent, and therefore film formation by an application process, a printing process or the like is difficult. Therefore, a device (hereinafter, also referred to as "device") having semiconductor characteristics is forced to be prepared according to a vapor deposition process requiring high manufacturing cost. Further, the publicly known polyacene compounds also have a problem on chemical stability such as oxidation resistance, and therefore is a difficult material from a viewpoint of industrial practicality.

Consequently, in order to improve the solubility and the chemical stability, study has been conducted on compounds in which various kinds of substituents are introduced on an acene skeleton (see Patent literature No. 1 and Non-patent literature No. 1, for example). Further, study has been already conducted on compounds in which chalcogen such as sulfur and selenium is introduced on a part of an acene skeleton, for example, dibenzothienothiophene (BTBT) and dinaphthothienothiophene (DNTT) (see Patent literature Nos. 2 to 3, for example).

According to the Patent literature described above, success has been made in improving the chemical stability in the compounds while high carrier mobility is maintained. However, the compounds are linear and have highly symmetrical molecular structure, and therefore have a problem of solubility being not necessarily sufficient even if a substituent such as an alkyl group is introduced thereon, or the like. Moreover, as the molecular structure becomes further complicated, the compounds can be barely synthesized using an expensive raw material or a reactant having a high environmental load, and through multi-step synthesis.

Thus, various kinds of organic compounds having semiconductor characteristics have been developed so far. However, development has not sufficiently been made yet for an organic compound having excellent chemical stability, high solubility in a solvent and high carrier mobility (material that can be applied or printed in a solution state, and can be applied to a wide range of uses, such as transistor preparation).

Therefore, organic semiconductor materials having as a basic skeleton a nonlinear molecule having low symmetry rather than a linear type have attracted attention in recent years. Specific examples include a compound having V-shaped or U-shaped structure, such as dinaphthofuran, dinaphthothiophene, dianthrafuran and dianthrathiophene. Basic skeletons thereof (unsubstituted compounds) have been already publicly known (see Patent literature Nos. 4 to 5, Non-patent literature Nos. 2 to 6, for example). However, while the compounds are excellent in chemical and thermal stability, the compounds have a problem of poor solubility in a solvent.

Several examples of compounds in which a substituent is introduced on the skeleton have been already disclosed (see Patent literature No. 6 and Non-patent literature No. 7, for example). Patent literature No. 6 refers to a dinaphthothiophene derivative on which four to twelve alkyl groups or phenyl groups are introduced, and an organic film including the derivative. However, Patent literature No. 6 discloses no synthesis example of the derivative at all, and has no description at a degree according to which a so-called person skilled in the art can understand a method for manufacturing the derivative, and thus the derivative is not substantially disclosed therein. Moreover, no verification has been made for solubility of the derivative in any solvent, application properties of a solution containing the derivative, and semiconductor characteristics of the derivative, and an effect due to introduction of the substituent thereon is also unknown. In addition thereto, no disclosure has been made on a compound itself for a dinaphthothiophene derivative on which one to three alkyl groups or phenyl groups are introduced. Further, Non-patent literature No. 7 discloses a dianthrathiophene derivative represented by the formula described below, but no verification has been made on the semiconductor characteristics in a similar manner.

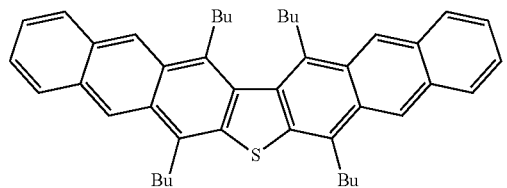

wherein, Bu is butyl.

CITATION LIST

Patent Literature

Patent literature No. 1: WO 2005/80304 A.
Patent literature No. 2: WO 2006/77888 A.
Patent literature No. 3: WO 2008/50726 A.
Patent literature No. 4: JP 2008-545729 A.
Patent literature No. 5: WO 2010/36765 A.
Patent literature No. 6: JP 2007-197400 A.

Non-Patent Literature

Non-patent literature No. 1: Journal of the American Chemical Society, 2001, Vol. 123, p. 9482.
Non-patent literature No. 2: Bulletin des Societes Chimiques Belges, 1956, Vol. 65, p. 874.
Non-patent literature No. 3: Journal of the Chemical Society, 1959, p. 1670.
Non-patent literature No. 4: Journal of the Chemical Society, 1928, p. 1148.
Non-patent literature No. 5: Chemische Berichte, 1880, Vol. 13, p. 1725.

Non-patent literature No. 6: Org Lett, 2012, Vol. 14, p. 78.
Non-patent literature No. 7: Org Lett, 2009, Vol. 11, p. 3702.

SUMMARY OF INVENTION

Technical Problem

An organic compound that is easy to synthesize, and has excellent chemical stability, semiconductor characteristics (high carrier mobility) and high solubility in a solvent allows film formation by a method such as an application process and a printing process by using a solution containing the relevant organic compound, and thus has a significantly large utility value.

More specifically, an object of the invention is to provide an organic compound that is easy to synthesize, and has excellent chemical stability, semiconductor characteristics (high carrier mobility) and high solubility in a solvent, a method for manufacturing the organic compound, an organic semiconductor material composed of the organic compound, an organic semiconductor film including the organic semiconductor material, and an organic field effect transistor (FET) having the organic semiconductor film.

Solution to Problem

The present inventors have diligently conducted study in order to achieve the object. As a result, the present inventors have found that the object can be achieved by a novel chalcogen-containing organic compound having a constitution described below, and thus have completed the invention.

More specifically, the invention concerns item 1 to item 15 described below.

Item 1. A compound represented by formula (1):

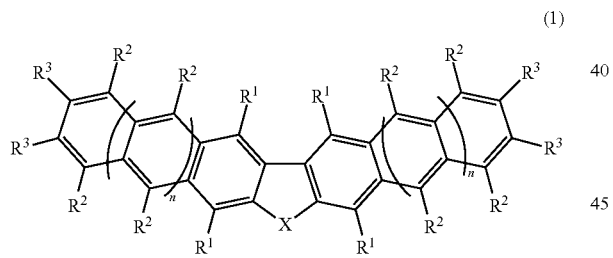

(1)

wherein, in formula (1), X is oxygen, sulfur or selenium; both of n are each independently 0 or 1; $R^1$ to $R^3$ are each independently hydrogen, fluorine, alkyl having 1 to 20 carbons, aryl, pyridyl, furyl, thienyl or thiazolyl, at least one of hydrogen in the alkyl may be replaced by fluorine, and at least one of hydrogen on a ring of the aryl, the pyridyl, the furyl, the thienyl and the thiazolyl may be replaced by at least one kind selected from halogen and alkyl having 1 to 10 carbons; however, except for a case where X is selenium, a case where all of $R^1$ to $R^3$ are simultaneously hydrogen is excluded, and a case where X is sulfur and all of $R^1$ are simultaneously butyl is also excluded.

Item 2. The compound according to item 1, wherein requirements (A) and (B) are satisfied in formula (1): (A) all of $R^1$ to $R^2$ are hydrogen; (B) except for a case where X is selenium, a case where all of $R^3$ are an identical atom or group is excluded.

Item 3. The compound according to item 2, represented by formula (1-1) or formula (1-2):

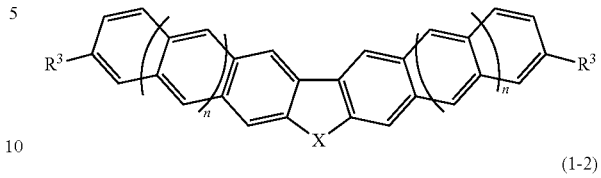

(1-1)

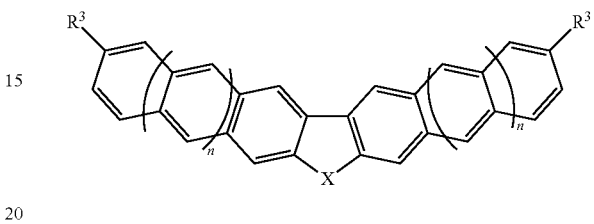

(1-2)

wherein, in formula (1-1) and formula (1-2), X and n each are defined in a manner identical with the definitions of an identical symbol in formula (1); and both of $R^3$ are each independently fluorine, alkyl having 1 to 20 carbons, aryl, pyridyl, furyl, thienyl or thiazolyl, at least one of hydrogen in the alkyl may be replaced by fluorine, and at least one of hydrogen on a ring of the aryl, the pyridyl, the furyl, the thienyl and the thiazolyl may be replaced by at least one kind selected from halogen and alkyl having 1 to 10 carbons.

Item 4. The compound according to item 3, wherein $R^3$ in formula (1-1) and formula (1-2) is an identical group selected from alkyl having 4 to 15 carbons, phenyl, furyl and thienyl.

Item 5. A compound represented by formula (2):

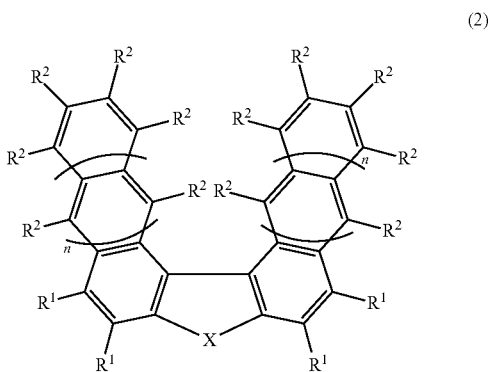

(2)

wherein, in formula (2), X is oxygen, sulfur or selenium; both of n are each independently 0 or 1; $R^1$ to $R^2$ are each independently hydrogen, alkyl having 1 to 20 carbons, aryl, pyridyl, furyl, thienyl or thiazolyl, at least one of hydrogen in the alkyl may be replaced by fluorine, and at least one of hydrogen on a ring of the aryl, the pyridyl, the furyl, the thienyl and the thiazolyl may be replaced by at least one kind selected from halogen and alkyl having 1 to 10 carbons; however, a case where all of $R^1$ to $R^2$ are simultaneously hydrogen is excluded.

Item 6. The compound according to item 5, wherein all of $R^2$ are hydrogen in formula (2).

Item 7. The compound according to item 6, represented by formula (2-1):

(2-1)

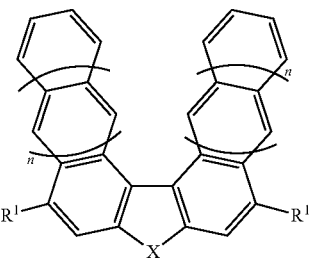

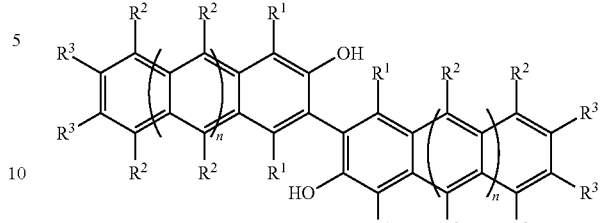

(13)

wherein, in formula (2-1), X and n each are defined in a manner identical with the definitions of an identical symbol in formula (2); and both of $R^1$ are each independently alkyl having 1 to 20 carbons, aryl, pyridyl, furyl, thienyl or thiazolyl, at least one of hydrogen in the alkyl may be replaced by fluorine, and at least one of hydrogen on a ring of the aryl, the pyridyl, the furyl, the thienyl and the thiazolyl may be replaced by at least one kind selected from halogen and alkyl having 1 to 10 carbons.

Item 8. The compound according to item 7, wherein $R^1$ in formula (2-1) is an identical group selected from alkyl having 6 to 15 carbons, phenyl, furyl, thienyl and thiazolyl.

Item 9. A method for manufacturing the compound (wherein, X is sulfur or selenium) according to item 1, comprising: a step for allowing coupling of compounds represented by formula (11) to obtain a compound represented by formula (12); a step for allowing deprotection of methoxy of the compound represented by formula (12) to obtain a compound represented by formula (13); a step for allowing the compound represented by formula (13) to react with N,N-dialkyl thiocarbamoyl chloride or N,N-dialkyl selenocarbamoyl chloride to obtain a compound represented by formula (14); and a step for heating the compound represented by formula (14) to obtain a compound represented by formula (15):

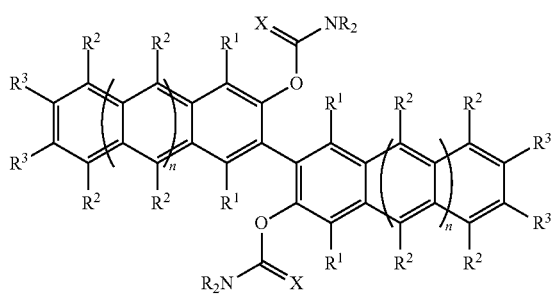

(14)

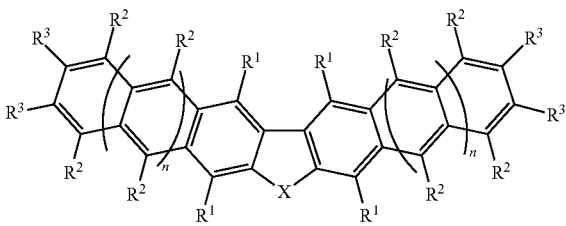

(15)

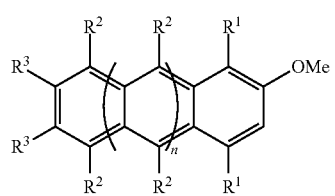

(11)

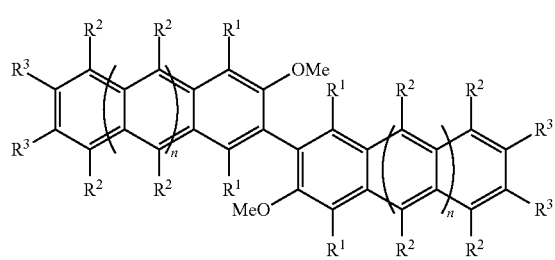

(12)

X = S, Se wherein, in formulas (11) to (15), X is sulfur or selenium, n and $R^1$ to $R^3$ each are defined in a manner identical with the definitions of an identical symbol in formula (1), Me is methyl, and in formula (14), R's are each independently alkyl having 1 to 3 carbons.

Item 10. A method for manufacturing the compound (wherein, X is selenium) according to item 1, comprising: a step for allowing coupling of compounds represented by formula (11) to obtain a compound represented by formula (12); a step for allowing deprotection of methoxy of the compound represented by formula (12) to obtain a compound represented by formula (13); a step for allowing the compound represented by formula (13) to react with trifluoromethanesulfonyl chloride or tri fluoromethanesulfonic anhydride to obtain a compound represented by formula (16); a step for allowing coupling of the compounds represented by formula (16) with boranes to obtain boronic ester represented by formula (17); a step for brominating the boronic ester represented by formula (17) with copper bromide to obtain a compound represented by formula (18); and a step for lithiating the compound represented by formula (18), and then allowing the resulting product to react with selenium chloride to obtain a compound represented by formula (15):

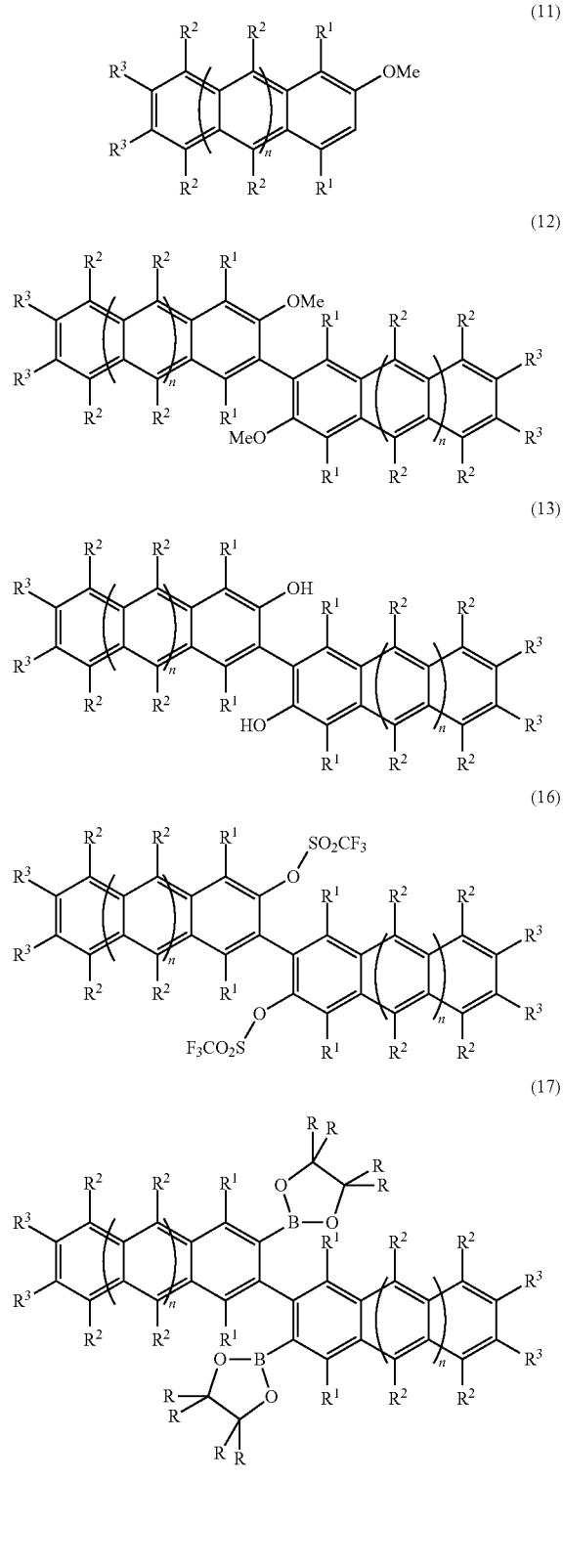

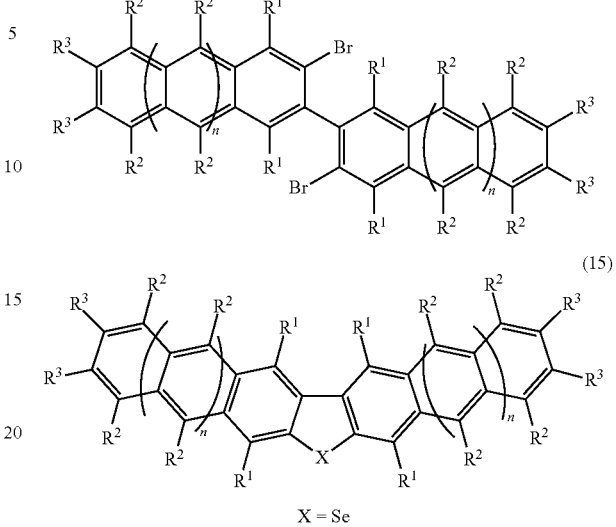

wherein, in formulas (11) to (13) and formulas (15) to (18), X is selenium, n and $R^1$ to $R^3$ each are defined in a manner identical with the definitions of an identical symbol in formula (1), Me is methyl, and in formula (17), R's are each independently alkyl having 1 to 3 carbons.

Item 11. A method for manufacturing the compound (wherein, X is oxygen) according to item 1, comprising: a step for allowing coupling of compounds represented by formula (11) to obtain a compound represented by formula (12); a step for allowing deprotection of methoxy of the compound represented by formula (12) to obtain a compound represented by formula (13); a step for heating and dehydrating the compound represented by formula (13) under a zeolite catalyst to obtain a compound represented by formula (15):

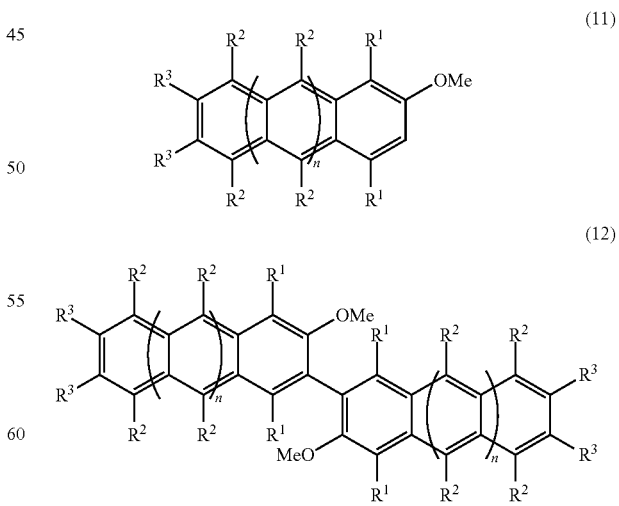

-continued

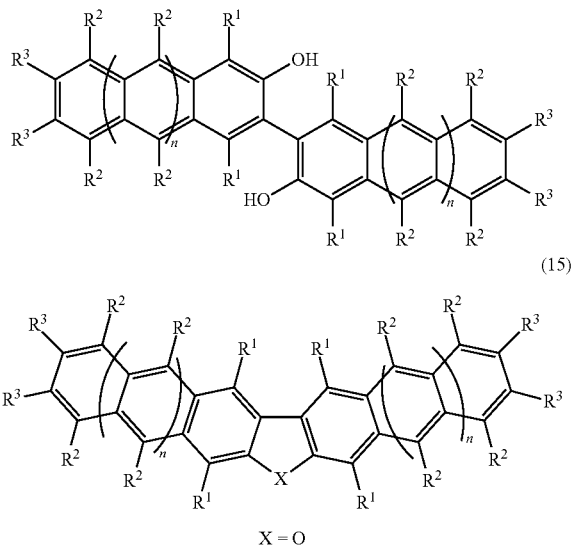

(13)

(15)

X = O wherein, in formulas (11) to (13) and (15), X is oxygen, n and $R^1$ to $R^3$ each are defined in a manner identical with the definitions of an identical symbol in formula (1), and Me is methyl.

Item 12. A method for manufacturing the compound according to item 7, comprising: a step for brominating a compound represented by formula (27) to obtain a compound represented by formula (28); and a step for allowing the compound represented by formula (28) to react with a cross-coupling reactant to obtain a compound represented by formula (29). See FIG. 7.

In formulas (27) to (29) of FIG. 7, X, n and $R^1$ each are defined in a manner identical with the definitions of an identical symbol in formula (2-1).

Item 13. An organic semiconductor material, composed of the compound according to any one of items 1 to 8.

Item 14. An organic semiconductor film, including the organic semiconductor material according to item 13.

Item 15. An organic field effect transistor having a substrate, a gate electrode, a gate insulating film, a source electrode, a drain electrode and an organic semiconductor layer, wherein the organic semiconductor layer is constituted of the organic semiconductor film according to item 14.

Advantageous Effects of Invention

The invention can provide an organic compound that is easy to synthesize, and has excellent chemical stability, semiconductor characteristics (high carrier mobility) and high solubility in a solvent, a method for manufacturing the organic compound, an organic semiconductor material composed of the organic compound, an organic semiconductor film including the organic semiconductor material, and an organic field effect transistor (FET) having the organic semiconductor film.

BRIEF DESCRIPTION OF DRAWINGS

FIG. 4 is a drawing showing FET characteristics of a compound synthesized in Example 7.

DESCRIPTION OF EMBODIMENTS

Figure 1:
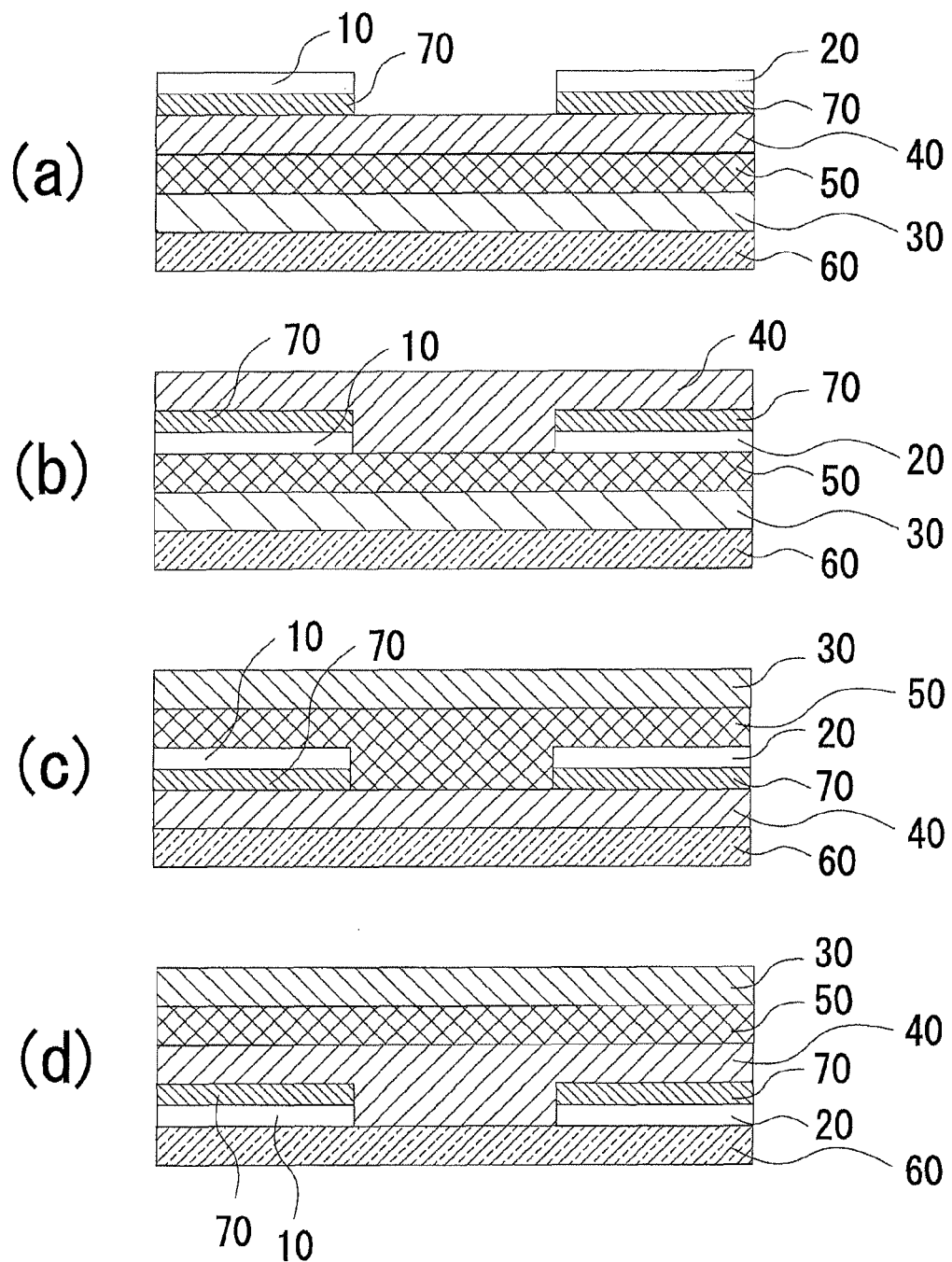
FIG. 1 is a cross-sectional view of an organic field effect transistor (FET) having a bottom gate-top contact type (a), a bottom gate-bottom contact type (b), a top gate-top contact type (c) or a top gate-bottom contact type (d).

The invention will be described in detail below.
Chalcogen-Containing Organic Compound A chalcogen-containing organic compound of the invention includes a compound represented by formula (1) or formula (2), has a V-shaped (formula (1)) or U-shaped (formula (2)) structure in which benzene rings are stretched on both wings with a chalcogen bridging part (—X—) as a bent point, and has a substituent in an arbitrary position on one of the benzene rings. In addition, "substituent" herein means an atom or a group other than hydrogen.

A compound represented by formula (1) is also referred to as "compound (1)," a compound represented by formula (2) is also referred to as "compound (2)," and compound (1) and compound (2) are also collectively referred to as "compound of the invention" below. Moreover, a compound represented by any other formula (i) is also referred to as "compound (i)" (i is a formula number).

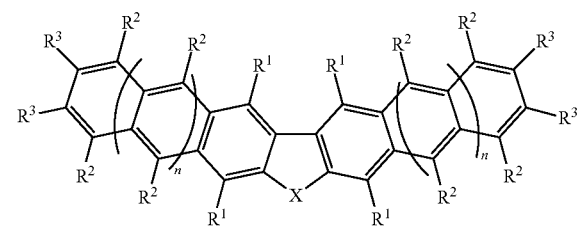
(1)

In formula (1), a meaning of each symbol is as described below.

X is oxygen, sulfur or selenium, and in view of demonstrating high carrier mobility of the compound, preferably, oxygen or sulfur, and particularly preferably, sulfur.

Both of n are each independently 0 or 1, and preferably, 0.

$R^1$, $R^2$ and $R^3$ are each independently hydrogen, fluorine, alkyl having 1 to 20 carbons, aryl, pyridyl, furyl (furan ring), thienyl (thiophene ring) or thiazolyl (thiazole ring). At least one of hydrogen in the alkyl may be replaced by fluorine. At least one of hydrogen on a ring of the aryl, the pyridyl, the furyl, the thienyl and the thiazolyl may be replaced by at least one kind selected from halogen and alkyl having 1 to 10 carbons (preferably, 1 to 6 carbons, further preferably, 1 to 3 carbons). In addition, "each independently" in specifying $R^1$, $R^2$ and $R^3$ means that $R^1$, $R^2$ and $R^3$ may be identical or different with each other, and also a plurality of $R^1$ may be identical or different with each other, a plurality of $R^2$ may be identical or different with each other, and a plurality of $R^3$ may be identical or different with each other.

When both of n are 0 in formula (1), atoms or groups bonded with carbons on 12-position and 13-position are preferably identical, and atoms or groups bonded with carbons on 1-position and 11-position, 2-position and 10-position, 3-position and 9-position, 4-position and 8-position, and 5-position and 7-position each are also preferably identical in a similar manner.

When both of n are 1 in formula (1), atoms or groups bonded with carbons on 15-position and 16-position are preferably identical, and atoms or groups bonded with carbons on 14-position and 17-position, 1-position and 13-position, 2-position and 12-position, 3-position and 11-position, 4-position and 10-position, 5-position and 9-position, and 6-position and 8-position each are also preferably identical in a similar manner.

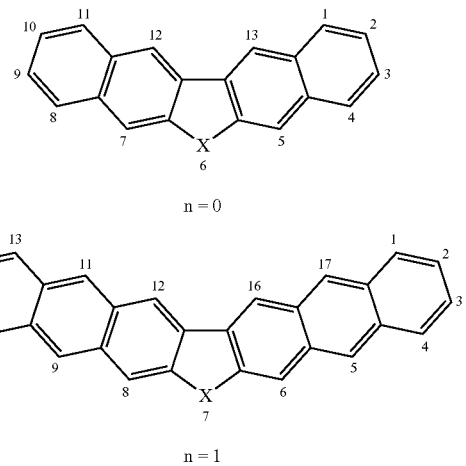

However, except for a case where X is selenium, a case where all of $R^1$ to $R^3$ are simultaneously hydrogen is excluded. Moreover, a case where X is sulfur and all of $R^1$ are simultaneously butyl is also excluded.

In formula (1), requirements (A) and (B) are preferably satisfied.
(A) All of $R^1$ to $R^2$ are hydrogen.
(B) Except for a case where X is selenium, a case where all of $R^3$ are an identical atom or group is excluded.

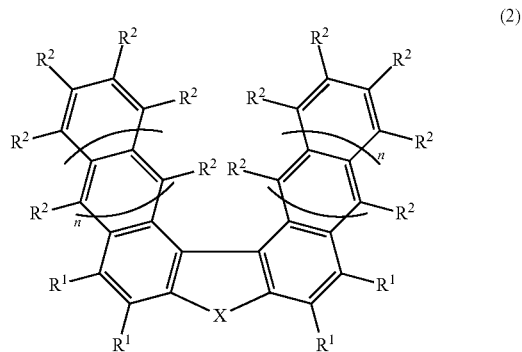
(2)

In formula (2), a meaning of each symbol is as described below.

X is oxygen, sulfur or selenium.

Both of n are each independently 0 or 1, and preferably, 0.

$R^1$ and $R^2$ are each independently hydrogen, alkyl having 1 to 20 carbons, aryl, pyridyl, furyl (furan ring), thienyl (thiophene ring) or thiazolyl (thiazole ring). At least one of hydrogen in the alkyl may be replaced by fluorine. At least one of hydrogen on a ring of the aryl, the pyridyl, the furyl, the thienyl and the thiazolyl may be replaced by at least one kind selected from halogen and alkyl having 1 to 10 carbons (preferably, 1 to 6 carbons, and further preferably, 1 to 3 carbons). In addition, "each independently" in specifying $R^1$ and R² means that R¹ and R² may be identical or different with each other, and also a plurality of R¹ may be identical or different with each other, and a plurality of R² may be identical or different with each other.

However, a case where all of R¹ to R² are simultaneously hydrogen is excluded.

When both of n are 0 in formula (2), atoms or groups bonded with carbons on 1-position and 13-position are preferably identical, and atoms or groups bonded with carbons on 2-position and 12-position, 3-position and 11-position, 4-position and 10-position, 5-position and 9-position, and 6-position and 8-position each are also preferably identical in a similar manner.

When both of n are 1 in formula (2), atoms or groups bonded with carbons on 1-position and 15-position are preferably identical, and atoms or groups bonded with carbons on 2-position and 14-position, 3-position and 13-position, 4-position and 12-position, 5-position and 11-position, 6-position and 10-position, 7-position and 9-position, and 16-position and 17-position each are also preferably identical in a similar manner.

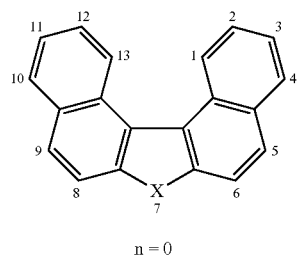

n = 0

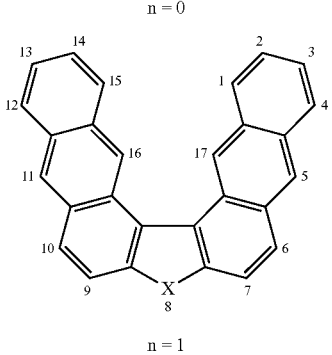

n = 1

In formula (2), all of R² are preferably hydrogen.

Specific examples of alkyl having 1 to 20 carbons listed as R¹ to R³ in formulas (1) to (2) include methyl, ethyl, propyl, butyl, pentyl, hexyl, heptyl, octyl, nonyl, decyl, dodecyl, undecyl and octadecyl. In view of satisfying both high solubility of the compound of the invention in a solvent and ease of overlap of electron cloud between molecules, the number of carbon atoms in alkyl is preferably 4 to 15, further preferably, 4 to 12, and particularly preferably, 6 to 12. Alkyl may have any of a straight-chain shape and a branched-chain shape, and preferably a straight-chain shape from a viewpoint of molecular arrangement in a crystal.

Specific examples of a group formed by replacing at least one of hydrogen in the alkyl by fluorine include a group in which all of hydrogen in the alkyl are replaced by fluorine, such as trifluoromethyl, perfluorohexyl, perfluoro octyl and perfluorodecyl; and a group in which only hydrogen bonded with carbon directly bonded with an aromatic ring is not replaced by fluorine, and all of hydrogen other than the above hydrogen are replaced by fluorine, such as trifluoroethyl, 1H,1H-perfluorohexyl, 1H,1H-perfluorooctyl and 1H,1H-perfluorodecyl.

Specific examples of aryl listed as R¹ to R³ in formulas (1) to (2) include phenyl, naphthyl (1-naphthyl, 2-naphthyl), fluorenyl (example: 2-fluorenyl) and biphenyl. The number of carbon atoms in aryl is preferably 6 to 14, and further preferably, 6 to 10. Among the groups, phenyl is particularly preferred.

Specific examples of pyridyl listed as R¹ to R³ in formulas (1) to (2) include 2-pyridyl, 3-pyridyl and 4-pyridyl.

Specific examples of the group formed by replacing at least one of hydrogen on the ring of the aryl by alkyl having 1 to 10 carbons include tolyl and xylyl. Specific examples of the group formed by replacing at least one of hydrogen on the ring of the aryl by halogen include p-fluorophenyl, pentafluorophenyl, p-chlorophenyl and pentachlorophenyl.

Specific examples of furyl listed as R¹ to R³ in formulas (1) to (2) include 2-furyl and 3-furyl; specific examples of thienyl include 2-thienyl and 3-thienyl; and specific examples of thiazolyl include 2-thiazolyl.

At least one of hydrogen on a ring of aryl, pyridyl, furyl, thienyl and thiazolyl may be replaced by halogen. Specific examples of halogen include chlorine, bromine and fluorine, and preferably, fluorine.

In compound (1) of the invention, from a viewpoint of achieving high-density assembly of organic semiconductor molecules, a disubstituted derivative, namely, a compound represented by formula (1-1) or formula (1-2) is preferred, and in view of showing high carrier mobility, a compound represented by formula (1-1) is particularly preferred.

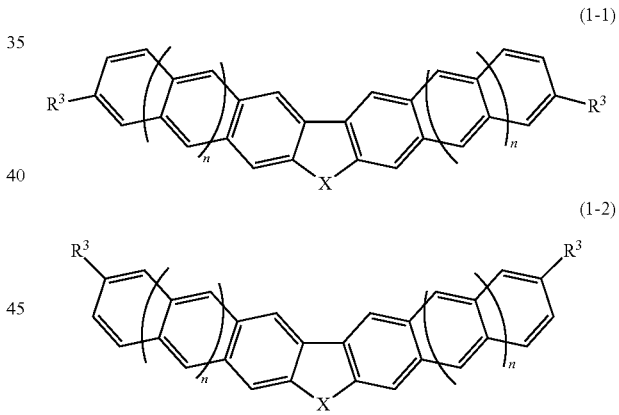

In formula (1-1) and formula (1-2), X and n each are defined in a manner identical with the definitions of an identical symbol in formula (1). Both of R³ are each independently fluorine, alkyl having 1 to 20 carbons, aryl, pyridyl, furyl, thienyl or thiazolyl. At least one of hydrogen in the alkyl may be replaced by fluorine. At least one of hydrogen on a ring of the aryl, the pyridyl, the furyl, the thienyl and the thiazolyl may be replaced by at least one kind selected from halogen and alkyl having 1 to 10 carbons. Specific examples and preferred examples of the substituents are as described above in the description of formulas (1) to (2).

In formula (1-1) and formula (1-2), both of R³ may be identical or different with each other, and are preferably an identical substituent. Both of R³ are preferably an identical group selected from alkyl having 1 to 20 carbons, phenyl, furyl and thienyl, further preferably, alkyl having 1 to 20 carbons, and in view of showing high carrier mobility of the compound of the invention, further preferably, alkyl having 4 to 15 carbons, particularly preferably, alkyl having 4 to 12 carbons, and most preferably, alkyl having 6 to 12 carbons.

In compound (1) of the invention, a compound represented by a formula described below is also preferred.

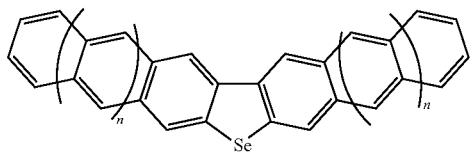

wherein, in formula, n is defined in a manner identical with the definition of an identical symbol in formula (1).

In compound (2) of the invention, from a viewpoint of achieving high-density assembly of organic semiconductor molecules, a disubstituted derivative, namely, a compound represented by formula (2-1) is preferred.

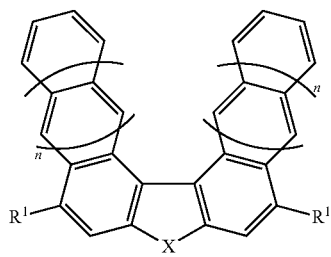

(2-1)

In formula (2-1), X and n each are defined in a manner identical with the definitions of an identical symbol in formula (2). Both of $R^1$ are each independently alkyl having 1 to 20 carbons, aryl, pyridyl, furyl, thienyl or thiazolyl. At least one of hydrogen in the alkyl may be replaced by fluorine, and at least one of hydrogen on a ring of the aryl, the pyridyl, the furyl, the thienyl and the thiazolyl may be replaced by at least one kind selected from halogen and alkyl having 1 to 10 carbons. Specific examples and preferred examples of the substituents are as described above in the description of formulas (1) to (2).

In formula (2-1), both of $R^1$ may be identical or different with each other, and preferably an identical substituent. Both of $R^1$ are further preferably an identical group selected from alkyl having 6 to 15 carbons, phenyl, furyl, thienyl and thiazolyl.

Formula (1-1), formula (1-2) and formula (2-1) are shown by formulas described below, for example.

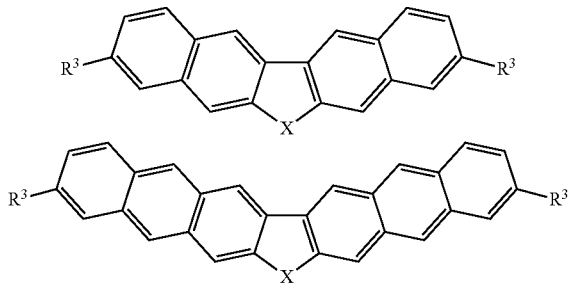

-continued

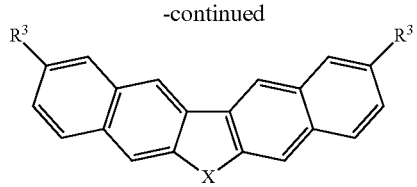

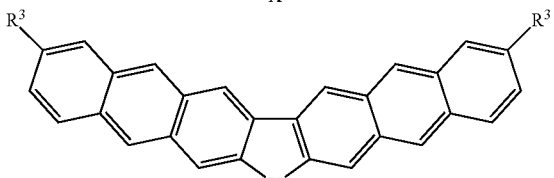

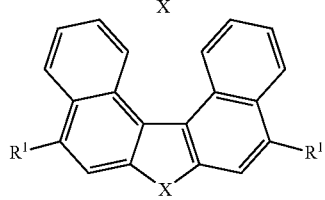

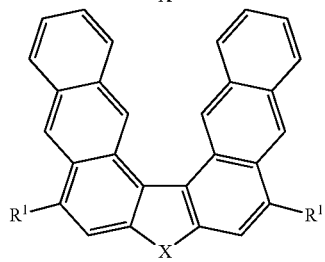

The compound of the invention shows high solubility in a solvent by structure thereof (nonlinear and chalcogen-bridging structure) and preferably by an effect of introducing a substituent thereon. More specifically, a solution can be prepared at a concentration of the compound described later. Thus, the solution containing the compound of the invention can be applied or printed onto a substrate, and an organic semiconductor film including the compound of the invention can be manufactured in a simple film-forming step. For example, film formation applying the printing process can be performed under ordinary temperature and normal pressure to allow formation of a film simply and in a short period of time, and therefore is advantageous, in view of manufacturing cost or the like, over film formation by a vapor deposition process or the like applied under a high temperature and high pressure. Therefore, the organic semiconductor film and the organic semiconductor device having the organic semiconductor film can be manufactured without adversely affecting excellent properties of the compound of the invention.

In the compound of the invention, intermolecular interaction is improved by chalcogen existing on a bent site of molecules, and π-electron orbitals are sufficiently overlapped between the molecules, and therefore the compound and the organic semiconductor film including the compound according to the invention show sufficiently high carrier mobility. Although an optimum value of the carrier mobility is different depending on a use, the carrier mobility when the film is used in the form of the organic semiconductor device is preferably 0.5 cm$^2$/V·s or more, further preferably, 1.0 cm$^2$/V·s or more, and particularly preferably, 5.0 cm$^2$/V·s or more. An upper limit of the carrier mobility is not particularly limited, but is about 50.0 cm$^2$/V·s, for example. In addition, the carrier mobility is measured on an organic semiconductor film formed using an o-xylene solution having a concentration of 0.2% by mass of the compound of the invention, a 1,2-dichloroethane solution having a concentration of 0.2% by mass thereof or an o-dichlorobenzene solution having a concentration of 0.2% by mass thereof, for example, and details of a film-forming method (examples: an edge-cast process or a gap-cast process) and a measurement method are as described in Examples.

In addition to the properties of the high carrier mobility, the compound of the invention has excellent properties as an organic semiconductor material: a high ON/OFF ratio of a drain current by a gate voltage of a transistor.

Moreover, the compound of the invention has excellent chemical stability such as excellent oxidation resistance.

Moreover, as described later, the compound of the invention can be synthesized in a short step using a reaction that is easy to perform in terms of synthetic organic chemistry, and therefore can be used as an organic semiconductor material that can be industrially manufactured, and is rich in practicality.

As described above, the compound of the invention is preferably used as the organic semiconductor material.

Specific examples of the compound of the invention are shown below.

Specific examples of compound (1) in which X is oxygen include compounds described below.

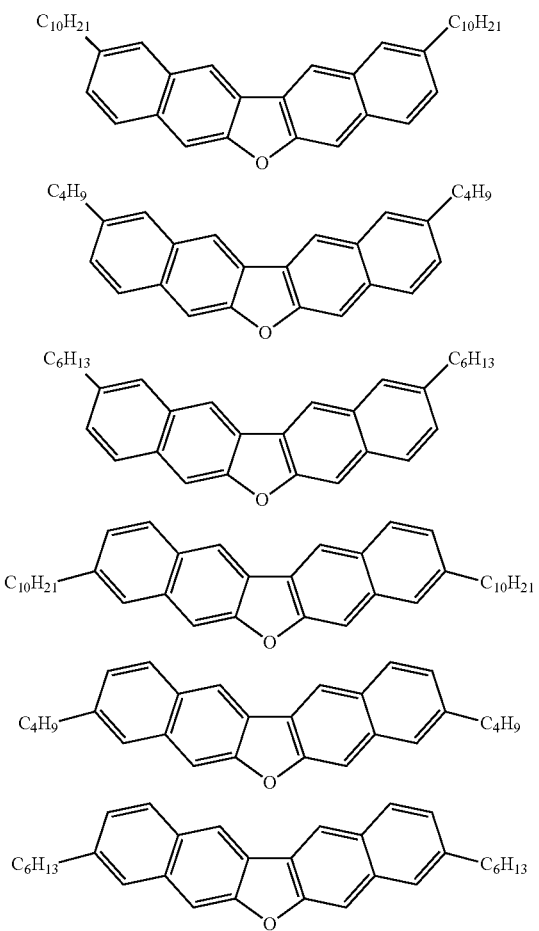

-continued

-continued
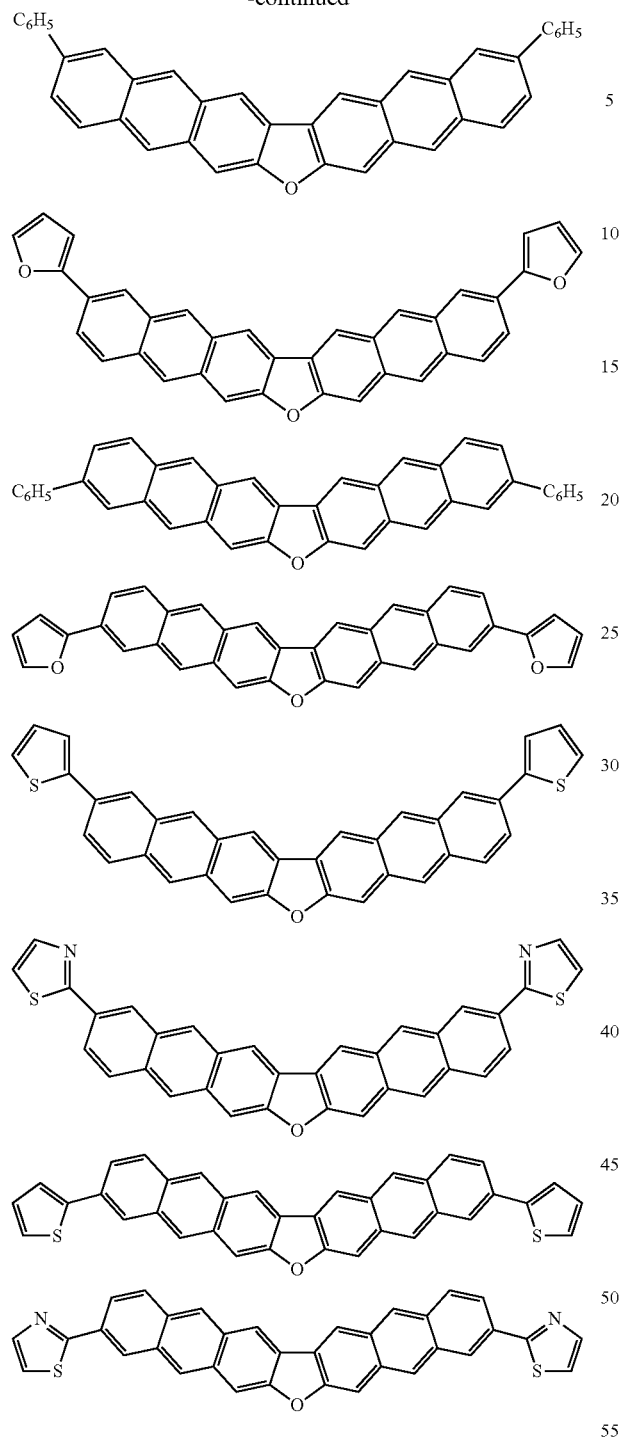
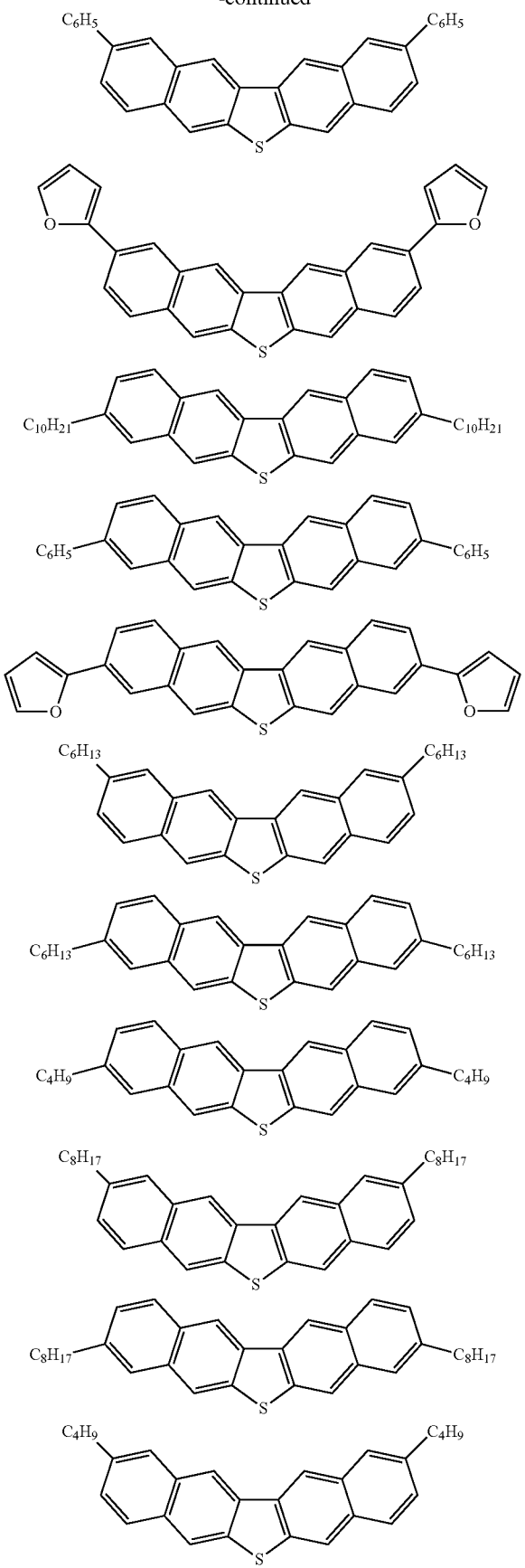
Specific examples of compound (1) in which X is sulfur include compounds described below.
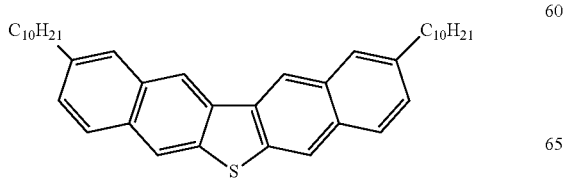

-continued
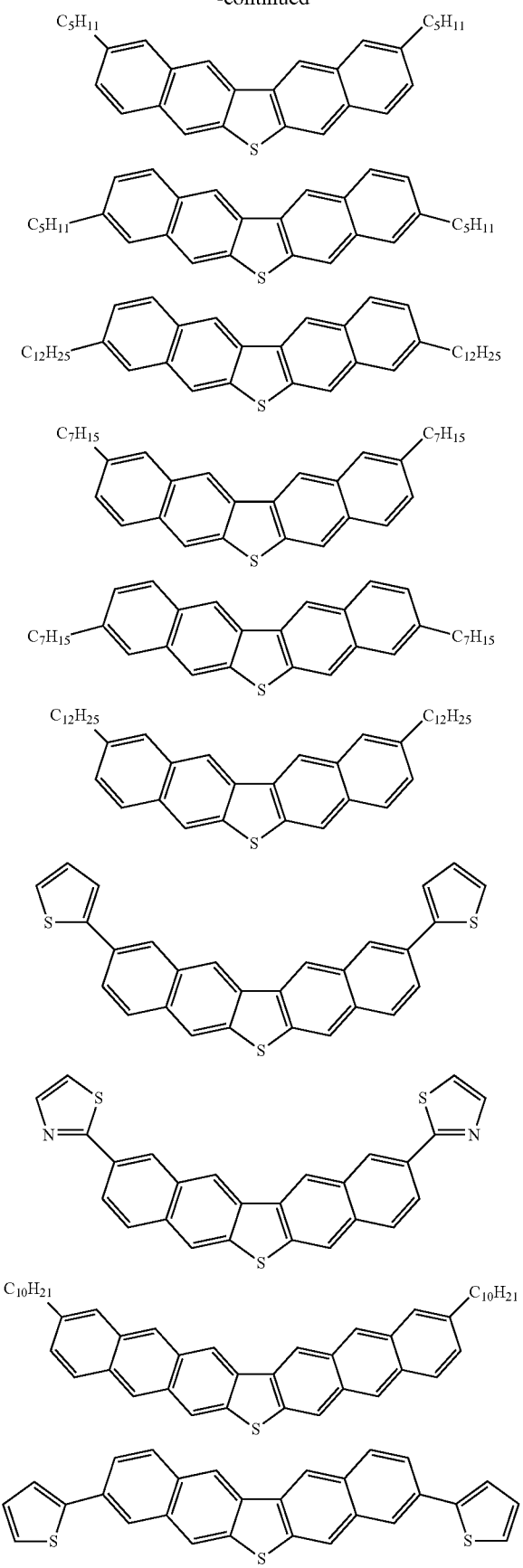
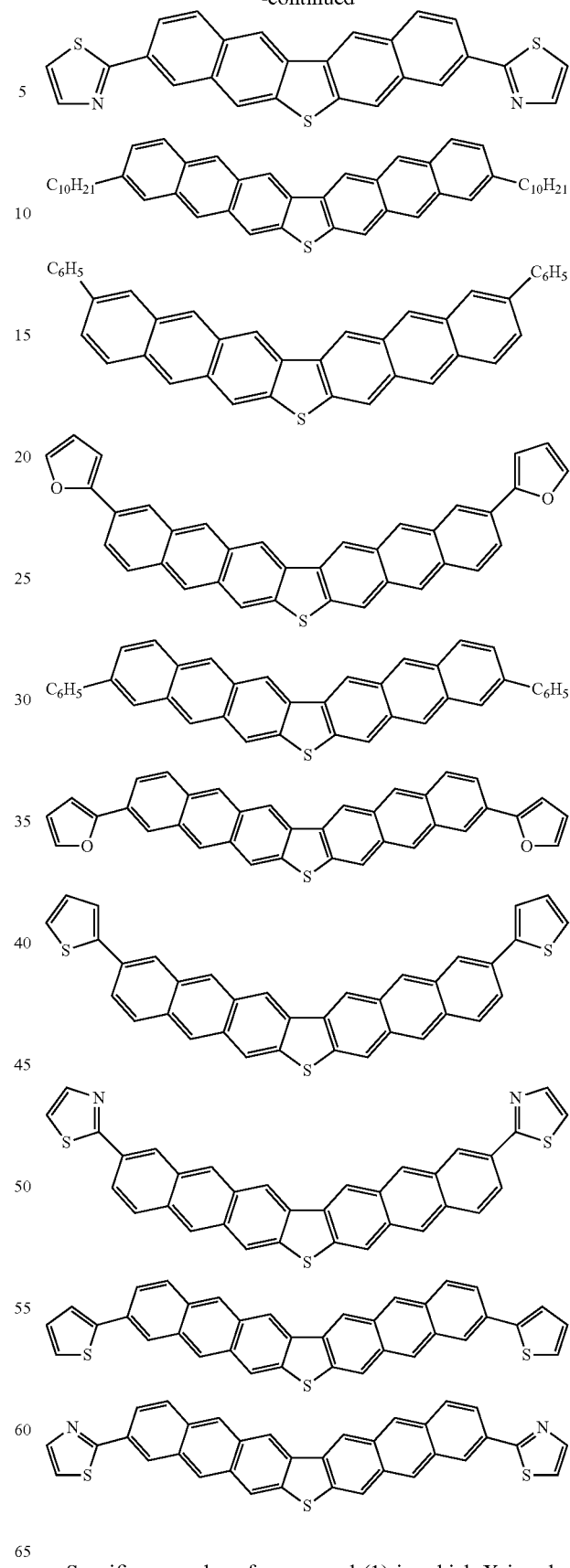
Specific examples of compound (1) in which X is selenium include compounds described below.

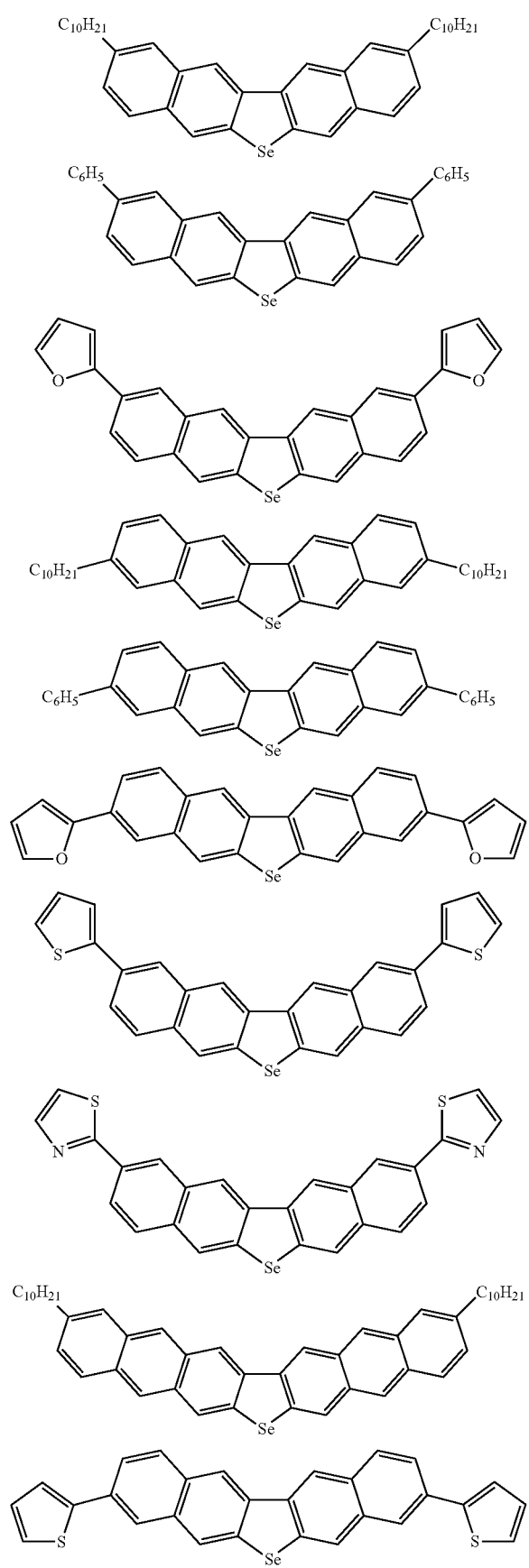
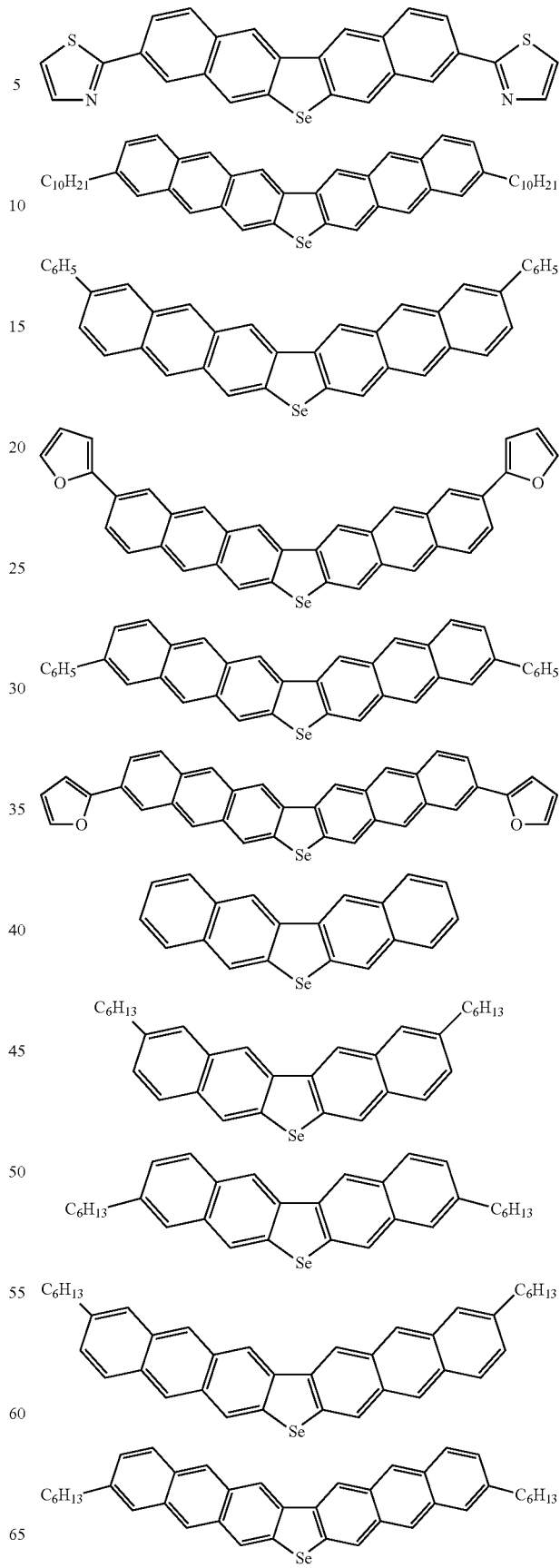
-continued

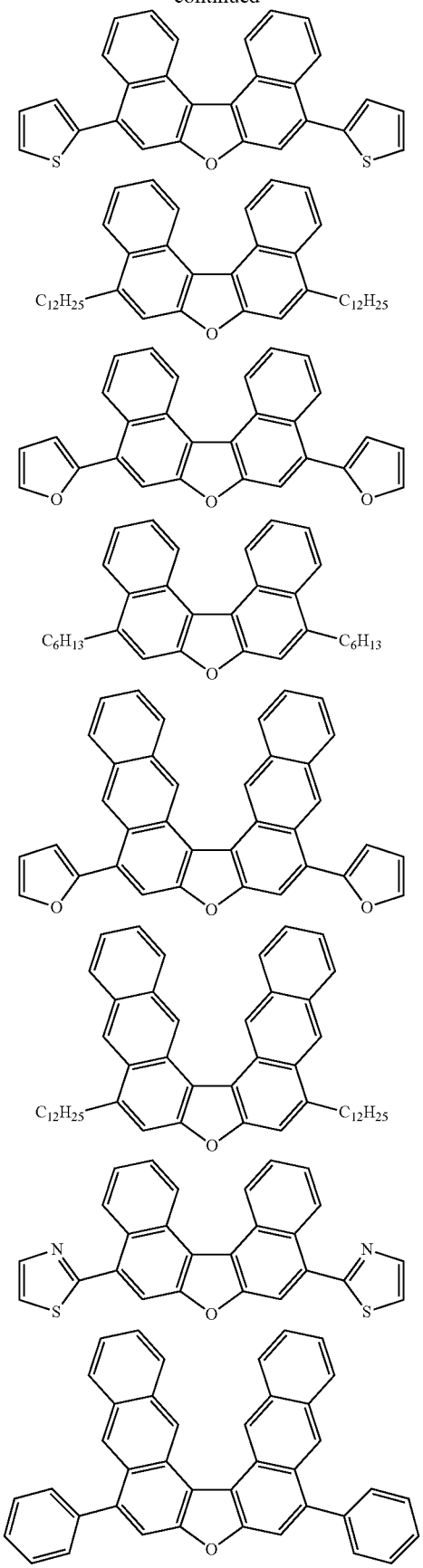
Specific examples of compound (2) in which X is oxygen include compounds described below.
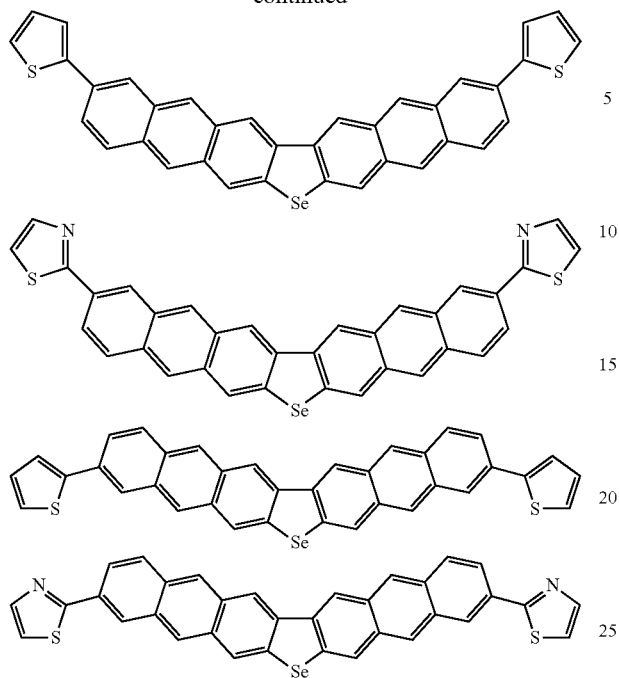

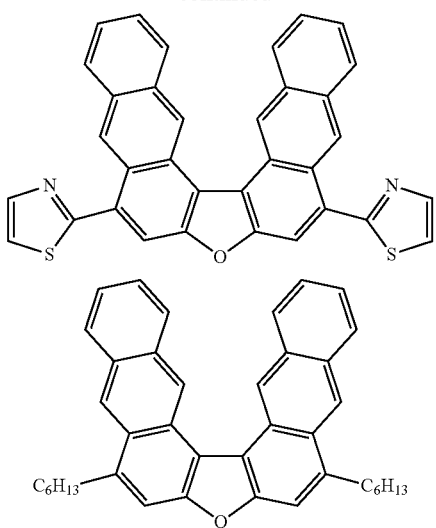
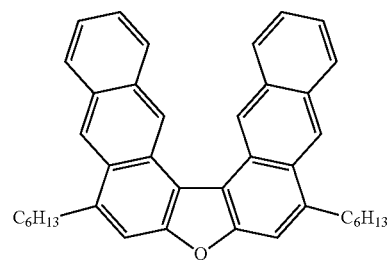
Specific examples of compound (2) in which X is sulfur include compounds described below.
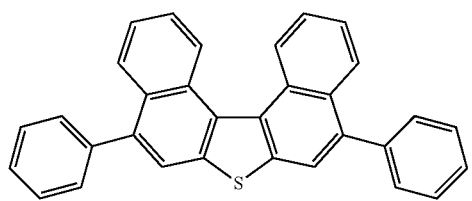
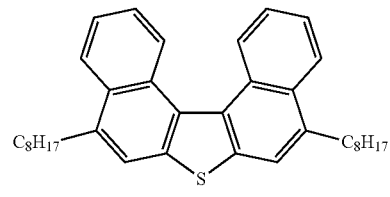
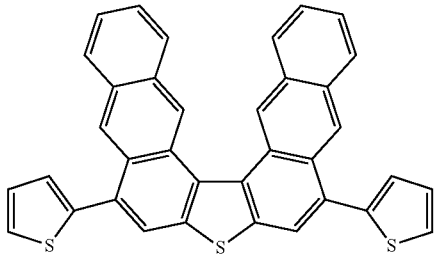
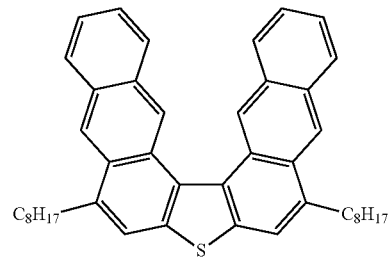
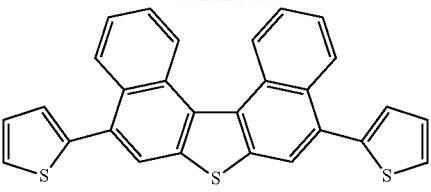
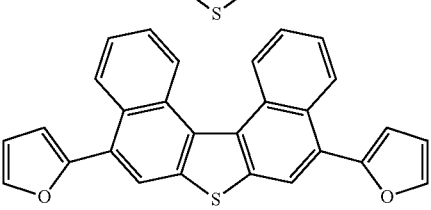
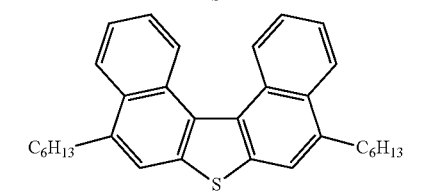
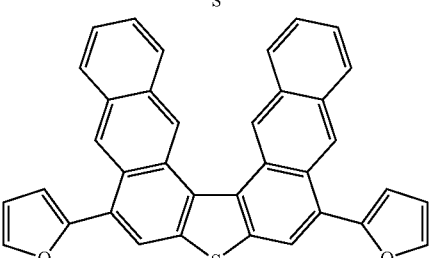
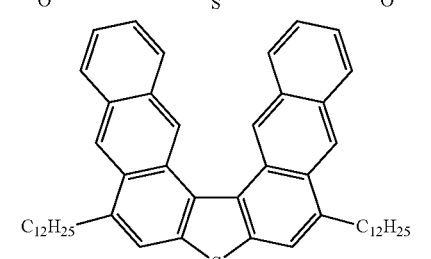
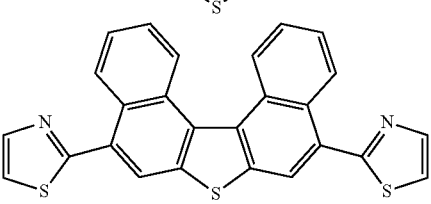
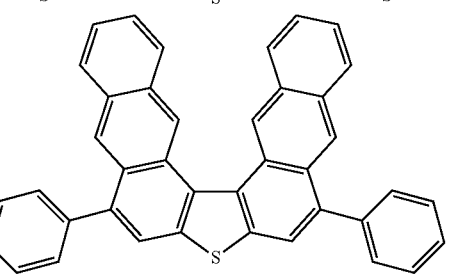

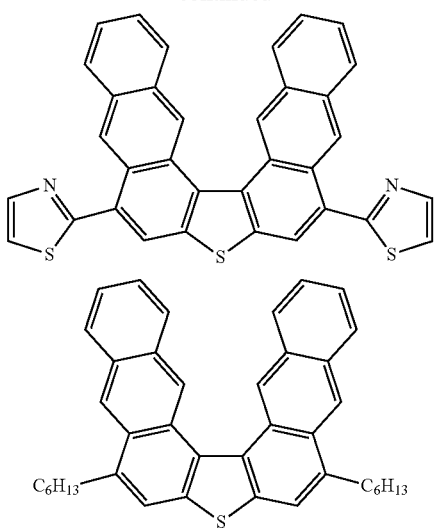
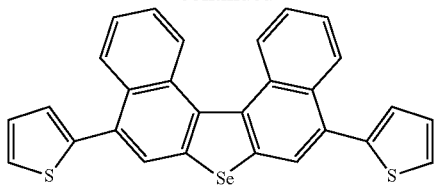
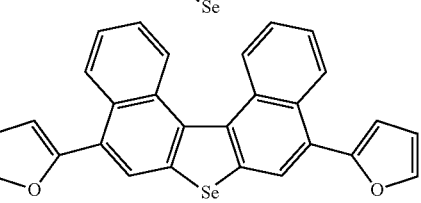
Specific examples of compound (2) in which X is selenium include compounds described below.
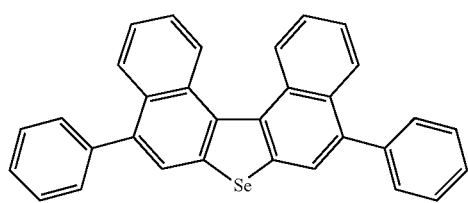
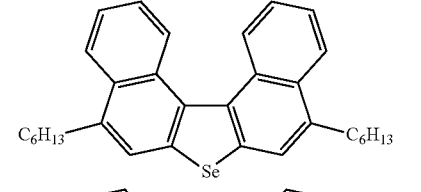
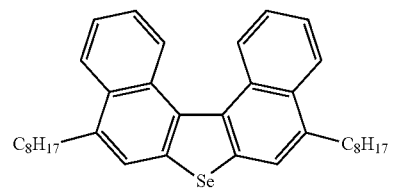
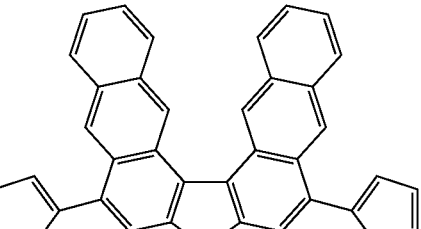
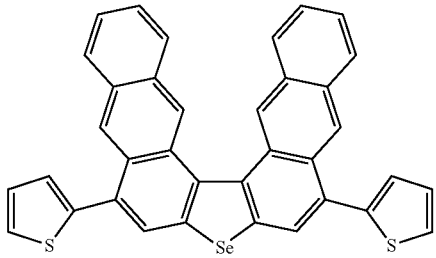
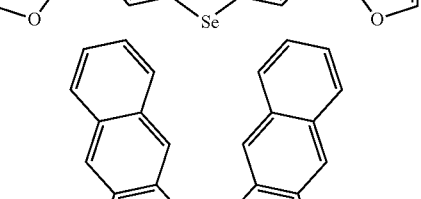
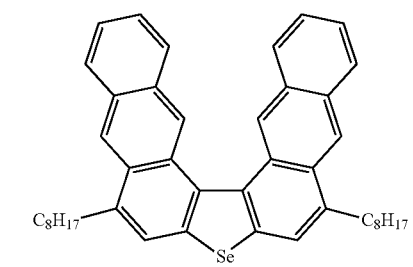
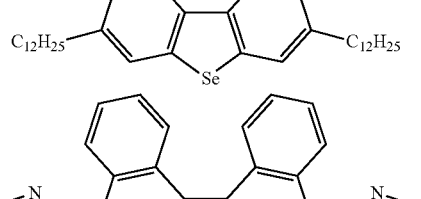
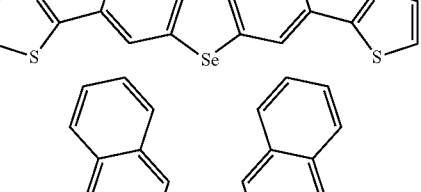
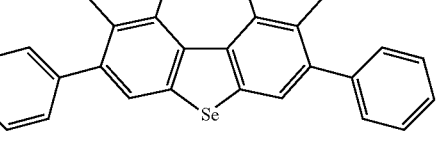

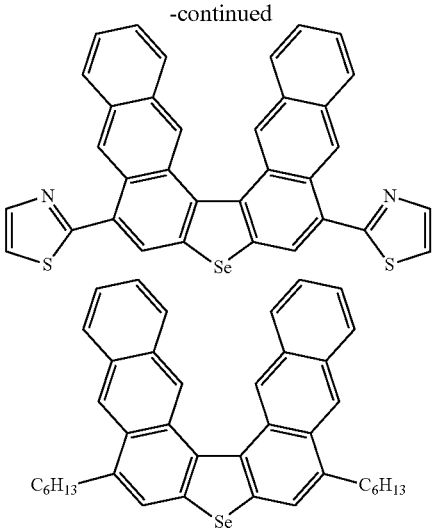

Method for Manufacturing Compound (1) and Compound (2)

A method for manufacturing compound (1) or compound (2) (X=sulfur or selenium) according to the invention comprises: step 1A for allowing coupling of compounds represented by formula (11) or formula (21) to obtain a compound represented by formula (12) or (22); step 2A for allowing deprotection of methoxy of the compound represented by formula (12) or (22) to obtain a compound represented by formula (13) or (23); step 3A for allowing the compound represented by formula (13) or (23) to react with N,N-dialkyl thiocarbamoyl chloride or N,N-dialkyl selenocarbamoyl chloride to obtain a compound represented by formula (14) or (24); and step 4A for heating the compound represented by formula (14) or (24) to obtain a compound represented by formula (15) or (25). See FIGS. 8 and 9.

A method for manufacturing compound (1) or compound (2) (X=oxygen) according to the invention comprises: step 1A described above; step 2A describe above; and step 3A' for heating and dehydrating the compound represented by formula (13) or formula (23) under a zeolite catalyst to obtain a compound represented by formula (15) or formula (26). See FIGS. 8 and 9.

Figure 8:
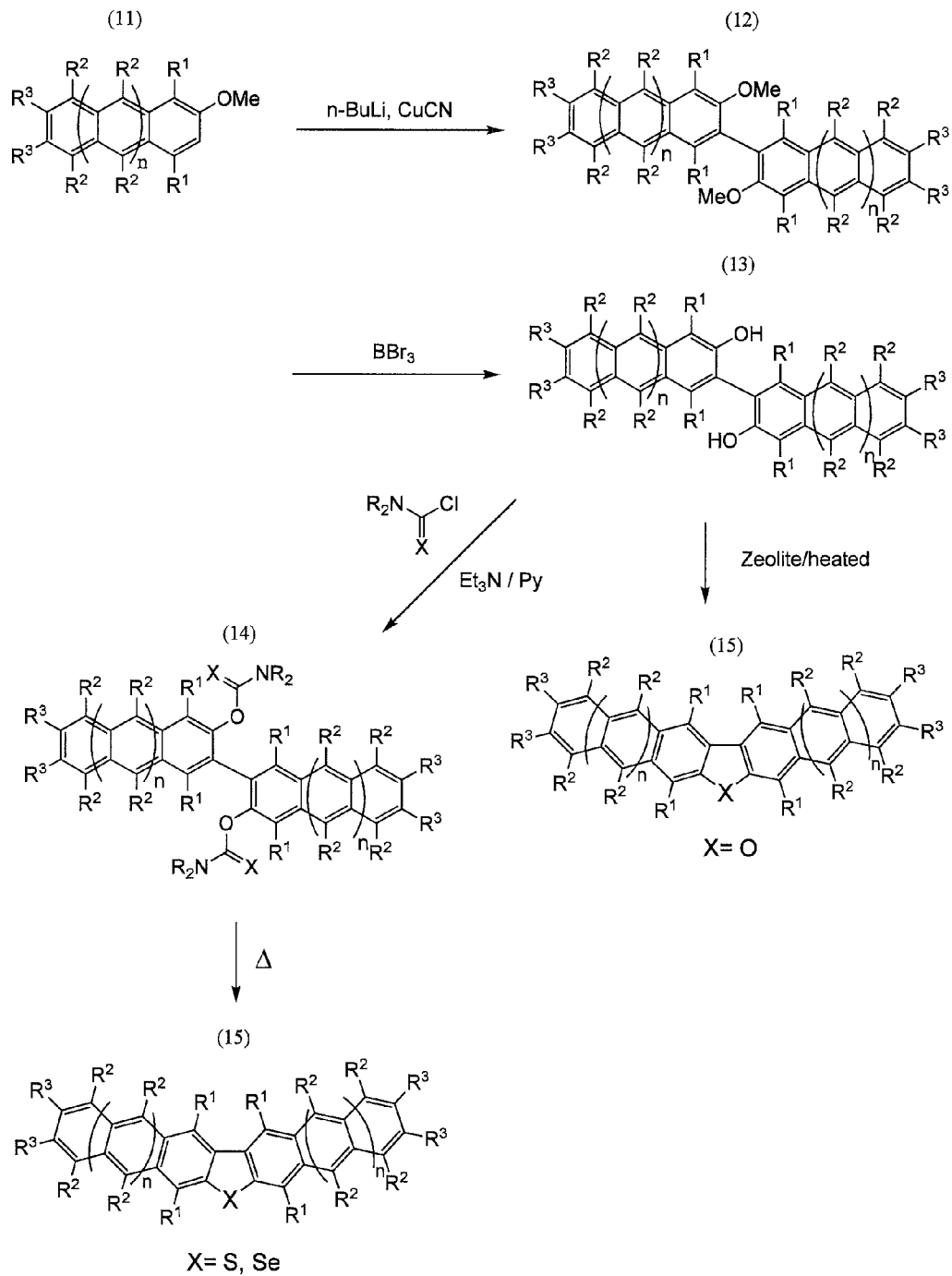
FIG. 8 shows the reaction scheme for producing a compound of formula (15).
Figure 9:
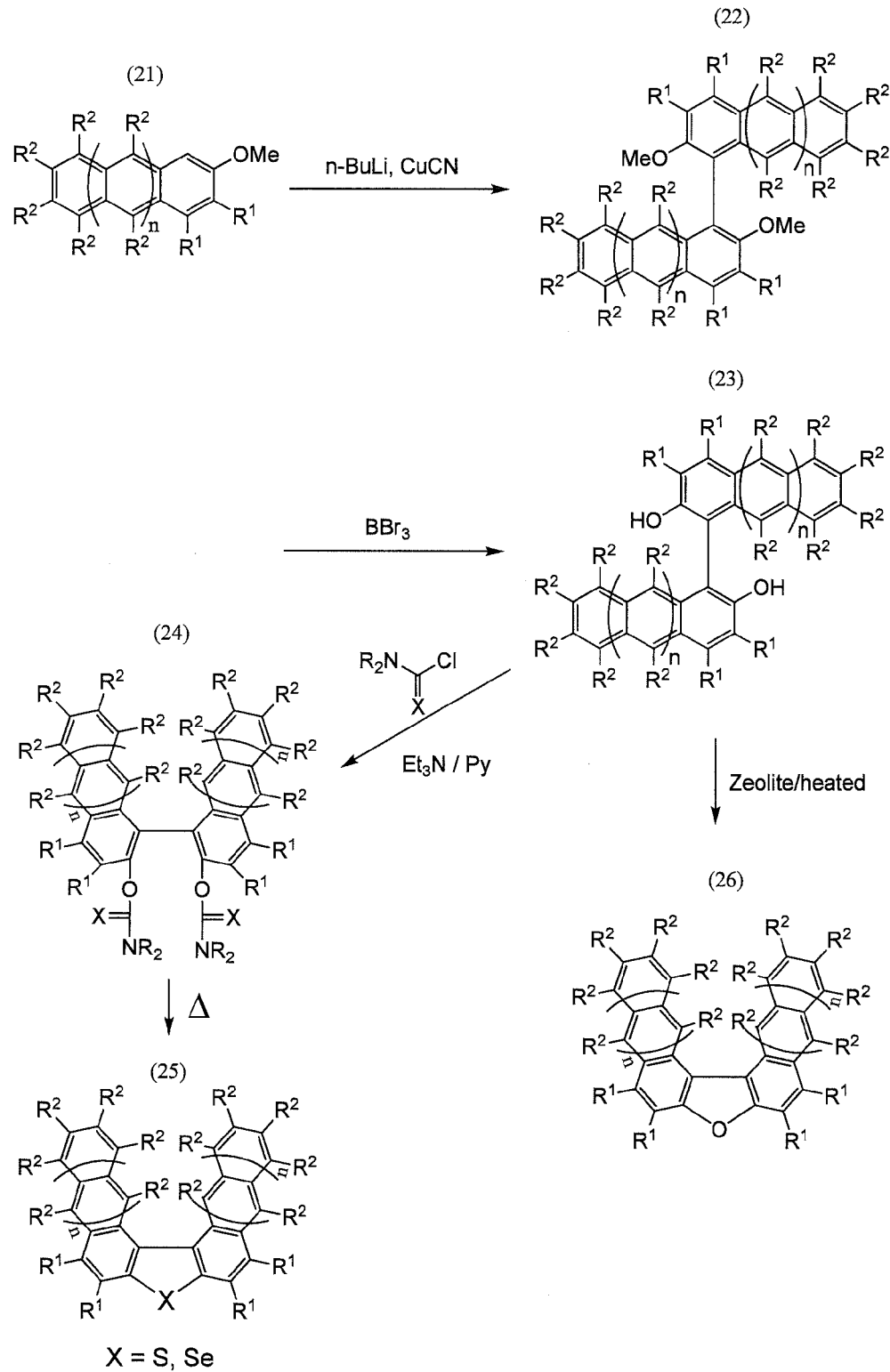
FIG. 9 shows the reaction scheme for producing a compound of formula (25) or (26).

In formulas (11) to (15) of FIG. 8, $R^1$ to $R^3$ and n each are defined in a manner identical with the definitions of an identical symbol in formula (1); in formulas (21) to (26) of FIG. 9, $R^1$ to $R^2$ and n each are defined in a manner identical with the definitions of an identical symbol in formula (2); R's are each independently alkyl having 1 to 3 carbons. Moreover, in reaction formulas, Me is methyl, n-Bu is n-butyl, Et is ethyl and Py is pyridine, but each of the symbols is one example and a reagent used for each reaction is not limited thereto.

In each step described below, a reaction is preferably performed in a solution state. As the solvent, for example, at least one kind of organic solvent selected from the group of a nitrile-based solvent such as acetonitrile; a halogenated solvent such as dichloromethane, chloroform, chlorobenzene and dichlorobenzene; an ether-based solvent such as tetrahydrofuran; and an aromatic hydrocarbon solvent such as toluene is preferably used. Moreover, upon adding an organometallic compound to a solution of compound (11) or (21), the organometallic compound is preferably added in the form of a solution of an organic solvent such as hexane.

Moreover, the resulting compound (crude product) may be appropriately purified in each inter-step. Specific examples of a purification method include a method by column chromatography or recrystallization.

Step 1A (Homocoupling)

In step 1A, compound (11) or compound (21) is subjected to homocoupling in the presence of an organometallic compound. Reaction temperature (example: solution temperature) in step 1A is ordinarily 0 to 60° C., and preferably, 0° C. to room temperature; reaction time is ordinarily 2 to 14 hours; and the reaction is ordinarily performed under normal pressure. In addition, "room temperature" means a temperature environment of about 23° C.

Specific examples of the organometallic compound include n-butyllithium and s-butyllithium, and may be used alone in one kind or in combination of two or more kinds. An amount of using the organometallic compound is ordinarily 1.05 to 2.10 mol based on 1 mol of compound (11) or (21).

Step 2A (Deprotection)

In step 2A, methoxy of compound (12) or (22) is subjected to deprotection in the presence of a deprotecting agent. Reaction temperature (example: solution temperature) in step 2A is ordinarily −78° C. to room temperature, and preferably, 0° C. to room temperature; reaction time is ordinarily 1 to 2 hours; and the reaction is ordinarily performed under normal pressure.

Specific examples of the deprotecting agent include boron tribromide and aluminum chloride, and may be used alone in one kind or in combination of two or more kinds. An amount of using the deprotecting agent is ordinarily 2.0 to 2.4 mol based on 1 mol of compound (12) or (22).

Step 3A

In step 3A, compound (13) or (23) is allowed to react with N,N-dialkyl thiocarbamoyl chloride or N,N-dialkyl selenocarbamoyl chloride in the presence of abase. Reaction temperature (example: solution heating temperature) in step 3A is ordinarily 60 to 80° C.; reaction time is ordinarily 10 to 48 hours; and the reaction is ordinarily performed under normal pressure.

The number of carbon atoms in both of alkyl in N,N-dialkyl thiocarbamoyl chloride and N,N-dialkyl selenocarbamoyl chloride is each independently 1 to 3, and preferably, 1 to 2.

Specific examples of N,N-dialkyl thiocarbamoyl chloride include N,N-dimethyl thiocarbamoyl chloride and N,N-diethyl thiocarbamoyl chloride. Specific examples of N,N-dialkyl selenocarbamoyl chloride include N,N-dimethyl selenocarbamoyl chloride and N,N-diethyl selenocarbamoyl chloride. An amount of using N,N-dialkyl thiocarbamoyl chloride or N,N-dialkyl selenocarbamoyl chloride is ordinarily 3.0 to 4.0 mol based on 1 mol of compound (13) or (23).

Specific examples of the base include triethylamine, pyridine and sodium hydride, and may be used alone in one kind or in combination of two or more kinds. An amount of using the base is ordinarily 1.1 to 5.0 mol of triethylamine, and preferably, 1.5 to 2.5 mol thereof, ordinarily, 5 to 30 mol of pyridine, and preferably, 10 to 20 mol thereof, based on 1 mol of compound (13) or (23).

Step 4A (Cyclization)

In step 4A, compound (14) or (24) is subjected to heating and cyclization to obtain compound (15) or (25) as the compound of the invention. Heating temperature in step 4A is ordinarily 300 to 310° C.; and reaction time is ordinarily 4 to 6 hours.

Step 3A' (Dehydration Cyclization)

In step 3A', zeolite is added to the solution of compound (13) or (23), and the compound is subjected to dehydration cyclization to obtain compound (15) or (26) as the compound of the invention. Heating temperature (example: solution heating temperature) in step 3A' is ordinarily 160 to 180° C.; reaction time is ordinarily 8 to 20 hours, and preferably, 10 to 16 hours; and a reaction is performed under normal pressure.

In addition to the manufacturing methods described above, compound (2-1) of the invention can be manufactured by brominating an unsubstituted compound synthesized by a publicly-known method and represented by formula (27), and subsequently introducing a desired substituent on a position of a bromine moiety by a publicly-known cross-coupling reaction. A method for introducing the desired substituent thereon by the cross-coupling reaction is particularly useful for synthesis of a disubstituted form.

Specifically, a method for manufacturing compound (2-1) according to the invention comprises: step 1B for brominating the compound represented by formula (27) to obtain a compound represented by formula (28); and step 2B for allowing the compound represented by formula (28) to react with a cross-coupling reactant (by performing the cross-coupling reaction) to obtain a compound represented by formula (29). See FIG. 7.

Figure 7:
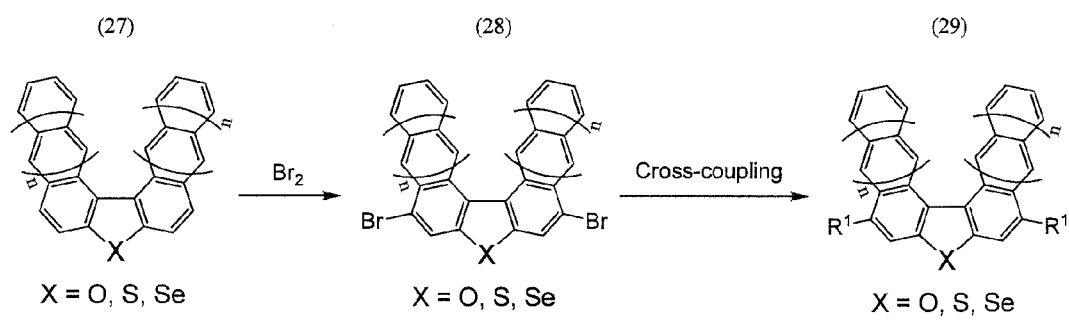
FIG. 7 shows the reaction scheme for producing a compound of formula (29).

In formulas (27) to (29) of FIG. 7, X, n and $R^1$ each are defined in a manner identical with the definitions of an identical symbol in formula (2-1).

Step 1B (Bromination)

In step 1B, bromination is performed on 5-position and 9-position (in the case of n=0), or 6-position and 10-position (in the case of n=1) of compound (27). An amount of using bromine is ordinarily 2.0 to 2.2 mol based on 1 mol of compound (27).

Heating temperature in step 1B (example: solution or suspension heating temperature) is ordinarily room temperature to 100° C., and preferably, 80 to 100° C.; reaction time is ordinarily 4 to 10 hours, and preferably, 4 to 8 hours; and the reaction is ordinarily performed under normal pressure.

In step 1B, compound (27) is preferably subjected to bromination in a solution or suspension state. As a solvent, for example, at least one kind of organic solvent selected from the group of acetic acid and chloroform is preferably used.

Moreover, the resulting compound (crude product) may be appropriately purified between step 1B and step 2B. Specific examples of a purification method include a method by column chromatography or recrystallization.

Compound (28), namely, a compound represented by formula (2-1') is preferred as a raw material compound used for synthesis of compound (29), namely, a compound represented by formula (2-1).

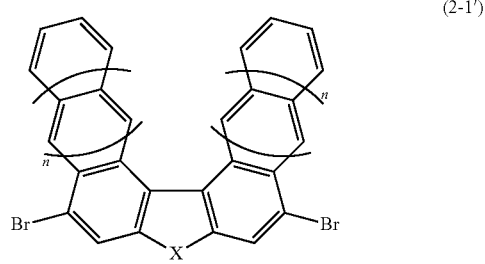

(2-1')

In formula (2-1'), X is oxygen, sulfur or selenium; and both of n are each independently 0 or 1.

Step 2B (Cross-Coupling)

In step 2B, a bromine moiety of compound (28) is converted into substituent $R^1$ by a publicly-known cross-coupling reaction, for example, a Suzuki coupling reaction, a Stille coupling reaction, a Negishi coupling reaction, a Tamao coupling reaction, and a reaction derived therefrom. $R^1$ is defined in a manner identical with the definition of an identical symbol in formula (2-1).

In step 2B, cross coupling of compound (28) is preferably performed in a solution or suspension state. As a solvent, although the solvent is different depending on a cross-coupling reaction form, for example, at least one kind of organic solvent selected from the group of N,N-dimethylformamide, tetrahydrofuran, toluene and diethyl ether is preferably used.

A cross-coupling reactant (compound for introducing substituent $R^1$ thereon) used for the cross-coupling reaction, a catalyst therefor and reaction conditions (examples: temperature and time) are different depending on the cross-coupling reaction form, and are not particularly limited.

Specific examples are presented below.

Specific examples of the cross-coupling reactant include: $R^1$—$SnR_3$ (wherein, $R^1$ is thienyl, furyl or thiazolyl, and R is alkyl such as butyl) such as tributyl(2-thienyl)tin, tributyl (2-furyl)tin and tributyl(2-thiazolyl)tin; $R^1$—MgX (wherein, $R^1$ is alkyl having 1 to 20 carbons, aryl having 6 to 14 carbons or pyridyl, and X is halogen such as bromine); $R^1$—$B(OH)_2$ (wherein, $R^1$ is aryl having 6 to 14 carbons or pyridyl); and $R^1$—ZnX (wherein, $R^1$ is aryl having 6 to 14 carbons or pyridyl). An amount of using the cross-coupling reactant is ordinarily 1.1 to 4.0 mol, and preferably, 2.0 to 3.0 mol, based on 1 mol of compound (28).

Specific examples of the catalyst include a palladium catalyst such as tetrakis(triphenylphosphine)palladium(0), a 1,1'-bis(diphenylphosphino)ferrocene palladium(II) dichloride-dichloromethane complex and a tris(dibenzylideneacetone)dipalladium(0)-chloroform complex, and a nickel catalyst such as [1,3-bis(diphenylphosphino)propane]nickel (II) dichloride.

Reaction temperature (example: solution or suspension temperature) in step 2B is ordinarily 0 to 140° C., and preferably, room temperature to 140° C.; reaction time is ordinarily 10 minutes to 24 hours, and preferably, 1 to 24 hours; and the reaction is ordinarily performed under normal pressure. The reaction temperature is different depending on a type of coupling, and for example, 80 to 140° C. in Stille coupling, 0° C. to room temperature in Tamao coupling, and 80 to 110° C. in Suzuki coupling.

Compound (1) (X=selenium) of the invention can also be manufactured by a method described below. Specifically, the method comprises: step 1A described above; step 2A described above; step 5A for allowing the compound represented by formula (13) to react with trifluoromethanesulfonyl chloride or trifluoromethanesulfonic anhydride to obtain a compound represented by formula (16); step 6A for allowing coupling of the compounds represented by formula (16) with boranes to obtain boronic ester represented by formula (17); step 7A for brominating the boronic ester represented by formula (17) with copper bromide to obtain a compound represented by formula (18); and step 8A for lithiating the compound represented by formula (18) and then allowing the resulting product to react with selenium chloride to obtain a compound represented by formula (15).

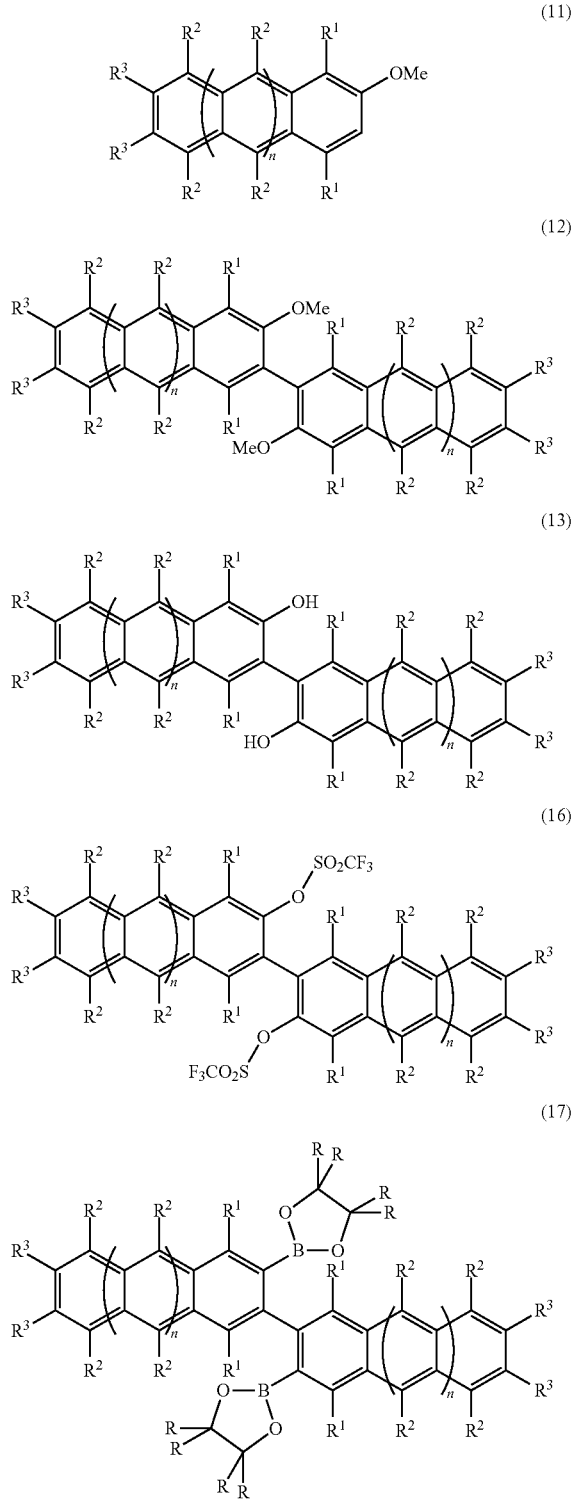
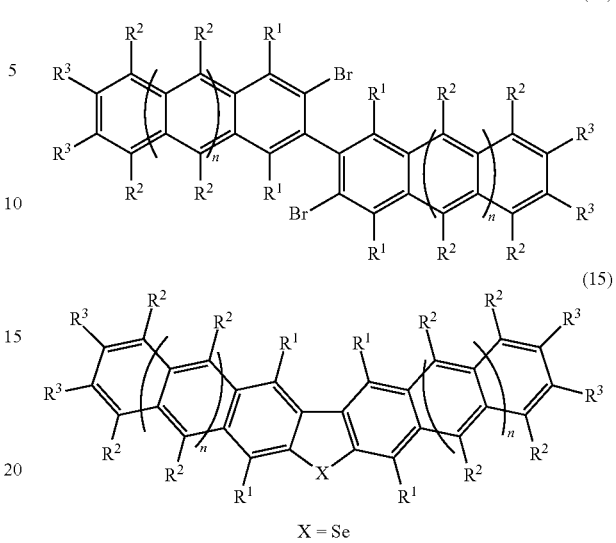

In formulas (11) to (13) and formulas (15) to (18), X is selenium, n and $R^1$ to $R^3$ each are defined in a manner identical with the definitions of an identical symbol in formula (1), Me is methyl, and in formula (17), R's are each independently alkyl having 1 to 3 carbons.

In individual steps 5A to 8A described below, a reaction is preferably performed in a solution state. As a solvent, for example, at least one kind of organic solvent selected from the group of a pyrrolidone-based solvent such as N-methyl-2-pyrrolidone; a halogenated solvent such as dichloromethane, chloroform, chlorobenzene and dichlorobenzene; an ether-based solvent such as tetrahydrofuran and 1,4-dioxane; and an alcoholic solvent such as methanol is preferably used.

Step 5A

In step 5A, compound (13) is allowed to react with trifluoromethanesulfonyl chloride or trifluoromethanesulfonic anhydride to obtain compound (16). Reaction temperature (example: solution temperature) in step 5A is ordinarily 0 to 30° C.; and reaction time is ordinarily 2 to 24 hours.

An amount of using trifluoromethanesulfonyl chloride or trifluoromethanesulfonic anhydride is ordinarily 2.0 to 5.0 mol based on 1 mol of compound (13).

Step 5A can be applied in the presence of a base. Specific examples of the base include pyridine, triethylamine and N,N-dimethyl-4-aminopyridine, and may be used alone in one kind or in combination of two or more kinds. An amount of using the base is ordinarily 0.1 to 10.0 mol based on 1 mol of compound (13).

Step 6A

In step 6A, compound (16) is subjected to coupling with boranes to obtain boronic ester (17). Reaction temperature (example: solution temperature) in step 6A is ordinarily 20 to 150° C.; and reaction time is ordinarily 3 to 24 hours.

Specific examples of the boranes include a compound represented by a formula described below, specifically, 4,4,5,5-tetramethyl-1,3,2-dioxaborolane. An amount of using the boranes is ordinarily 2.0 to 5.0 mol based on 1 mol of compound (16).

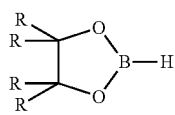

wherein, R's are each independently alkyl having 1 to 3 carbons.

In the reaction thereof, a catalyst can be used. Specific examples of the catalyst include a palladium catalyst such as tetrakis(triphenylphosphine)palladium(0), a 1,1'-bis(diphenylphosphino)ferrocene palladium(II) dichloride-dichloromethane complex and a tris(dibenzylideneacetone)dipalladium(0)-chloroform complex, and a nickel catalyst such as [1,3-bis(diphenylphosphino)propane]nickel(II) dichloride.

Step 6A can be applied in the presence of a base. Specific examples of the base include triethylamine. An amount of using the base is ordinarily 2.0 to 10.0 mol based on 1 mol of compound (16).

Step 7A

In step 7A, boronic ester (17) is subjected to bromination with copper bromide to obtain compound (18). Reaction temperature (example: solution temperature) in step 7A is ordinarily 0 to 200° C.; and reaction time is ordinarily 6 to 30 hours. An amount of using the copper bromide is ordinarily 2.0 to 10.0 mol based on 1 mol of boronic ester (17).

Step 8A

In step 8A, compound (18) is subjected to lithiation, and then allowed to react with selenium chloride to obtain compound (15). Reaction temperature (example: solution temperature) in step 8A is ordinarily −80 to 30° C.; and reaction time is ordinarily 1 to 5 hours.

Specific examples of the lithiating agent include t-butyllithium. An amount of using the lithiating agent is ordinarily 2.0 to 5.0 mol based on 1 mol of compound (18). An amount of using the selenium chloride is ordinarily 1.0 to 1.5 mol based on 1 mol of compound (18).

In the method for manufacturing the compound according to the invention described above, the compound of the invention shows high solubility in a solvent, and therefore a crude product of the compound after synthesis can be simply purified by a simple method such as column chromatography and recrystallization.

Film Such as an Organic Semiconductor Film

A film (example: organic semiconductor film) of the invention includes at least one kind selected from the compound of the invention, namely, compound (1) and compound (2). The compound of the invention shows high solubility in a solvent, and therefore a solution in which the compounds are dissolved into the solvent (hereinafter, also referred to as "organic semiconductor solution") is applied onto a substrate to allow formation of a film (example: organic semiconductor film) having excellent surface uniformity.

Specific examples of the solvent used for preparation of the organic semiconductor solution include an organic solvent such as pentane, hexane, heptane, diethyl ether, t-butyl methyl ether, tetrahydrofuran, methanol, ethanol, isopropanol, ethyl acetate, ethyl lactate, dioxane, benzene, toluene, xylene, dichloromethane, chloroform, 1,2-dichloroethane, dichlorobenzene, acetonitrile, acetone, cyclohexane, cyclopentanone, cyclohexanone, γ-butyrolactone, butyl cellosolve, N-methyl-2-pyrrolidone, N,N-dimethylformamide (DMF) and dimethyl sulfoxide; water; or a mixture of two or more kinds thereof.

A concentration of the compound according to the invention in the organic semiconductor solution is preferably 0.05 to 10% by mass, and further preferably, 0.1 to 5% by mass. The compound of the invention shows high solubility in a solvent, and therefore a high-concentration solution thereof can be prepared. "High-concentration solution of the compound of the invention" herein means a solution having a concentration of 0.1% by mass or more of the compound in the organic semiconductor solution.

An organic semiconductor solution having various concentrations can be prepared by excellent solubility of the compound of the invention in the solvent, and therefore a degree of crystallinity of a film to be obtained can be changed. When the degree of crystallinity of the film is changed, the carrier mobility influenced by the degree of crystallinity is also changed. Therefore, in the invention, crystallinity in a wide range from a crystal to amorphousness can be easily adjusted, and required device characteristics such as a thickness of the organic semiconductor film and the carrier mobility can be stably reproduced.

Moreover, a film may be formed using a resin composition containing the compound and a polymer compound according to the invention. A content of the polymer compound in the resin composition is ordinarily 1 to 99% by mass, preferably, 5 to 90% by mass, and further preferably, 5 to 80% by mass. Moreover, a content of the solvent in the resin composition is appropriately set up so as for a content of the compound and the polymer compound according to the invention to be in the range described above, and for the resin composition to have viscosity suitable for film formation.

Specific examples of the polymer compound include a thermoplastic polymer and a thermosetting polymer. Specific examples include polyester, polyamide, polystyrene, polymethacrylic acid, polyacrylic acid, polyethylene, polypropylene, polycycloolefin, polyvinyl chloride, polyvinylidene chloride, polyvinyl acetate, polycarbonate, a phenolic resin, a polyurethane resin, an epoxy resin, a melamine resin, polytetrafluoroethylene, polyacetylene, polypyrrole, and polyallylene vinylene. Moreover, as the polymer compound, a conductive polymer may be used. Specific examples of the conductive polymer include polythiophene, polypyrrole and polyaniline.

A thickness of the film of the invention can be appropriately selected according to a desired use. For example, a thickness of the organic semiconductor film used for the organic semiconductor device is preferably 10 to 1,000 nanometers, and further preferably, 10 to 200 nanometers.

Specific examples of the method for manufacturing the film according to the invention include various methods.

Specific examples of the application process include a spin coating process, a dip coating process and a blade process. Moreover, the edge-cast process and the gap-cast process as developed by the present inventors, and classified into the application process as described later in Examples are also effective.

Specific examples of the printing process include screen printing, inkjet printing, lithography, intaglio printing and letterpress printing. Among the printing processes, inkjet printing to be performed by a printer in which the solution of the compound of the invention is directly used as ink is a simple method, and therefore preferred.

Film formation is allowable applying a film-forming method other than the methods described above, for example, the vapor deposition process.

Temperature during the film formation is not particularly limited. The temperature is ordinarily room temperature to 200° C., and preferably, 50 to 150° C. The temperature herein refers to temperature for heating the organic semiconductor solution in the application process or the printing process, for example, atmosphere temperature or temperature for heating the substrate used for film formation. Moreover, the solution temperature, the atmosphere temperature or the substrate temperature may be different with each other. In the film-forming method without using the solution, for example, in the vapor deposition process, the temperature means temperature for heating the substrate used for film formation.

When the organic semiconductor film is directly used as a part of the organic semiconductor device, patterning is preferably performed by the printing process, and further in the printing process, the high-concentration solution of the compound according to the invention is preferably used. If the high-concentration solution is used, inkjet printing, mask printing, screen printing, offset printing and so forth can be utilized. Moreover, manufacture of the organic semiconductor film by the printing process can be made by an assembly-line operation without needing a heating or vacuum process, and therefore contributes to cost reduction and an increase in responsiveness to a process change. Moreover, manufacture of the organic semiconductor film by the printing process contributes to simplification of a circuit in the device, an improvement in manufacturing efficiency, and cost reduction and weight reduction of the device. From the viewpoints described above, the compound showing the high solubility in the solvent according to the invention is excellent.

Organic Semiconductor Device

An organic semiconductor device of the invention has the organic semiconductor film and electrodes. Specifically, the organic semiconductor device can be formed by combining the organic semiconductor film and any other device having semiconductor characteristics. Specific examples of other devices having semiconductor characteristics include a rectifying device, a thyristor for performing switching action, TRIAC and DIAC.

The organic semiconductor device of the invention can also be used as a display device, and the display device in which all members are constituted of an organic compound is particularly useful.

Specific examples of the display device include a flexible sheet-shaped display device (examples: electronic paper, IC card tag), a liquid crystal display device and an electroluminescence (EL) device. The display devices can be prepared by forming, on an insulating substrate formed of a polymer and showing flexibility, the organic semiconductor film of the invention and at least one layer including a constituent for allowing function of the film. The display device prepared by such a method has flexibility, and therefore can be carried by putting the device into a pocket of clothes, a purse or the like.

Specific examples of the display device also include a proper identification code response system. The proper identification code response system reacts with electromagnetic waves having a specific frequency or a specific code, and responds to electromagnetic waves including a proper identification code. The proper identification code response system is used as a means for identifying a document or a person in a reusable passenger ticket or a membership card, a means of payment and settlement, a seal for identification of a parcel or merchandise, a role of a label or stamp, company or administrative services, or the like.

The proper identification code response system has, on a glass substrate or an insulating substrate formed of the polymer and showing flexibility, an aerial for receiving a signal in synchronizing with the signal, and the organic semiconductor device that operates with received electric power and sends an identification signal according to the invention.

Organic Field Effect Transistor (FET)

Specific examples of the organic semiconductor device of the invention include an organic field effect transistor (FET). The organic FET of the invention can also be used in combination with the liquid crystal display device and the electroluminescence (EL) device.

The organic FET of the invention has a substrate, a gate electrode, a gate insulating film, a source electrode, a drain electrode and an organic semiconductor layer, and the organic semiconductor layer is formed of the organic semiconductor film according to the invention. Moreover, the organic FET of the invention may have a carrier injection layer in order to improve carrier injection efficiency.

In the organic FET, a carrier is induced on an interface of the organic semiconductor layer on the gate insulating film by controlling voltage applied to the gate electrode, and an electric current flowing through the source electrode and the drain electrode is controlled, thereby performing the switching action.

In the organic FET, the carrier mobility can be determined from a drain current-gate voltage curve obtained by measuring an electric current between the source electrode and the drain electrode while changing a drain voltage and a gate voltage. Furthermore, ON-OFF action of the drain current by the gate voltage can also be observed.

In general, structure of the organic FET is broadly classified into bottom gate type structure and top gate type structure, and each structure is further classified into top contact structure and bottom contact structure.

AS the organic FET, an embodiment in which the gate electrode is formed on the substrate, and the gate insulating film and the organic semiconductor layer are further formed in the order is referred to as the bottom gate type structure; and structure in which the organic semiconductor layer, the gate insulating film and the gate electrode are formed on the substrate in the order is referred to as the top gate type structure.

Moreover, as the organic FET, an embodiment in which the source electrode and the drain electrode are arranged on a lower part of the organic semiconductor layer (on substrate side) is referred to as a bottom contact type FET; and an embodiment in which the source electrode and the drain electrode are arranged on an upper part of the organic semiconductor layer (on side opposite to substrate by interposing organic semiconductor layer) is referred to as a top contact type FET. From a viewpoint of carrier injection between the source electrode and the organic semiconductor layer and between the drain electrode and the organic semiconductor layer, the top contact type structure is superior in organic FET characteristics to the bottom contact type structure in many cases.

FIG. 1 shows a cross-sectional view of an organic FET having each of a bottom gate-top contact type (a), a bottom gate-bottom contact type (b), a top gate-top contact type (c) and a top gate-bottom contact type (d). However, the organic FET of the invention is not limited to the structure of the organic FET described above, but may have publicly known organic FET structure. Moreover, the organic FET of the invention may also adopt vertical organic FET structure.

Specific examples of the substrate include various substrates. Specific examples include a glass substrate, a metal substrate such as gold, copper and silver substrates, a crystalline silicon substrate, an amorphous silicon substrate, a triacetyl cellulose substrate, a norbornene substrate, a polyester substrate such as a polyethylene terephthalate substrate, a polyvinyl chloride substrate, a polypropylene substrate and a polyethylene substrate.

Specific examples of materials of the gate electrode include an inorganic material such as Al, Ta, Mo, Nb, Cu, Ag, Au, Pt, In, Ni, Nd, Cr, silicon including polysilicon, amorphous silicon and highly doped silicon, tin oxide, indium oxide and an indium tin compound (indium tin oxide: ITO); and an organic material such as a conductive polymer. However, the conductive polymer may be treated so as to improve conductivity by addition of impurities.

Specific examples of materials of the gate insulating film include an inorganic material such as $SiO_2$, SiN, $Al_2O_3$ and $Ta_2O_5$; and a polymer material such as polyimide and polycarbonate.

A surface of the gate insulating film and the substrate can be subjected to surface treatment using a publicly known silane coupling agent, for example, a silane coupling agent having an alkyl group, such as hexamethyldisilazane (HMDS), octadecyltrichlorosilane (OTS), decyltriethoxysilane (DTS) and octadecyltriethoxysilane (ODSE), or a silane coupling agent having a fluoroalkyl group, such as triethoxytridecafluorooctylsilane (F-SAM). If the surface is subjected to suitable surface treatment using HMDS, OTS, DTS, ODSE, F-SAM or the like, an increase in a grain diameter of crystal constituting an organic FET layer, an improvement of crystallinity, an improvement of molecular orientation or the like is generally observed. As a result, the carrier mobility and the ON-OFF ratio are improved, and a threshold voltage tends to decrease.

As materials of the source electrode and the drain electrode, materials of a kind same with the materials of the gate electrode can be used, and may be identical with or different from the materials of the gate electrode, or different kinds of materials may be laminated.

The carrier injection layer is arranged, as required, in the form of contact with any of the source electrode, the drain electrode and the organic semiconductor layer in order to improve the carrier injection efficiency. A film of the carrier injection layer is formed by using tetrafluorotetracyanoquinodimethane (F4TCNQ), hexaazatriphenylenehexacarbonitrile (HAT-CN), molybdenum oxide or the like.

EXAMPLES

The invention will be more specifically described by way of Examples below, but the invention is in no way limited to the Examples. A method for measuring physical properties a synthetic compound is as described below.

A melting point was measured using Toledo MP70 Automatic Melting-Point System made by Mettler-Toledo International Inc.

A $^1$H-NMR spectrum and a $^{13}$C-NMR spectrum were measured using ECA-600 and ECS400 Spectrometer made by JEOL Ltd.

JM10 MICRO CORDER made by J-SCIENCE LAB Co., Ltd. was used for an elemental analysis.

JMS-T100LC APCI/ESI Mass Spectrometer made by JEOL Ltd. and ultraflex III TOF/TOF made by Bruker Daltonics Inc. were used for a mass analysis.

In addition, in each title compound in Examples described below, all of alkyl are a straight-chain group.

Example 1

Synthesis of 2,10-didecyldinaphtho[2,3-b:2',3'-d]furan

First Step

Synthesis of 7,7'-didecyl-3,3'-dimethoxy-2,2'-binaphthalene

Figure 10:
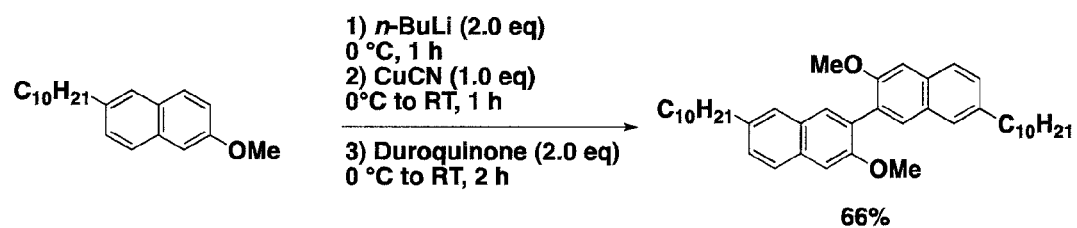
FIG. 10 shows the reaction scheme for producing 7,7'-didecyl-3,3'-dimethoxy-2,2'-binaphthalene.

To a tetrahydrofuran solution (153 mL) of 2-decyl-6-methoxynaphthalene (11.4 g, 38.1 mmol), n-butyllithium (1.62 M hexane solution, 47 mL, 76.14 mmol) was added dropwise at 0° C. at a rate of 10 mL per minute. The resulting mixture was stirred at 0° C. for 1 hour, and then copper cyanide (3.43 g, 38.3 mmol) was added thereto. Temperature was returned to room temperature, the resulting mixture was stirred for 1 hour, and then tetramethyl benzoquinone (duroquinone; 12.5 g, 76.3 mmol) was added thereto at 0° C. Temperature was returned to room temperature, the resulting mixture was stirred for 2 hours, and then neutralized by adding 1N hydrochloric acid thereto. An organic layer was extracted with ethyl acetate, and then dried over magnesium sulfate. After removing a desiccant, a solution thereof was concentrated under reduced pressure by a rotary evaporator. The resulting crude product was purified by silica gel column chromatography using as an eluent a mixed solvent of hexane and chloroform (hexane: chloroform=7:3 (volume ratio)) to obtain a white solid title compound (7.47 g, 12.6 mmol, 66%). See FIG. 10.

Melting point: 65.5 to 66.5° C. $^1$H NMR (400 MHz, $CD_3Cl$): δ 0.88 (t, J=6.8 Hz, 6H, $CH_3$), 1.26-1.35 (m, 28H, $(CH_2)_3$), 1.69 (quin, J=6.8 Hz, 4H, $ArCH_2CH_2$), 2.74 (t, J=7.6 Hz, 4H, $ArCH_2$), 3.86 (s, 6H, $OCH_3$), 7.19 (s, 2H, ArH), 7.30 (d, J=8.4 Hz, 2H, ArH), 7.55 (s, 2H, ArH), 7.68 (s, 2H, ArH), 7.70 (d, J=8.4 Hz, 2H, ArH). $^{13}$C NMR (150 MHz, $CDCl_3$): δ 14.3, 22.9, 29.48, 29.51, 29.7, 29.80 (two carbons), 31.7, 32.1, 36.1, 55.8, 105.3, 126.3, 126.4, 127.9, 129.0, 129.9, 130.1, 132.8, 138.3, 155.9. TOF HRMS (APCI): Calcd for $C_{42}H_{59}O_2$ [M+H] 595.4515. found, 595.4509. Anal. Calcd for $C_{42}H_{58}O_2$: C, 84.79; H, 9.83. Found: C, 84.73; H, 9.56.

Second Step

Synthesis of 7,7'-didecyl-2,2'-binaphthalene-3,3'-diol

Figure 11:
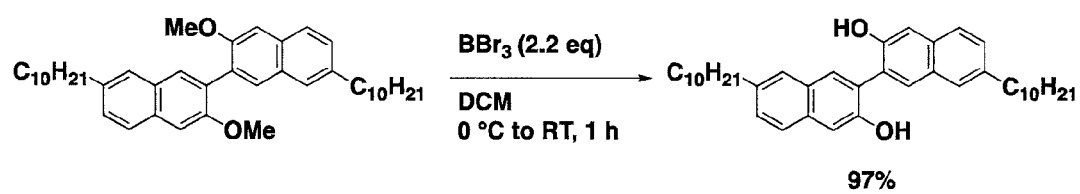
FIG. 11 shows the reaction scheme for producing 7,7'-didecyl-2,2'-binaphthalene-3,3'-diol.

To a dichloromethane solution (DCM; 10 mL) of 7,7'-didecyl-3,3'-dimethoxy-2,2'-binaphthalene (1.49 g, 2.50 mmol), boron tribromide (1.0 M dichloromethane solution, 5.50 mL, 5.50 mmol) was added dropwise at 0° C. at a rate of 2 mL per minute. Temperature was returned to room temperature, the resulting mixture was stirred for 1 hour, and then a reaction solution was added to ice water. An organic layer was extracted with ethyl acetate, and then washed with brine and dried over magnesium sulfate. After removing a desiccant, a solution thereof was concentrated under reduced pressure by a rotary evaporator. The resulting crude product was purified by silica gel column chromatography using a mixed solvent of hexane and ethyl acetate (hexane:ethyl acetate=8:2 (volume ratio)) as an eluent to obtain a white solid title compound (1.38 g, 2.43 mmol, 97%). See FIG. 11.

Melting point: 108.5 to 109.5° C. $^1$H NMR (400 MHz, CD$_3$Cl): δ 0.88 (t, J=6.4 Hz, 6H, CH$_3$), 1.26-1.35 (m, 28H), 1.72 (m, 4H), 2.76 (t, J=7.6 Hz, 4H, ArCH$_2$), 5.63 (s, 2H, OH), 7.34 (d, J=8.4 Hz, 2H, ArH), 7.39 (s, 2H, ArH), 7.58 (s, 2H, ArH), 7.69 (d, J=8.4 Hz, 2H, ArH), 7.79 (s, 2H, ArH).

Third Step

Synthesis of 2,10-didecyldinaphtho[2,3-b:2',3'-d]furan

Figure 12:
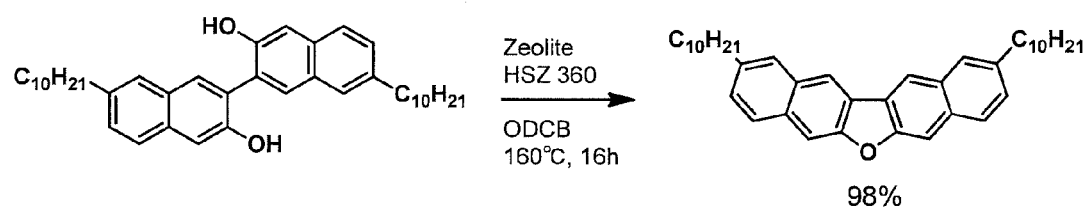
FIG. 12 shows the reaction scheme for producing 2,10-didecyldinaphtho[2,3-b:2',3'-d]furan.

To an o-dichlorobenzene solution (ODCB; 42 mL) of 7,7'-didecyl-2,2'-binaphthalene-3,3'-diol (1.19 g, 2.10 mmol), zeolite Tosoh HSZ-360HUA (357 mg) was added, and the resulting mixture was stirred at 160° C. for 16 hours. Temperature was returned to room temperature, the resulting mixture was subjected to Celite filtration, and zeolite was filtered off. A solution thereof was concentrated under reduced pressure by a rotary evaporator. The resulting crude product was purified by silica gel column chromatography using a mixed solvent of hexane and dichloromethane (hexane:dichloromethane=8:2 (volume ratio)) as an eluent to obtain a white solid title compound (1.13 g, 2.06 mmol, 98%). See FIG. 12.

Melting point: 175 to 176° C. $^1$H NMR (400 MHz, CD$_3$Cl): δ 0.89 (t, J=6.4 Hz, 6H, CH$_3$), 1.26-1.40 (m, 28H, (CH$_2$)$_3$), 1.75 (quin, J=6.8 Hz, 4H, ArCH$_2$CH$_2$), 2.82 (t, J=7.2 Hz, 4H, ArCH$_2$), 7.40 (d, J=8.4 Hz, 2H, ArH), 7.81 (s, 2H, ArH), 7.83 (s, 2H, ArH), 7.88 (d, J=8.4 Hz, 2H, ArH), 8.43 (s, 2H, ArH). $^{13}$C NMR (150 MHz, CDCl$_2$CDCl$_2$): δ 14.4, 22.9, 29.5, 29.6, 29.70, 29.77, 29.79, 31.5, 32.0, 36.1, 106.5, 119.6, 125.1, 126.8, 127.6, 128.3, 130.3, 132.0, 139.3, 155.4. TOF HRMS (APCI): Calcd for C$_{40}$H$_{53}$O [M+H] 549.4096. Found 549.4093. Anal. Calcd for C$_{40}$H$_{52}$O: C, 87.37; H, 9.72. Found: C, 87.61; H, 9.50.

Example 2

Synthesis of 2,10-didecyldinaphtho[2,3-b:2',3'-d]thiophene

First Step

Synthesis of O,O'-(7,7'-didecyl-2,2'-binaphthalene-3,3'-diyl)bis(dimethylcarbamothioate)

Figure 13:
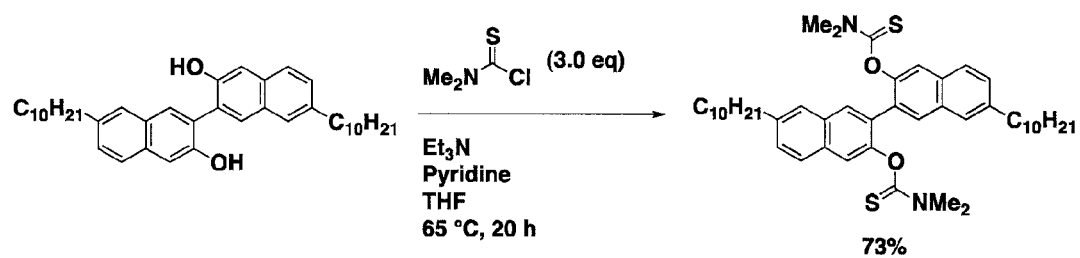
FIG. 13 shows the reaction scheme for producing O,O'-(7,7'-didecyl-2,2'-binaphthalene-3,3'-diyl)bis(dimethylcarbamothioate).

To a tetrahydrofuran solution (THF; 21 mL) of 7,7'-didecyl-2,2'-binaphthalene-3,3'-diol (2.0 g, 3.5 mmol), triethylamine (1.1 mL), pyridine (2.8 mL) and N,N-dimethylthiocarbamoyl chloride (1.38 g, 10.5 mmol) were added, and the resulting mixture was stirred at 65° C. for 20 hours. A solution thereof was concentrated under reduced pressure by a rotary evaporator. The resulting crude product was purified by silica gel column chromatography using a mixed solvent of hexane and ethyl acetate (hexane:ethyl acetate=8:2 (volume ratio)) as an eluent to obtain a colorless liquid title compound (1.90 g, 2.57 mmol, 73%). See FIG. 13.

$^1$H NMR (600 MHz, CDCl$_3$): δ 0.88 (t, J=6.0 Hz, 6H, CH$_3$), 1.26-1.35 (m, 28H), 1.68 (m, 4H), 2.76 (t, J=7.8 Hz, 4H, ArCH$_2$), 2.99 (s, 6H, NCH$_3$), 3.15 (s, 6H, NCH$_3$), 7.35 (d, J=7.8 Hz, 2H, ArH), 7.59 (s, 2H, ArH), 7.60 (s, 2H, ArH), 7.77 (d, J=7.8 Hz, 2H, ArH), 7.88 (s, 2H, ArH).

Second Step

Synthesis of 2,10-didecyldinaphtho[2,3-b:2',3'-d]thiophene

Figure 14:
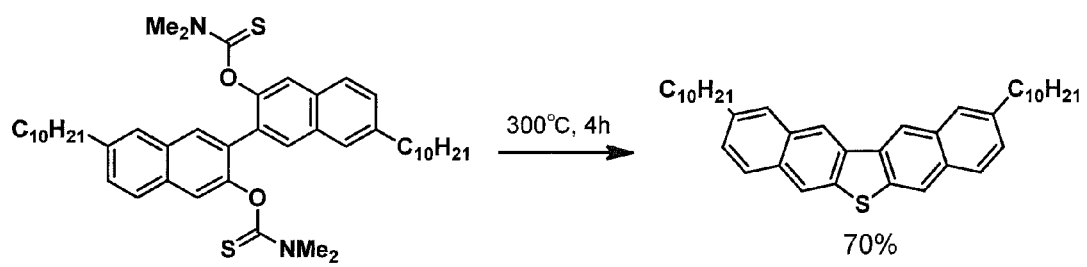
FIG. 14 shows the reaction scheme for producing 2,10-didecyldinaphtho[2,3-b:2',3'-d]thiophene.

Then, O,O'-(7,7'-didecyl-2,2'-binaphthalene-3,3'-diyl)bis(dimethylcarbamothioate) (1.90 g, 2.57 mmol) was sealed into a Pyrex tube, and heated at 300° C. for 4 hours. Temperature was returned to room temperature, and then the resulting mixture was subjected to thermal recrystallization using a mixed solvent of toluene and 2-propanol (toluene:2-propanol=8:2 (volume ratio)) to obtain a pale yellow solid title compound (1.01 g, 1.79 mmol, 70%). See FIG. 14.

Melting point: 122 to 123° C. $^1$H NMR (400 MHz, CD$_3$Cl): δ 0.88 (t, J=7.2 Hz, 6H, CH$_3$), 1.26-1.40 (m, 28H, (CH$_2$)$_3$), 1.75 (quin, J=6.8 Hz, 4H, ArCH$_2$CH$_2$), 2.83 (t, J=7.2 Hz, 4H, ArCH$_2$), 7.39 (d, J=8.0 Hz, 2H, ArH), 7.81 (s, 2H, ArH), 7.82 (d, J=8.0 Hz, 2H, ArH), 8.17 (s, 2H, ArH), 8.64 (s, 2H, ArH). $^{13}$C NMR (150 MHz, CDCl$_3$): δ 14.3, 22.9, 29.52, 29.54, 29.74, 29.81 (two carbons), 31.5, 32.1, 36.3, 120.0, 120.3, 126.8, 126.9, 128.2, 131.3, 131.9, 134.9, 137.3, 140.0. TOF HRMS (APCI): Calcd for C$_{40}$H$_{53}$S [M+H] 565.3868. found 565.3876. Anal. Calcd for C$_{40}$H$_{52}$S: C, 85.05; H, 9.28. Found: C, 85.26; H, 9.30.

Example 3

Synthesis of 3,9-didecyldinaphtho[2,3-b:2',3'-d]furan

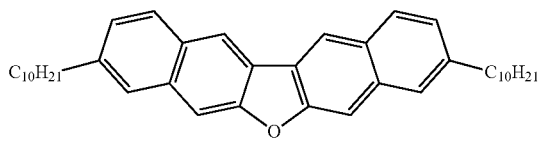

A white solid title compound (yield: 94%) was obtained in accordance with Example 1 except that a starting material was changed to 6,6'-didecyl-3,3'-dimethoxy-2,2'-binaphthalene in Example 1. Values of physical properties are shown below.

Melting point: 216 to 217° C. $^1$H NMR (600 MHz, CDCl$_2$CDCl$_2$): δ 0.82 (t, J=6.6 Hz, 6H, CH$_3$), 1.22-1.36 (m, 28H, (CH$_2$)$_3$), 1.68 (quin, J=7.2 Hz, 4H, ArCH$_2$CH$_2$), 2.75 (t, J=7.2 Hz, 4H, ArCH$_2$), 7.31 (d, J=8.4 Hz, 2H, ArH), 7.67 (s, 2H, ArH), 7.75 (s, 2H, ArH), 7.90 (d, J=8.4 Hz, 2H, ArH), 8.40 (s, 2H, ArH). $^{13}$C NMR (150 MHz, CDCl$_2$CDCl$_2$, 100° C.): δ 14.0, 22.6, 29.3, 29.4, 29.51, 29.59 (two carbons), 31.1, 31.9, 36.2, 106.1, 119.6, 124.6, 126.1, 126.3, 128.3, 128.9, 134.1, 141.2, 156.2. TOF HRMS (APCI): Calcd for C$_{40}$H$_{53}$O [M+H] 549.4096. found 549.4095. Anal. Calcd for C$_{40}$H$_{52}$O: C, 87.37; H, 9.72. Found: C, 87.61; H, 9.50.

Example 4

Synthesis of 3,9-dibutyldinaphtho[2,3-b:2',3'-d]furan

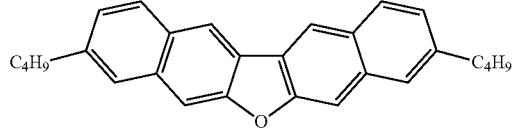

A white solid title compound (yield: 97%) was obtained in accordance with Example 1 except that a starting material was changed to 6,6'-dibutyl-3,3'-dimethoxy-2,2'-binaphthalene in Example 1. Values of physical properties are shown below.

Melting point: 264.0 to 265.0° C. $^1$H NMR (400 MHz, CDCl$_3$): δ 0.98 (t, J=7.2 Hz, 6H, CH$_3$), 1.43 (sext, J=7.2 Hz, 4H, CH$_2$CH$_3$), 1.74 (quin, J=7.2 Hz, 4H, ArCH$_2$CH$_2$), 2.83 (t, J=7.2 Hz, 4H, ArCH$_2$), 7.34 (d, J=8.0 Hz, 2H, ArH), 7.73 (s, 2H, ArH), 7.80 (s, 2H, ArH), 7.95 (d, J=8.0 Hz, 2H, ArH), 8.44 (s, 2H, ArH).

Example 5

Synthesis of 3,9-dihexyldinaphtho[2,3-b:2',3'-d]furan

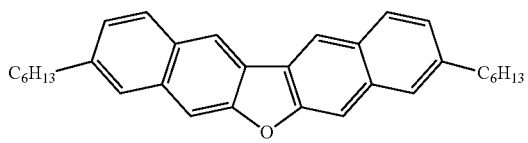

A white solid title compound (yield: 88%) was obtained in accordance with Example 1 except that a starting material was changed to 6,6'-dihexyl-3,3'-dimethoxy-2,2'-binaphthalene in Example 1. Values of physical properties are shown below.

Melting point: 198.7 to 199.1° C. $^1$H NMR (400 MHz, CDCl$_3$): δ 0.91 (t, J=7.2 Hz, 6H, CH$_3$), 1.33-1.43 (m, 12H, (CH$_2$)$_3$), 1.75 (quin, J=7.2 Hz, 4H, ArCH$_2$CH$_2$), 2.82 (t, J=7.2 Hz, 4H, ArCH$_2$), 7.34 (d, J=7.8 Hz, 2H, ArH), 7.73 (s, 2H, ArH), 7.80 (s, 2H, ArH), 7.95 (d, J=7.8 Hz, 2H, ArH), 8.45 (s, 2H, ArH). TOF HRMS (APCI): Calcd for C$_{32}$H$_{37}$O [M+H] 437.2844. found 437.2837. Anal. Calcd for C$_{32}$H$_{36}$O: C, 88.03; H, 8.31. Found: C, 88.06; H, 8.26.

Example 6

Synthesis of 3,9-didecyldinaphtho[2,3-b:2',3'-d]thiophene

First Step

Synthesis of O,O'-(6,6'-didecyl-2,2'-binaphthalene-3,3'-diyl)bis(dimethylcarbamothioate)

Figure 15:
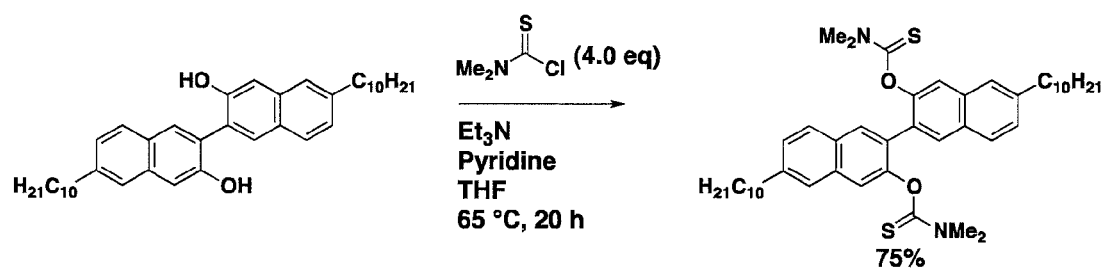
FIG. 15 shows the reaction scheme for producing O,O'-(6,6'-didecyl-2,2'-binaphthalene-3,3'-diyl)bis(dimethylcarbamothioate).

To a tetrahydrofuran solution (10.9 mL) of 6,6'-didecyl-2,2'-binaphthalene-3,3'-diol (1.02 g, 1.80 mmol), triethylamine (0.56 mL), pyridine (1.5 mL) and N,N-dimethylthiocarbamoyl chloride (890 mg, 7.20 mmol) were added, and the resulting mixture was stirred at 65° C. for 20 hours. A solution thereof was concentrated under reduced pressure by a rotary evaporator. The resulting crude product was purified by silica gel column chromatography using a mixed solvent of hexane and ethyl acetate (hexane:ethyl acetate=8:2 (volume ratio)) as an eluent to obtain a colorless liquid title compound (1.00 g, 1.35 mmol, 75%). See FIG. 15.

$^1$H NMR (600 MHz, CDCl$_3$): δ 0.89 (t, J=6.0 Hz, 6H, CH$_3$), 1.26-1.39 (m, 28H, (CH$_2$)$_3$), 1.68 (quin, J=6.8 Hz, 4H, ArCH$_2$CH$_2$), 2.77 (t, J=7.2 Hz, 4H, ArCH$_2$), 3.00 (s, 6H, NCH$_3$), 3.17 (s, 6H, NCH$_3$), 7.32 (d, J=7.8 Hz, 2H, ArH), 7.56 (s, 2H, ArH), 7.61 (s, 2H, ArH), 7.75 (d, J=7.8 Hz, 2H, ArH), 7.90 (s, 2H, ArH). $^{13}$C NMR (150 MHz, CDCl$_3$): δ 14.3, 22.8, 29.47, 29.56, 29.69, 29.73, 29.76, 31.5, 32.0, 36.3, 38.5, 43.2, 120.4, 126.0, 127.6, 127.9, 129.4, 129.9, 131.1, 133.4, 141.4, 149.9 187.4. TOF HRMS (APCI): Calcd for C$_{46}$H$_{65}$N$_2$O$_2$S$_2$ [M+H] 741.4487. Found 741.4487. Anal. Calcd for C$_{46}$H$_{64}$N$_2$O$_2$S$_2$: C, 74.55; H, 8.70; N, 3.78. Found: C, 74.68; H, 8.61; N, 3.70.

Second Step

Synthesis of 3,9-didecyldinaphtho[2,3-b:2',3'-d]thiophene

Figure 16:
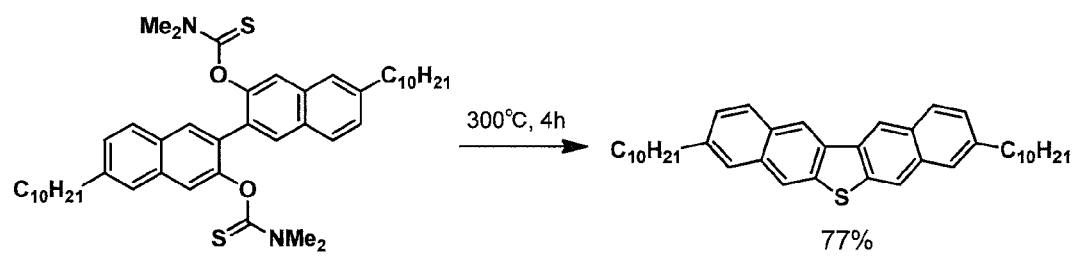
FIG. 16 shows the reaction scheme for producing 3,9-didecyldinaphtho[2,3-b:2',3'-d]thiophene.

Then, O,O'-(6,6'-didecyl-2,2'-binaphthalene-3,3'-diyl)bis(dimethylcarbamothioate) (751 mg, 1.01 mmol) was sealed into a Pyrex tube, and heated at 300° C. for 4 hours. Temperature was returned to room temperature, and then the resulting mixture was purified by silica gel column chromatography using a mixed solvent of hexane and ethyl acetate (hexane:ethyl acetate=95:5 (volume ratio)) as an eluent to obtain a pale yellow solid title compound (440 mg, 0.779 mmol, 77%). See FIG. 16.

Melting point: 182 to 183° C. (TG-DTA). $^1$H NMR (600 MHz, CD$_3$Cl): δ 0.88 (t, J=6.6 Hz, 6H, CH$_3$), 1.26-1.40 (m, 28H, (CH$_2$)$_3$), 1.74 (quin, J=7.8 Hz, 4H, ArCH$_2$CH$_2$), 2.82 (t, J=7.8 Hz, 4H, ArCH$_2$), 7.37 (d, J=8.4 Hz, 2H, ArH), 7.66 (s, 2H, ArH), 7.96 (d, J=8.4 Hz, 2H, ArH), 8.13 (s, 2H, ArH), 8.65 (s, 2H, ArH). $^{13}$C NMR (150 MHz, CDCl$_3$): δ 14.3, 22.9, 29.51, 29.54, 29.73, 29.78, 29.80, 31.5, 32.1, 36.4, 120.0, 120.2, 125.4, 127.2, 128.4, 129.6, 133.5, 134.2, 138.2, 141.2. TOF HRMS (APCI+): Calcd for C$_{40}$H$_{53}$S [M+H] 565.3868. Found 565.3864. Anal. Calcd for C$_{40}$H$_{52}$S: C, 85.05; H, 9.28. Found: C, 84.84; H, 9.31.

Example 7

Synthesis of 3,9-dihexyldinaphtho[2,3-b:2',3'-d]thiophene

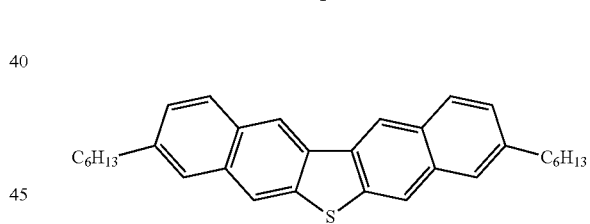

A pale yellow solid title compound (yield: 72%) was obtained in accordance with Example 6 except that decyl of the starting material was changed to hexyl in Example 6. Values of physical properties are shown below.

Melting point: 202.0 to 202.4° C. $^1$H NMR (600 MHz, CDCl$_3$): δ 0.88 (t, J=7.8 Hz, 6H, CH$_3$), 1.27-1.40 (m, 20H, (CH$_2$)$_3$)), 1.74 (quin, J=7.8 Hz, 2H, ArCH$_2$CH$_2$), 2.82 (t, J=7.8 Hz, 4H, ArCH$_2$), 7.38 (d, J=8.4 Hz, 2H, ArH), 7.66 (s, 2H, ArH), 7.96 (d, J=8.6 Hz, 2H, ArH), 8.14 (s, 2H, ArH), 8.65 (s, 2H, ArH). $^{13}$C NMR (150 MHz, CDCl$_3$): δ 14.3, 22.8, 29.2, 31.4, 31.9, 36.4, 120.0, 120.2, 125.4, 127.2, 128.4, 129.7, 133.6, 134.3, 138.3, 141.2. TOF HRMS (APCI+): Calcd for C$_{32}$H$_{37}$S [M+H] 453.2616. found 453.2615. Anal. Calcd for C$_{32}$H$_{36}$S: C, 84.90; H, 8.02. Found: C, 85.09; H, 8.02.

Example 8

Synthesis of 3,9-dioctyldinaphtho[2,3-b:2',3'-d]thiophene

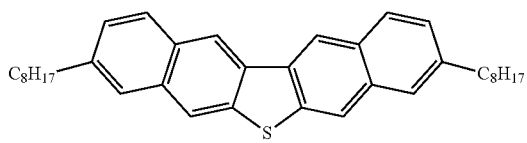

A pale yellow solid title compound (yield: 73%) was obtained in accordance with Example 6 except that decyl of the starting material was changed to octyl in Example 6. Values of physical properties are shown below.

Melting point: 193.7 to 194.8° C. $^1$H NMR (600 MHz, CDCl$_3$): δ 0.88 (t, J=7.2 Hz, 6H, CH$_3$), 1.27-1.38 (m, 20H, (CH$_2$)$_5$), 1.73 (quin, J=7.8 Hz, 2H, ArCH$_2$CH$_2$), 2.81 (t, J=7.8 Hz, 4H, ArCH$_2$), 7.37 (d, J=8.4 Hz, 2H, ArH), 7.66 (s, 2H, ArH), 7.96 (d, J=8.4 Hz, 2H, ArH), 8.13 (s, 2H, ArH), 8.65 (s, 2H, ArH). $^{13}$C NMR (150 MHz, CDCl$_3$): δ 14.1, 22.7, 29.3, 29.4, 29.5, 31.3, 31.9, 36.3, 119.9, 120.0, 125.3, 127.0, 128.2, 129.7, 133.5, 134.2, 138.2, 141.1. TOF HRMS (APCI+): Calcd for C$_{36}$H$_{45}$S [M+H] 509.3242. found 509.3242. Anal. Calcd for C$_{36}$H$_{44}$S: C, 84.98; H, 8.72. Found: C, 85.15; H, 8.69.

Example 9

Synthesis of 3,9-dibutyldinaphtho[2,3-b:2',3'-d]thiophene

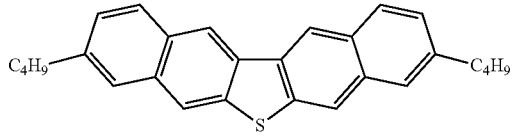

A pale yellow solid title compound (yield: 81%) was obtained in accordance with Example 6 except that decyl of the starting material was changed to butyl in Example 6. Values of physical properties are shown below.

$^1$H NMR (400 MHz, CDCl$_3$): δ 0.97 (t, J=7.2 Hz, 6H, CH$_3$), 1.43 (sext, J=7.2 Hz, 4H, CH$_2$CH$_3$), 1.75 (quin, J=7.2 Hz, 4H, ArCH$_2$CH$_2$), 2.82 (t, J=7.2 Hz, 4H, ArCH$_2$), 7.38 (d, J=8.4 Hz, 2H, ArH), 7.66 (s, 2H, ArH), 7.96 (d, J=8.4 Hz, 2H, ArH), 8.13 (s, 2H, ArH), 8.64 (s, 2H, ArH).

Example 10

Synthesis of 3,9-dipentyldinaphtho[2,3-b:2',3'-d]thiophene

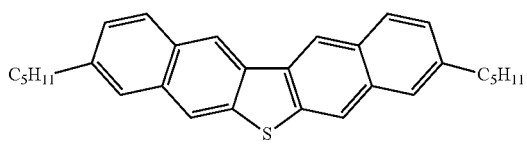

A pale yellow solid title compound (yield: 73%) was obtained in accordance with Example 6 except that decyl of the starting material was changed to pentyl in Example 6. Values of physical properties are shown below.

$^1$H NMR (400 MHz, CDCl$_3$): δ 0.92 (t, J=6.4 Hz, 6H, CH$_3$), 1.37-1.41 (m, 8H, (CH$_2$)$_2$), 1.75 (quin, J=7.6 Hz, 2H, ArCH$_2$CH$_2$), 2.82 (t, J=7.6 Hz, 4H, ArCH$_2$), 7.37 (d, J=8.0 Hz, 2H, ArH), 7.66 (s, 2H, ArH), 7.96 (d, J=8.0 Hz, 2H, ArH), 8.13 (s, 2H, ArH), 8.65 (s, 2H, ArH).

Example 11

Synthesis of 3,9-diheptyldinaphtho[2,3-b:2',3'-d]thiophene

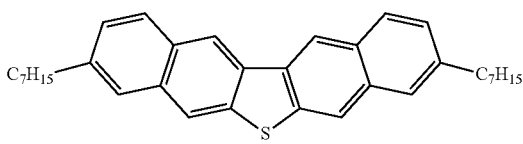

A pale yellow solid title compound (yield: 75%) was obtained in accordance with Example 6 except that decyl of the starting material was changed to heptyl in Example 6. Values of physical properties are shown below.

$^1$H NMR (400 MHz, CDCl$_3$): δ 0.90 (t, J=6.4 Hz, 6H, CH$_3$), 1.27-1.40 (m, 16H, (CH$_2$)$_4$), 1.77 (quin, J=7.2 Hz, 2H, ArCH$_2$CH$_2$), 2.82 (t, J=7.2 Hz, 4H, ArCH$_2$), 7.37 (d, J=8.0 Hz, 2H, ArH), 7.66 (s, 2H, ArH), 7.96 (d, J=8.0 Hz, 2H, ArH), 8.13 (s, 2H, ArH), 8.65 (s, 2H, ArH).

Example 12

Synthesis of 3,9-didodecyldinaphtho[2,3-b:2',3'-d]thiophene

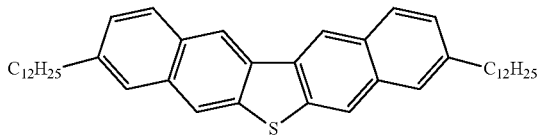

A pale yellow solid title compound (yield: 83%) was obtained in accordance with Example 6 except that decyl of the starting material was changed to dodecyl in Example 6. Values of physical properties are shown below.

$^1$H NMR (600 MHz, CDCl$_3$): δ 0.88 (t, J=7.2 Hz, 6H, CH$_3$), 1.27-1.38 (m, 36H, (CH$_2$)$_9$), 1.73 (quin, J=7.8 Hz, 2H, ArCH$_2$CH$_2$), 2.81 (t, J=7.8 Hz, 4H, ArCH$_2$), 7.36 (d, J=8.4 Hz, 2H, ArH), 7.66 (s, 2H, ArH), 7.96 (d, J=8.4 Hz, 2H, ArH), 8.14 (s, 2H, ArH), 8.65 (s, 2H, ArH). TOF HRMS (APCI+): Calcd for C$_{44}$H$_{60}$S [M+H] 621.4494. found 621.4493.

Example 13

Synthesis of dinaphtho[2,3-b:2',3'-d]selenophene

First Step

Synthesis of [2,2'-binaphthalene]-3,3'-diylbis(trifluoromethanesulfonate)

Figure 17:
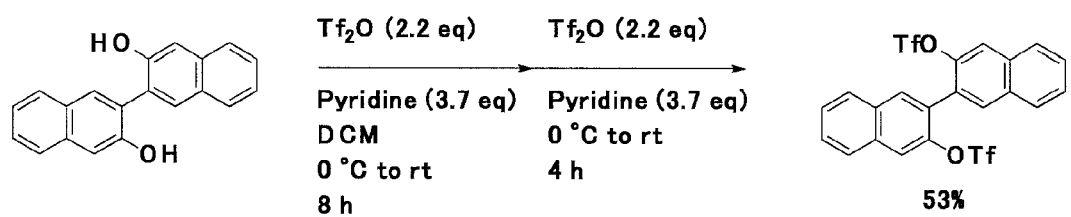
FIG. 17 shows the reaction scheme for producing [2,2'-binaphthalene]-3,3'-diylbis(trifluoromethanesulfonate).

To a dehydrated dichloromethane solution (50 mL) of [2,2'-binaphthalene]-3,3'-diol (2.86 g, 10.0 mmol), pyridine (2.98 mL, 37.0 mmol) was added at 0° C., and then trifluoromethanesulfonic anhydride (Tf$_2$O; 3.69 mL, 22.0 mmol) was added dropwise thereto. The resulting mixture was stirred at room temperature for 8 hours, then, pyridine (2.98 mL, 37.0 mmol) was added thereto at 0° C., and then trifluoromethanesulfonic anhydride (3.69 mL, 22.0 mmol) was added dropwise thereto. The resulting mixture was stirred at room temperature for 4 hours, and then water was added thereto to stop a reaction thereof. An organic layer was extracted with ethyl acetate, and then dried over magnesium sulfate. After removing a desiccant, a solution thereof was concentrated under reduced pressure by a rotary evaporator. The resulting crude product was purified by silica gel column chromatography using a mixed solvent of hexane and chloroform (hexane:chloroform=90:10 to 70:30 (volume ratio)) as an eluent to obtain a white solid (2.92 g, 2.07 mmol). Yield: 53%. See FIG. 17.

$^1$H NMR (600 MHz, CDCl$_3$): δ 7.62-7.68 (m, 4H, ArH), 7.92 (s, 2H, ArH), 7.94-7.97 (m, 4H, ArH), 8.04 (s, 2H, ArH).

Second Step

Figure 18:
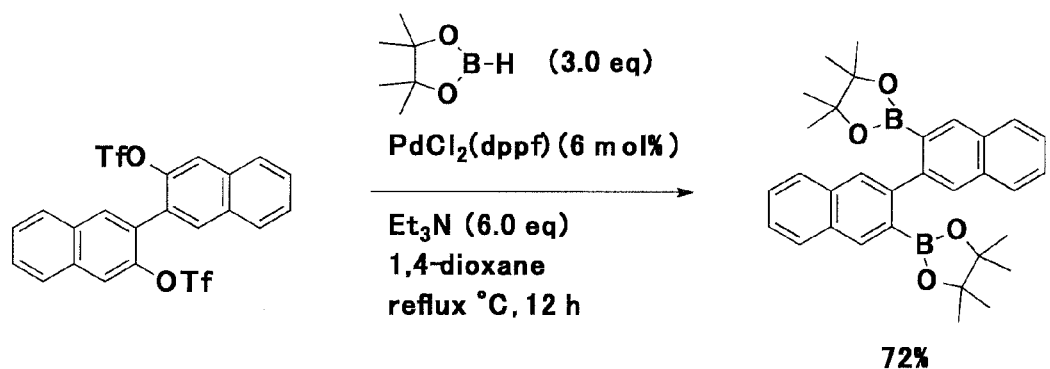
FIG. 18 shows the reaction scheme for producing 3,3'-bis(4,4,5,5-tetramethyl-1,3,2-dioxaborolanyl)-2,2'-binaphthalene.

Synthesis of 3,3'-bis(4,4,5,5-tetramethyl-1,3,2-dioxaborolanyl)-2,2'-binaphthalene To a dehydrated 1,4-dioxane solution (13.5 mL) of [2,2'-binaphthalene]-3,3'-diylbis(trifluoromethanesulfonate) (1.49 g, 2.70 mmol), triethylamine (2.26 mL, 16.2 mmol), a 1,1'-bis(diphenylphosphino)ferrocene-palladium(II) dichloride(PdCl$_2$(dppf))-dichloromethane complex (132 mg, 0.162 mmol) and 4,4,5,5-tetramethyl-1,3,2-dioxaborolane (1.17 mL, 8.10 mmol) were added at room temperature. Temperature was risen, and the resulting mixture was heated and refluxed for 12 hours, and then water was added thereto to stop a reaction thereof. An organic layer was extracted with ethyl acetate, and then dried over magnesium sulfate. After removing a desiccant, a solution thereof was concentrated under reduced pressure by a rotary evaporator. The resulting crude product was purified by silica gel column chromatography using a mixed solvent of hexane and chloroform (hexane:chloroform=7:3 to 4:6 (volume ratio)) as an eluent to obtain a white solid (983 mg, 1.94 mmol). Yield: 72%. See FIG. 18.

$^1$H NMR (600 MHz, CDCl$_3$): δ 1.08 (s, 24H, CH$_3$), 7.48 (dd, J=8.4 Hz, 8.4 Hz, 2H, ArH), 7.51 (dd, J=8.4 Hz, 8.4 Hz, 2H, ArH), 7.79 (s, 2H, ArH), 7.82 (d, J=8.4 Hz, ArH), 7.92 (d, J=8.4 Hz, ArH), 8.27 (s, 2H, ArH).

Third Step

Synthesis of 3,3'-dibromo-2,2'-binaphthalene

Figure 19:
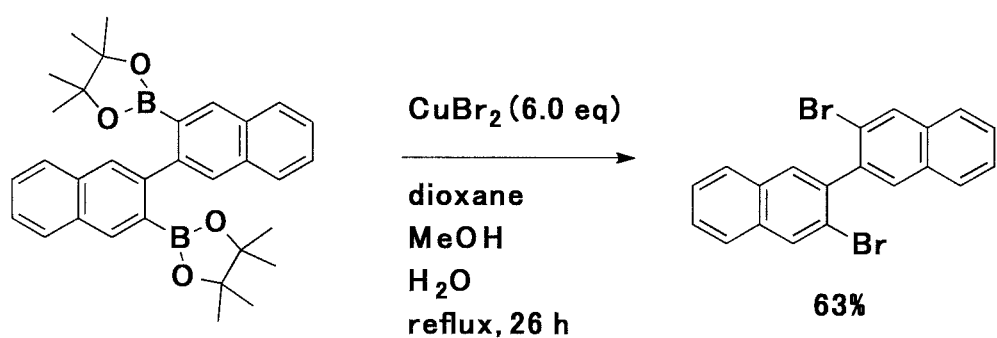
FIG. 19 shows the reaction scheme for producing 3,3'-dibromo-2,2'-binaphthalene.

To a dehydrated 1,4-dioxane solution (21.3 mL) of 3,3'-bis(4,4,5,5-tetramethyl-1,3,2-dioxaborolanyl)-2,2'-binaphthalene (861 mg, 1.70 mmol), methanol (8.5 mL), water (4.3 mL) and copper bromide (II) (2.28 g, 10.2 mmol) were added at room temperature. The resulting mixture was heated and refluxed, stirred for 26 hours, and then returned to room temperature to stop a reaction thereof. Water was added thereto, an organic layer was extracted with chloroform, and then dried over magnesium sulfate. After removing a desiccant, a solution thereof was concentrated under reduced pressure by a rotary evaporator. The resulting crude product was purified by silica gel column chromatography using a mixed solvent of hexane and chloroform (hexane:chloroform=95:5 to 85:15 (volume ratio)) as an eluent to obtain a white solid (441 mg, 10.7 mmol). Yield: 63%. See FIG. 19.

$^1$H NMR (400 MHz, CDCl$_3$): δ 7.53-7.59 (m, 4H, ArH), 7.81 (s, 2H, ArH), 7.83-7.87 (m, 4H, ArH), 8.22 (s, 2H, ArH).

Fourth Step

Synthesis of dinaphtho[2,3-b:2',3'-d]selenophene

Figure 20:
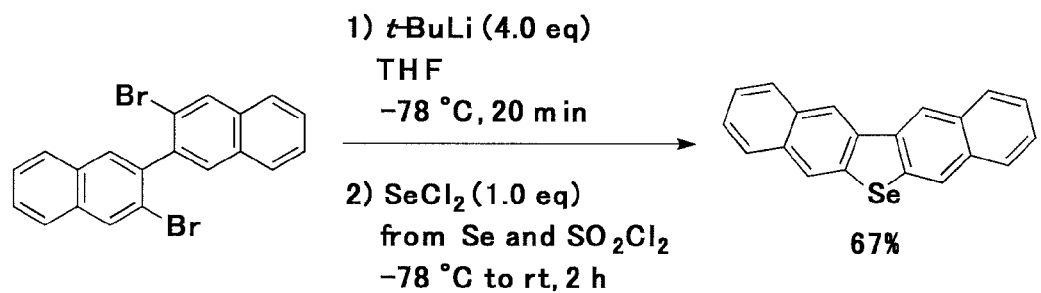
FIG. 20 shows the reaction scheme for producing dinaphtho[2,3-b:2',3'-d]selenophene.

To selenium (7.9 mg, 0.100 mmol), sulfuryl chloride (13.4 mg, 0.100 mmol) was added, the resulting mixture was stirred at room temperature for 5 minutes, and then a dehydrated tetrahydrofuran solution (0.2 mL) was added thereto. The resulting mixture was stirred at room temperature for 1 hour, and selenium dichloride in a red solution was prepared. To a dehydrated tetrahydrofuran solution (0.50 mL) of 3,3'-dibromo-2,2'-binaphthalene (41.2 mg, 0.100 mmol), t-butyllithium (1.65 M pentane solution, 0.242 mL, 0.4 mmol) was added dropwise at −78° C. The resulting mixture was stirred for 20 minutes, and then selenium dichloride prepared was added thereto at −78° C., and the resulting mixture was heated to room temperature and stirred for 2 hours. Water was added thereto, an organic layer was extracted with chloroform, and then dried over magnesium sulfate. After removing a desiccant, a solution thereof was concentrated under reduced pressure by a rotary evaporator. The resulting crude product was purified by silica gel column chromatography using a mixed solvent of hexane and chloroform (hexane:chloroform=95:5 to 90:10 (volume ratio)) as an eluent, and purified by gel permeation chromatography to obtain a pale yellow solid (18.2 mg, 0.0673 mmol). Yield: 67%. See FIG. 20.

$^1$H NMR (400 MHz, CDCl$_3$): δ 7.51-7.57 (m, 4H, ArH), 7.86-7.90 (m, 2H, ArH), 8.02-8.06 (m, 2H, ArH), 7.81 (s, 2H, ArH), 8.28 (s, 2H, ArH), 8.71 (s, 2H, ArH).

Example 14

Synthesis of 3,9-dihexyldinaphtho[2,3-b:2',3'-d]selenophene

First Step

Synthesis of 6,6'-dihexyl-[2,2'-binaphthalene]-3,3'-diylbis(trifluoromethanesulfonate)

Figure 21:
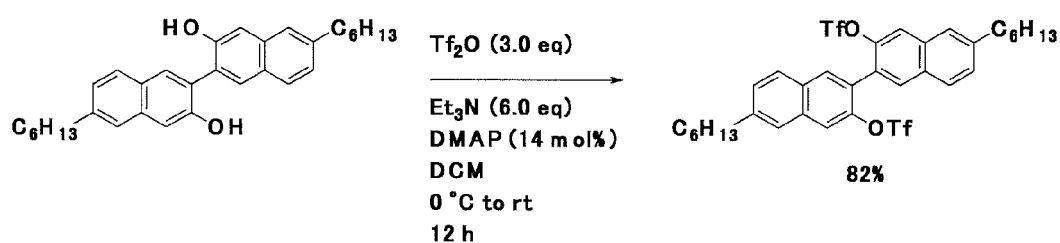
FIG. 21 shows the reaction scheme for producing 6,6'-dihexyl-[2,2'-binaphthalene]-3,3'-diylbis(trifluoromethanesulfonate).

To a dehydrated dichloromethane solution (148 mL) of 6,6'-dihexyl-[2,2'-binaphthalene]-3,3'-diol (16.8 g, 37.0 mmol), triethylamine (30.9 mL, 222 mmol) and N,N-dimethyl-4-aminopyridine (DMAP; 633 mg, 5.18 mmol) were added at 0° C., and then a dehydrated dichloromethane solution (50 mL) of trifluoromethanesulfonic anhydride (18.6 mL, 111 mmol) was added dropwise thereto at 0° C. The resulting mixture was stirred at room temperature for 12 hours, and then water was added thereto to stop a reaction thereof. An organic layer was extracted with ethyl acetate, and then dried over magnesium sulfate. After removing a desiccant, a solution thereof was concentrated under reduced pressure by a rotary evaporator. The resulting crude product was purified by silica gel column chromatography using a mixed solvent of hexane and chloroform (hexane:chloroform=98:2 to 90:10 (volume ratio)) as an eluent to obtain a white solid (21.8 g, 30.3 mmol). Yield: 82%. See FIG. 21.

$^1$H NMR (400 MHz, CDCl$_3$): δ 0.93 (t, J=6.8 Hz, 6H, CH$_3$), 1.32-1.43 (m, 12H, (CH$_2$)$_3$), 1.75 (quin, J=7.2 Hz, 4H, ArCH$_2$CH$_2$), 2.83 (t, J=7.2 Hz, 4H, ArCH$_2$), 7.47 (d, J=8.4 Hz, 2H, ArH), 7.71 (s, 2H, ArH), 7.83 (s, 2H, ArH), 7.85 (d, J=8.4 Hz, 2H, ArH), 7.97 (s, 2H, ArH).

Second Step

Synthesis of 2,2'-(6,6'-dihexyl-[2,2'-binaphthalene]-3,3'-diyl)bis(4,4,5,5-tetramethyl-1,3,2-dioxaborolane)

Figure 22:
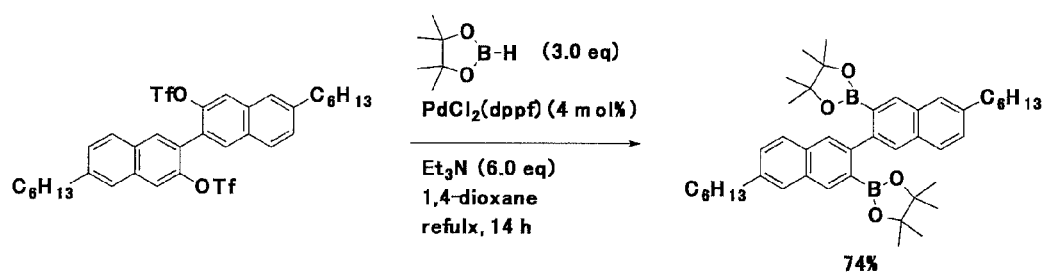
FIG. 22 shows the reaction scheme for producing 2,2'-(6,6'-dihexyl-[2,2'-binaphthalene]-3,3'-diyl)bis(4,4,5,5-tetramethyl-1,3,2-dioxaborolane).

To a dehydrated 1,4-dioxane solution (90 mL) of 6,6'-dihexyl-[2,2'-binaphthalene]-3,3'-diylbis(trifluoromethane-sulfonate) (12.9 g, 18.0 mmol), triethylamine (15.1 mL, 108 mmol), a 1,1'-bis(diphenylphosphino)ferrocene-palladium (II) dichloride-dichloromethane complex (588 mg, 0.720 mmol) and 4,4,5,5-tetramethyl-1,3,2-dioxaborolane (7.84 mL, 54.0 mmol) were added at room temperature. Temperature was risen, the resulting mixture was heated and refluxed for 14 hours, and then water was added thereto to stop a reaction thereof. An organic layer was extracted with ethyl acetate, and then dried over magnesium sulfate. After removing a desiccant, a solution thereof was concentrated under reduced pressure by a rotary evaporator. The resulting crude product was purified by silica gel column chromatography using a mixed solvent of hexane and chloroform (hexane:chloroform=8:2 to 7:4 (volume ratio)) as an eluent to obtain a white solid (8.99 g, 13.3 mmol). Yield: 72%. See FIG. 22.

$^1$H NMR (400 MHz, CDCl$_3$): δ 0.90 (t, J=6.8 Hz, 6H, CH$_3$), 1.08 (s, 24H, CH$_3$), 1.31-1.43 (m, 12H, (CH$_2$)$_3$), 1.71 (quin, J=7.6 Hz, 4H, ArCH$_2$CH$_2$), 2.79 (t, J=7.6 Hz, 4H, ArCH$_2$), 7.35 (d, J=8.4 Hz, 2H, ArH), 7.67 (s, 2H, ArH), 7.72 (d, J=8.4 Hz, 2H, ArH), 7.73 (s, 2H, ArH), 8.18 (s, 2H, ArH).

Third Step

Synthesis of 3,3'-dibromo-6,6'-dihexyl-2,2'-binaphthalene

Figure 23:
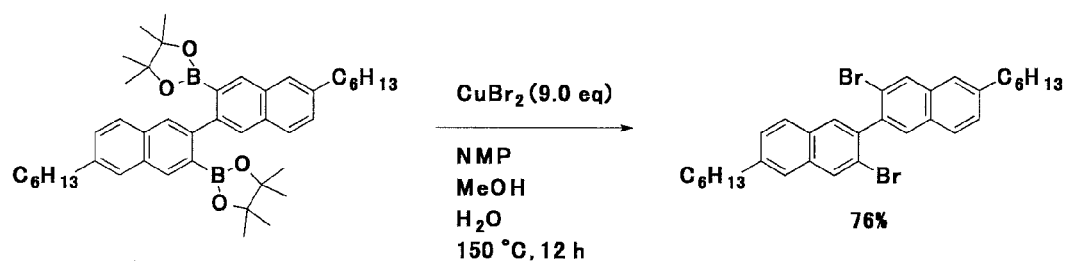
FIG. 23 shows the reaction scheme for producing 3,3'-dibromo-6,6'-dihexyl-2,2'-binaphthalene.

In a sealed tube, a N-methyl-2-pyrrolidone solution (NMP; 15 mL) of 2,2'-(6,6'-dihexyl-[2,2'-binaphthalene]-3,3'-diyl)bis(4,4,5,5-tetramethyl-1,3,2-dioxaborolane) (675 mg, 1.00 mmol) was prepared, and methanol (6 mL), water (6 mL) and copper(II) bromide (1.34 g, 6.00 mmol) were added thereto at room temperature. The resulting mixture was heated to 150° C., stirred for 6 hours, and then returned to room temperature, and copper(II) bromide (670 mg, 3.00 mmol) was added thereto. The resulting mixture was heated to 150° C., stirred for 6 hours, and then water was added thereto to stop a reaction thereof. An organic layer was extracted with ethyl acetate, and then dried over magnesium sulfate. After removing a desiccant, a solution thereof was concentrated under reduced pressure by a rotary evaporator. The resulting crude product was purified by silica gel column chromatography using hexane as an eluent to obtain a white solid (442 mg, 0.76 mmol). Yield: 76%. See FIG. 23.

$^1$H NMR (600 MHz, CDCl$_3$): δ 0.91 (t, J=6.6 Hz, 6H, CH$_3$), 1.31-1.40 (m, 12H, (CH$_2$)$_3$), 1.72 (quin, J=7.2 Hz, 4H, ArCH$_2$CH$_2$), 2.79 (t, J=7.2 Hz, 4H, ArCH$_2$),7.38 (d, J=8.4 Hz, 2H, ArH), 7.59 (s, 2H, ArH), 7.75-7.76 (m, 4H, ArH), 8.13 (s, 2H, ArH).

Fourth Step

Synthesis of 3,9-dihexyldinaphtho[2,3-b:2',3'-d]selenophene

Figure 24:
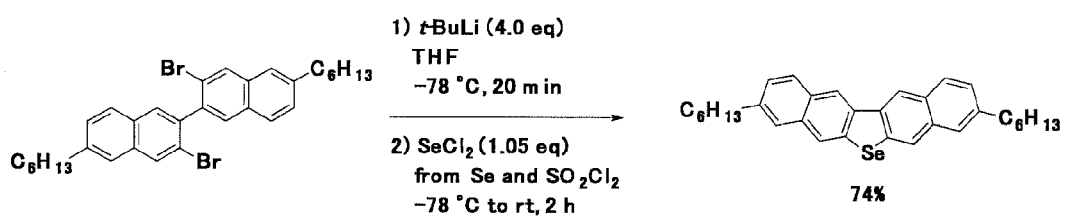
FIG. 24 shows the reaction scheme for producing 3,9-dihexyldinaphtho[2,3-b:2',3'-d]selenophene.

To selenium (33.2 mg, 0.420 mmol), sulfuryl chloride (34.0 μL, 0.420 mmol) was added, the resulting mixture was stirred at room temperature for 10 minutes, and then a dehydrated tetrahydrofuran solution (1.05 mL) was added thereto. The resulting mixture was stirred at room temperature for 1 hour, and selenium dichloride in a red solution was prepared. To a dehydrated tetrahydrofuran solution (1.6 mL) of 3,3'-dibromo-6,6'-dihexyl-2,2'-binaphthalene (232 mg, 0.400 mmol), t-butyllithium (1.65 M pentane solution, 0.970 mL, 1.60 mmol) was added dropwise at −78° C. The resulting mixture was stirred at −78° C. for 20 minutes, and then selenium dichloride prepared was added thereto at −78° C., and the resulting mixture was heated to room temperature over 3 hours and stirred for 2 hours. Water was added thereto, an organic layer was extracted with chloroform, and then dried over magnesium sulfate. After removing a desiccant, a solution thereof was concentrated under reduced pressure by a rotary evaporator. The resulting crude product was dissolved into dichloromethane, and methanol was added thereto as a poor solvent to obtain a pale yellow solid (148 mg, 0.296 mmol). Yield: 74%. See FIG. 24.

$^1$H NMR (600 MHz, CDCl$_3$): δ 0.90 (t, J=6.6 Hz, 6H, CH$_3$), 1.29-1.40 (m, 12H, (CH$_2$)$_3$), 1.72 (quin, J=7.2 Hz, 4H, ArCH$_2$CH$_2$), 2.81 (t, J=7.2 Hz, 4H, ArCH$_2$), 7.37 (d, J=8.4 Hz, 2H, ArH), 7.62 (s, 2H, ArH), 7.94 (d, J=8.4 Hz, 2H, ArH), 8.18 (s, 2H, ArH), 8.63 (s, 2H, ArH).

Example 15

Synthesis of 5,9-di(2-thienyl)dinaphtho[2,1-b:1',2'-d]furan

First Step

Synthesis of 5,9-dibromodinaphtho[2,1-b:1',2'-d]furan

Figure 25:
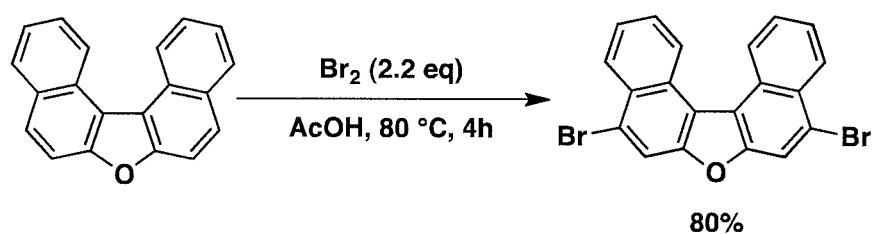
FIG. 25 shows the reaction scheme for producing 5,9-dibromodinaphtho[2,1-b:1',2'-d]furan.

To an acetic acid (AcOH; 100 mL) suspension of dinaphtho[2,1-b:1',2'-d]furan (5.00 g, 18.6 mmol), bromine (6.55 g, 41.0 mmol) was added, and the resulting mixture was stirred at 80° C. for 4 hours. Temperature was returned to room temperature, and then a reaction mixture thereof was added to an aqueous solution of potassium hydroxide, precipitates were separated by filtration, and subjected to thermal recrystallization with toluene to obtain a white solid title compound (6.32 g, 80%). See FIG. 25.

$^1$H NMR (600 MHz, CDCl$_3$): δ 9.09 (d, J=8.4 Hz, 2H, ArH), 8.52 (d, J=8.4 Hz, 2H, ArH), 8.19 (s, 2H, ArH), 7.80 (dd, J=7.8 Hz, 8.4 Hz, 2H, ArH), 7.71 (dd, J=7.8 Hz, 8.4 Hz, 2H, ArH). ESI-MS [M+H] m/z=425. Anal. Calcd for C$_{20}$H$_{10}$Br$_2$O: C, 56.37; H, 2.37. Found: C, 56.50; H, 2.62.

Second Step

Synthesis of 5,9-di(2-thienyl)dinaphtho[2,1-b:1',2'-d]furan

Figure 26:
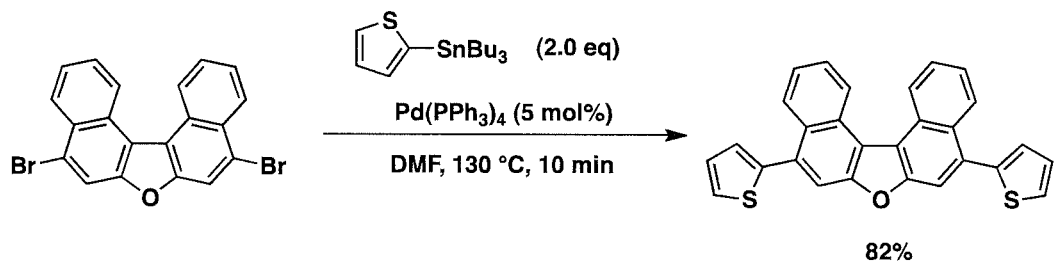
FIG. 26 shows the reaction scheme for producing 5,9-di (2-thienyl)dinaphtho[2,1-b:1',2'-d]furan.

To a N,N-dimethylformamide (DMF; 10 mL) suspension of 5,9-dibromodinaphtho[2,1-b:1',2'-d]furan (426 mg, 1.00 mmol), tributyl(2-thienyl)tin (764 mg, 2.04 mmol) and tetrakis(triphenylphosphine)palladium(0) (58 mg, 0.05 mmol) were added, and the resulting mixture was stirred at 130° C. for 10 minutes. Temperature was returned to room temperature, a reaction solution thereof was added to an aqueous solution of potassium fluoride, and a precipitated mineral salt was filtered off. A filtrate thereof was washed with water, and an organic layer was extracted with toluene 3 times. A combined organic layer was washed with water and saturated brine, and dried over magnesium sulfate. After removing a desiccant, concentration under reduced pressure was carried out by a rotary evaporator. The resulting crude product was dissolved into chloroform to be passed through a silica gel, and then further subjected to gel filtration chromatography using chloroform as an eluent to obtain a yellow solid title compound (355 mg, 82%). See FIG. 26.

$^1$H NMR (600 MHz, CDCl$_2$CDCl$_2$): δ 9.15 (d, J=8.4 Hz, 2H, ArH), 8.41 (d, J=8.4 Hz, 2H, ArH), 7.92 (s, 2H, ArH), 7.76 (dd, J=7.2 Hz, 8.4 Hz, 2H, ArH), 7.57 (dd, J=7.2 Hz, 8.4 Hz, 2H, ArH), 7.48 (d, J=4.8 Hz, 2H, thiophene), 7.33 (d, J=3.6 Hz, 2H, thiophene), 7.23-7.21 (dd, J=3.6 Hz, 4.8 Hz, 2H, thiophene). ESI-MS [M+H] m/z=433. Anal. Calcd for C$_{28}$H$_{16}$OS$_2$: C, 77.75; H, 3.73. Found: C, 77.53; H, 3.89.

Example 16

Synthesis of 5,9-di(2-furyl)dinaphtho[2,1-b:1',2'-d]furan

Figure 27:
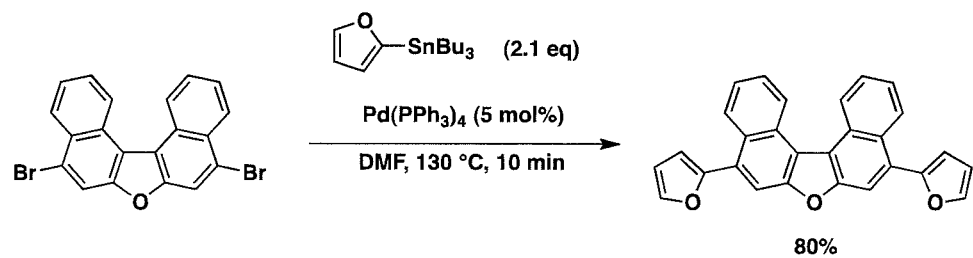
FIG. 27 shows the reaction scheme for producing 5,9-di (2-furyl)dinaphtho[2,1-b:1',2'-d]furan.

To a N,N-dimethylformamide (10 mL) suspension of 5,9-dibromodinaphtho[2,1-b:1',2'-d]furan (426 mg, 1.00 mmol), tributyl(2-furyl)tin (742 mg, 2.08 mmol) and tetrakis(triphenylphosphine)palladium(0) (58 mg, 0.05 mmol) were added, and the resulting mixture was stirred at 130° C. for 10 minutes. Temperature was returned to room temperature, and then a reaction solution thereof was added to an aqueous solution of potassium fluoride, and a precipitated mineral salt was filtered off. A filtrate thereof was washed with water, and an organic layer was extracted with toluene 3 times. A combined organic layer was washed with water and saturated brine, and dried over magnesium sulfate. After removing a desiccant, concentration under reduced pressure was carried out by a rotary evaporator. The resulting crude product was dissolved into chloroform to be passed through a silica gel, and then concentrated under reduced pressure by a rotary evaporator, dissolved into a minimum amount of chloroform again, and reprecipitated in methanol to obtain a white solid title compound (318 mg, 80%). See FIG. 27.

$^1$H NMR (600 MHz, CDCl$_3$): δ 9.20 (d, J=8.4 Hz, 2H, ArH), 8.62 (d, J=8.4 Hz, 2H, ArH), 8.10 (s, 2H, ArH), 7.78 (dd, J=7.2 Hz, 8.4 Hz, 2H, ArH), 7.70 (d, J=1.2 Hz, 2H, furan), 7.64 (dd, J=7.2 Hz, 8.4 Hz, 2H, ArH), 6.86 (d, J=3.6 Hz, 2H, furan), 6.66 (d, J=1.2 Hz, 3.6 Hz, 2H, furan). ESI-MS [M+H] m/z=401.

Example 17

Synthesis of 5,9-di(2-thiazolyl)dinaphtho[2,1-b:1',2'-d]furan

Figure 28:
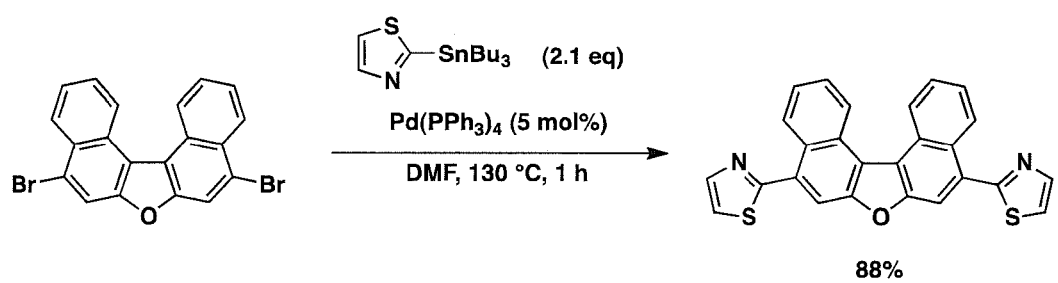
FIG. 28 shows the reaction scheme for producing 5,9-di (2-thiazolyl)dinaphtho[2,1-b:1',2'-d]furan.

To a N,N-dimethylformamide (10 mL) suspension of 5,9-dibromodinaphtho[2,1-b:1',2'-d]furan (426 mg, 1.00 mmol), tributyl(2-thiazolyl)tin (775 mg, 2.07 mmol), and tetrakis(triphenylphosphine)palladium(0) (58 mg, 0.05 mmol) were added, and the resulting mixture was stirred at 130° C. for 1 hour. Temperature was returned to room temperature, and then a reaction solution thereof was added to an aqueous solution of potassium fluoride, and a precipitated mineral salt was filtered off. A filtrate thereof was washed with water, and an organic layer was extracted with toluene 3 times. A combined organic layer was washed with water and saturated brine, and dried over magnesium sulfate. After removing a desiccant, concentration under reduced pressure was carried out by a rotary evaporator. The resulting crude product was washed with hexane, and separated by filtration to obtain a yellow solid title compound (383 mg, 88%). See FIG. 28.

$^1$H NMR (600 MHz, CDCl$_3$): δ 9.23 (d, J=9.0 Hz, 2H, ArH), 8.95 (d, J=9.0 Hz, 2H, ArH), 8.20 (s, 2H, ArH), 8.12 (d, J=4.2 Hz, 2H, thiazole), 7.82 (dd, J=6.6 Hz, 9.0 Hz, 2H, ArH), 7.69 (dd, J=6.6 Hz, 9.0 Hz, 2H, ArH), 7.57 (d, J=4.2 Hz, thiazole). MALDI-TOF-MS (positive) m/z=435. Anal. Calcd for C$_{26}$H$_{14}$N$_2$OS$_2$: C, 71.87; H, 3.25; N, 6.45. Found: C, 71.58; H, 3.31; N, 6.44.

Example 18

Synthesis of 5,9-dioctyldinaphtho[2,1-b:1',2'-d]furan

Figure 29:
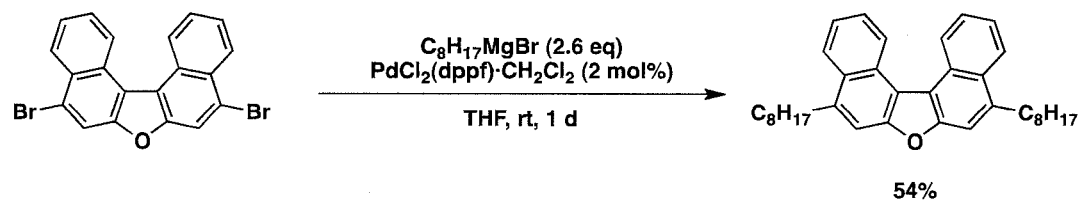
FIG. 29 shows the reaction scheme for producing 5,9-dioctyldinaphtho[2,1-b:1',2'-d]furan.

To a tetrahydrofuran (4.5 mL) solution of 5,9-dibromodinaphtho[2,1-b:1',2'-d]furan (951 mg, 2.23 mmol), a 1,1'-bis(diphenylphosphino)ferrocene palladium(II) dichloride-dichloromethane complex (36 mg, 0.045 mmol) was added, and a tetrahydrofuran solution (5.80 mL, 5.80 mmol) of 1.0 M octylmagnesium bromide was added dropwise thereto at 0° C. at a rate of 2 mL per minute. The resulting mixture was stirred at room temperature for 24 hours, and then a reaction thereof was stopped using hydrochloric acid. An organic layer was extracted with toluene 3 times. A combined organic layer was washed with water and saturated brine, and dried over magnesium sulfate. After removing a desiccant, concentration under reduced pressure was carried out by a rotary evaporator. The resulting crude product was purified by silica gel column chromatography using hexane as an eluent to obtain a white solid title compound (595 mg, 54%). See FIG. 29.

$^1$H NMR (600 MHz, CDCl$_3$): δ 9.17 (d, J=8.4 Hz, 2H, ArH), 8.26 (d, J=8.4 Hz, 2H, ArH), 7.72-7.70 (m, 4H, ArH), 7.61 (dd, J=6.6 Hz, 8.4 Hz, 2H, ArH), 3.23 (t, J=6.6 Hz, 4H, ArCH$_2$CH$_2$), 1.86 (quin, J=6.6 Hz, 4H, ArCH$_2$CH$_2$), 1.53-1.48 (m, 4H, CH$_2$CH$_2$CH$_2$), 1.43-1.37 (m, 4H, CH$_2$CH$_2$CH$_2$), 1.35-1.25 (m, 12H, (CH$_2$)$_3$), 0.89 (t, J=6.6 Hz, 6H, CH$_3$). MALDI-TOF-MS (positive) m/z=492.

Solubility of the compound was evaluated. As a result, under room temperature, the compound was dissolved into chloroform at 381 g/L (20.5 wt. %), and into toluene at 137 g/L (13.6 wt. %). The compound is clearly found to show high solubility in any of solvent to allow use in an application process.

Example 19

Synthesis of 5,9-didodecyldinaphtho[2,1-b:1',2'-d]furan

Figure 30:
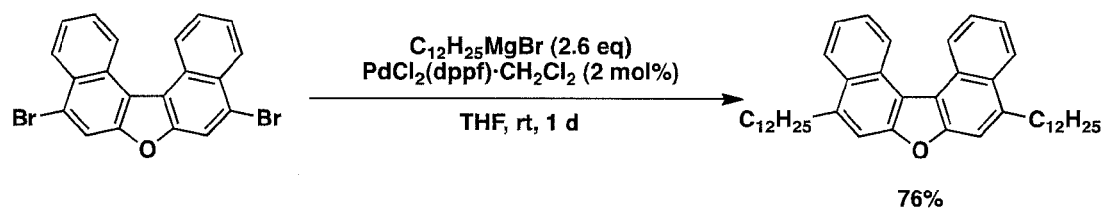
FIG. 30 shows the reaction scheme for producing 5,9-didodecyldinaphtho[2,1-b:1',2'-d]furan.

To a tetrahydrofuran (3.6 mL) solution of 5,9-dibromodinaphtho[2,1-b:1',2'-d]furan (775 mg, 1.82 mmol), a 1,1'-bis(diphenylphosphino)ferrocene palladium(II) dichloride-dichloromethane complex (30 mg, 0.036 mmol) was added, and a diethyl ether solution (4.73 mL, 4.73 mmol) of 1.0 M dodecylmagnesium bromide was added dropwise thereto at 0° C. at a rate of 2 mL per minute. The resulting mixture was stirred at room temperature for 24 hours, and then a reaction thereof was stopped using hydrochloric acid. An organic layer was extracted with toluene 3 times. A combined organic layer was washed with water and saturated brine, and dried over magnesium sulfate. After removing a desiccant, concentration under reduced pressure was carried out by a rotary evaporator. The resulting crude product was purified by silica gel column chromatography using a mixed solvent of hexane and chloroform (hexane:chloroform=9:1 (volume ratio)) as an eluent to obtain a white solid title compound (831 mg, 76%). See FIG. 30.

$^1$H NMR (400 MHz, CDCl$_3$): δ 9.17 (d, J=8.4 Hz, 2H, ArH), 8.26 (d, J=8.4 Hz, 2H, ArH), 7.72-7.70 (m, 4H, ArH), 7.61 (dd, J=6.6 Hz, 8.4 Hz, 2H, ArH), 3.23 (t, J=7.2 Hz, 4H, ArCH$_2$CH$_2$), 1.86 (quin, J=7.2 Hz, 4H, ArCH$_2$CH$_2$), 1.51-1.46 (m, 4H, CH$_2$CH$_2$CH$_2$), 1.43-1.39 (m, 4H, CH$_2$CH$_2$CH$_2$), 1.34-1.20 (m, 28H, (CH$_2$)$_7$), 0.89 (t, J=8.0 Hz, 6H, CH$_3$). MALDI-TOF-MS (positive) m/z=604.

Example 20

Synthesis of 5,9-diphenyldinaphtho[2,1-b:1',2'-d]furan

Figure 31:
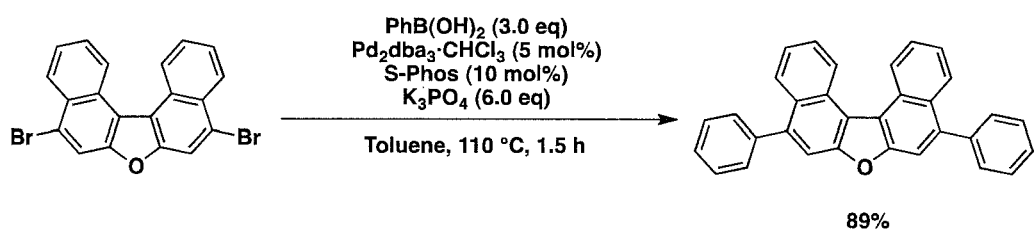
FIG. 31 shows the reaction scheme for producing 5,9-diphenyldinaphtho[2,1-b:1',2'-d]furan.

To a toluene solution (3 mL) of 5,9-dibromodinaphtho[2,1-b:1',2'-d]furan (426 mg, 1.00 mmol), a tris(dibenzylideneacetone)dipalladium(0) (Pd$_2$dba$_3$)-chloroform complex (52 mg, 0.05 mmol), 2-dicyclohexylphosphino-2',6'-dimethoxybiphenyl (S-Phos; 41 mg, 0.10 mmol), tripotassium phosphate (1.27 g, 6.00 mmol) and phenylboronic acid (366 mg, 3.00 mmol) were added, and the resulting mixture was stirred at 110° C. for 90 minutes. Temperature was returned to room temperature, and an inorganic substance was filtered off through a silica gel, and then concentration under reduced pressure was carried out by a rotary evaporator. The resulting crude product was purified by silica gel column chromatography using a mixed solvent of hexane and chloroform (hexane:chloroform=4:1 (volume ratio)) as an eluent to obtain a white solid title compound (373 mg, 89%). See FIG. 31.

$^1$H NMR (400 MHz, CDCl$_3$): δ 9.25 (d, J=8.4 Hz, 2H, ArH), 8.11 (d, J=8.4 Hz, 2H, ArH), 7.83 (s, 2H, ArH), 7.77 (dd, J=7.2 Hz, 8.4 Hz, 2H, ArH), 7.63-7.48 (m, 12H, ArH).

Solubility of the compound was evaluated. As a result, under room temperature, the compound was dissolved into chloroform at 43 g/L (2.8 wt. %), and into toluene at 23 g/L (2.6 wt. %). The compound is clearly found to show high solubility in any of solvent to allow use in an application process.

Comparative Example 1

Synthesis of dinaphtho[2,3-b:2',3'-d]thiophene

A title compound described in Example in Patent literature No. 6 was synthesized by a method according to the invention.

First Step

Synthesis of O,O'-(2,2'-binaphthalene-3,3'-diyl)bis(dimethylcarbamothioate)

Figure 32:
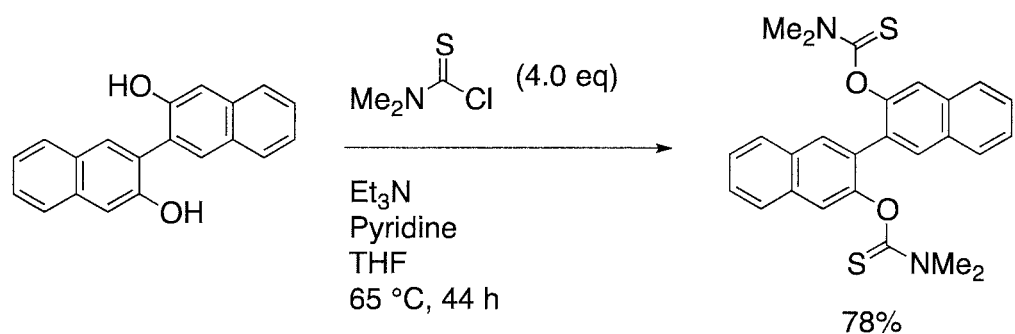
FIG. 32 shows the reaction scheme for producing O,O'-(2,2'-binaphthalene-3,3'-diyl)bis(dimethylcarbamothioate)

To a tetrahydrofuran solution (10.9 mL) of 2,2'-binaphthalene-3,3'-diol (1.43 g, 5.0 mmol), triethylamine (5.32 mL), pyridine (2.08 mL) and N,N-dimethylthiocarbamoyl chloride (2.47 g, 20.0 mmol) were added, and the resulting mixture was stirred at 65° C. for 44 hours. A solution thereof was concentrated under reduced pressure by a rotary evaporator. The resulting crude product was purified by silica gel column chromatography using a mixed solvent of hexane and ethyl acetate (hexane:ethyl acetate=7:3 (volume ratio)) as an eluent to obtain a colorless solid title compound (1.79 g, 3.89 mmol, 78%). See FIG. 32.

Melting point: 230.5 to 231.0° C. $^1$H NMR (400 MHz, CD$_3$Cl): δ 3.00 (s, 6H, NCH$_3$), 3.16 (s, 6H, NCH$_3$), 7.46-7.52 (m, 4H, ArH), 7.54 (s, 2H, ArH), 7.84-7.88 (m, 4H, ArH), 7.98 (s, 2H, ArH). $^{13}$C NMR (150 MHz, CD$_3$Cl): δ 38.5, 43.1, 120.9, 126.0, 126.6, 127.6, 128.0, 130.2, 131.3, 133.2, 149.8, 187.2. TOF HRMS (APCI): Calcd for C$_{26}$H$_{25}$N$_2$S$_2$O$_2$ [M+H] 461.1357. found, 461.1349.

Second Step

Synthesis of dinaphtho[2,3-b:2',3'-d]thiophene

Figure 33:
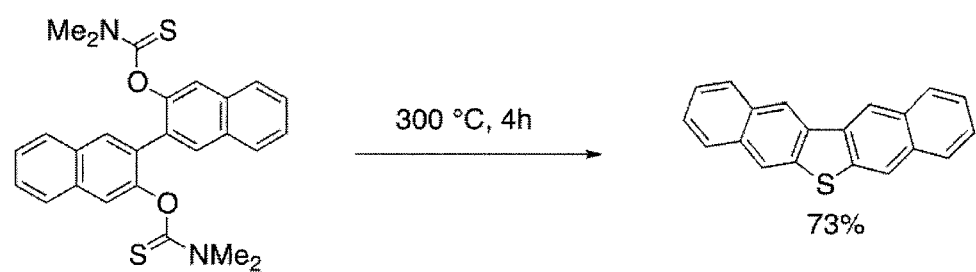
FIG. 33 shows the reaction scheme for producing dinaphtho[2,3-b:2',3'-d]thiophene.

Then, O,O'-(2,2'-binaphthalene-3,3'-diyl)bis(dimethylcarbamothioate) (691 mg, 1.50 mmol) was sealed into a Pyrex tube, and heated at 300° C. for 4 hours. Temperature was returned to room temperature, and then the resultant product was subjected to thermal recrystallization in a mixed solvent of toluene and 2-propanol (toluene:2-propanol=8:2 (volume ratio)) to obtain a pale yellow solid title compound (310 mg, 1.09 mmol, 73%). See FIG. 33.

Melting point: 282 to 283° C. $^1$H NMR (600 MHz, CDCl$_2$CDCl$_2$): δ 7.49-7.56 (m, 4H, ArH), 7.87 (d, J=7.2 Hz, 2H, ArH), 8.03 (d, J=7.2 Hz, 2H, ArH), 8.19 (s, 2H, ArH), 8.66 (s, 2H, ArH). MS (APCI+): 285 (M+H). Anal. Calcd for C$_{20}$H$_{12}$S: C, 84.47; H, 4.25. Found: C, 84.89; H, 4.43.

Evaluation of Chemical Stability

Figure 5:
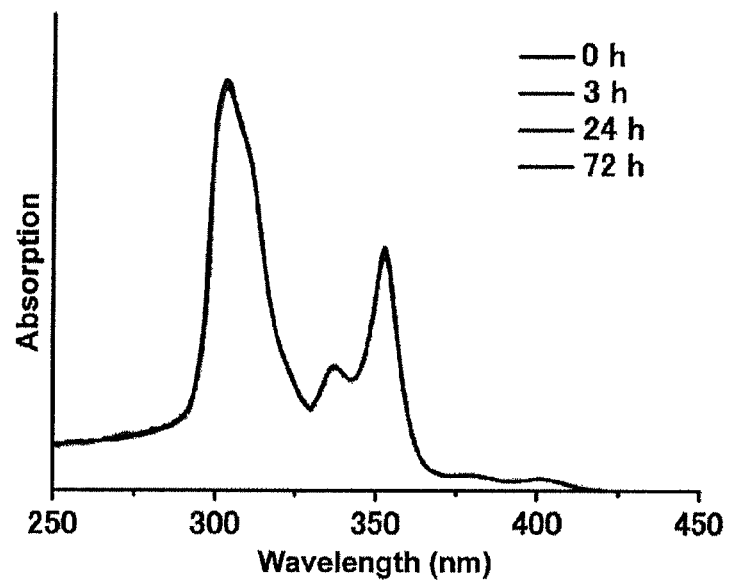
FIG. 5 shows a UV-Vis absorption spectrum of a synthesis compound (solution).

Then, 0.6951 mg of the compound synthesized in Example 3 was weighed, and dissolved into degassed benzonitrile (25 mL) using a measuring flask in a glove box (solution concentration: 4.92×10$^{-5}$ M). A prepared solution thereof was put into a UV cell with a cover, and a UV-Vis spectrum (device used: Jasco V-570 Spectrometer, made by JASCO Corporation) was immediately measured. Subsequently, opening and closing of the cover were repeated several times under atmospheric air to bring the solution into contact with oxygen in air. Then, the results measured in a similar manner after 3 hours, 24 hours and 72 hours are shown in FIG. 5. As a result, no change of the spectrum was observed in the solution that was allowed to stand for 72 hours.

Figure 6:
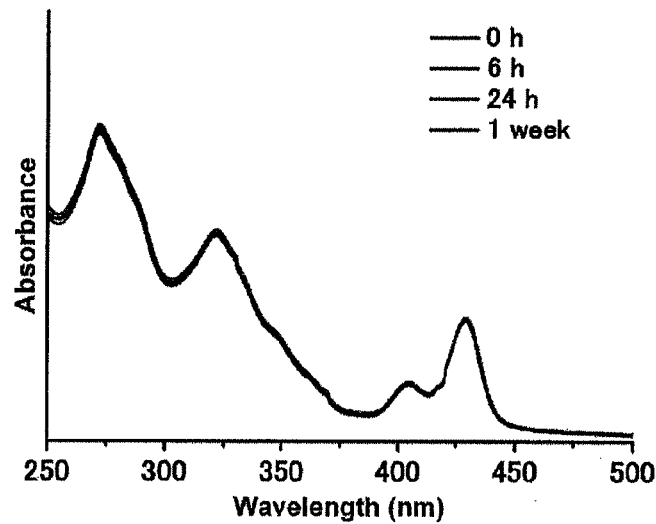
FIG. 6 shows a UV-Vis absorption spectrum of a synthesis compound (film).

Moreover, a film having a thickness of 100 nanometers formed by performing vacuum deposition of the compound synthesized in Example 3 was allowed to stand for one week in atmospheric air. The results obtained by measuring UV-Vis spectra (device used: Jasco V-570 Spectrometer, made by JASCO Corporation) over time during the period are shown in FIG. 6. As a result, no change of the spectrum was observed even in the film allowed to stand for one week.

As described above, the compound synthesized in Example 3 is clearly found to be chemically stable.

Figure 2:
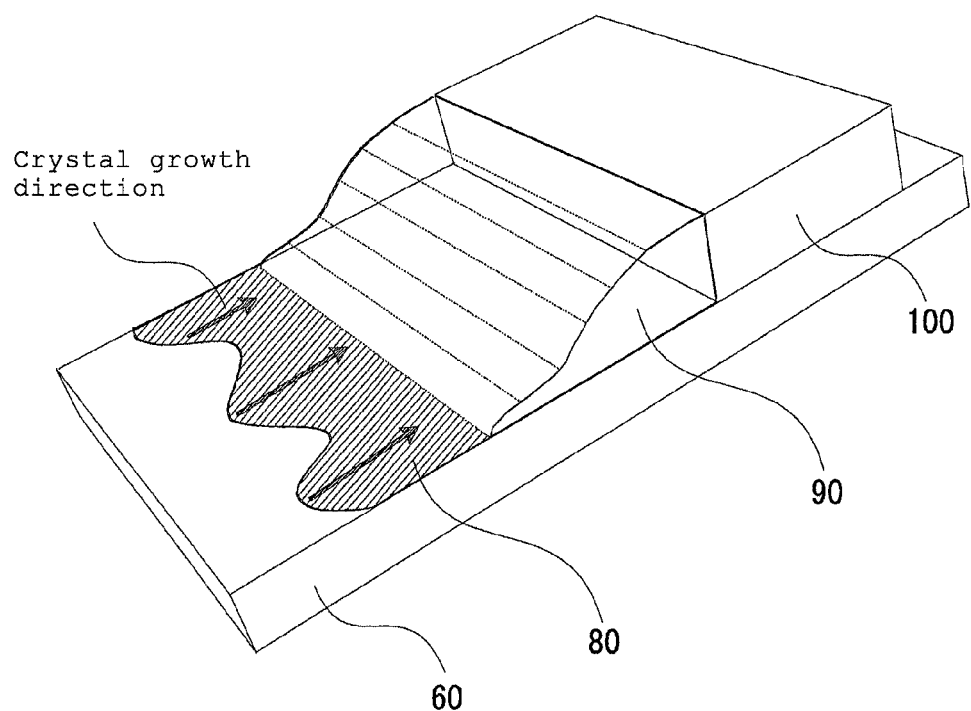
FIG. 2 is a drawing showing an outline of film formation by an edge-cast process.

Preparation of Organic Transistor Device and Evaluation of Characteristics Thereof Edge-Cast Process In accordance with an application process (edge-cast process; Appl. Phys. Exp. 2, 111501 (2009)) developed by the present inventors, film formation and preparation of a bottom gate-top contact type organic FET were performed. A conceptual diagram of the process is shown in FIG. 2.

Surface treatment was applied to a silicon substrate (made by Fujimi Fine Technology Inc.) by decyltriethoxysilane (DTS) to obtain a silicon substrate (hereinafter, also referred to as "substrate") with a thermally oxidized silicon insulating film (film thickness: 500 nm). On the substrate, a solution-holding silicon substrate fragment (hereinafter, also referred to as "solution holding structure") was placed. While inclining the substrate, an o-xylene solution of a chalcogen-containing organic compound synthesized in Examples or a 1,2-dichloroethane solution thereof (concentration of chalcogen-containing organic compound: 0.2% by mass) (organic semiconductor solution) was dripped at 120° C. onto an edge of the solution holding structure. While a crystal grew with evaporation of the solvent, the crystal stuck to the substrate, and crystal growth was completed in several minutes. In the state, the grown crystal was allowed to stand overnight (11 hours) under argon atmosphere at 60 to 100° C. to completely dry a crystal film (film thickness: 30 to 150 nm). On the crystal film obtained, a carrier injection layer (film thickness: 1 nm) of tetrafluorotetracyanoquinodimethane was formed through a stainless-steel metallic mask, and subsequently a gold source electrode and a gold drain electrode (film thickness: 30 nm) were vapor-deposited to form a channel length of 100 μm and a channel width of 1 mm and to prepare a bottom gate-top contact type organic FET. Carrier mobility and an ON-OFF ratio were measured on the thus prepared device using Semiconductor Parameter Analyzer (model number "Keithley 4200," made by Keithley Instruments Inc.).

Gap-Cast Process

Figure 3:
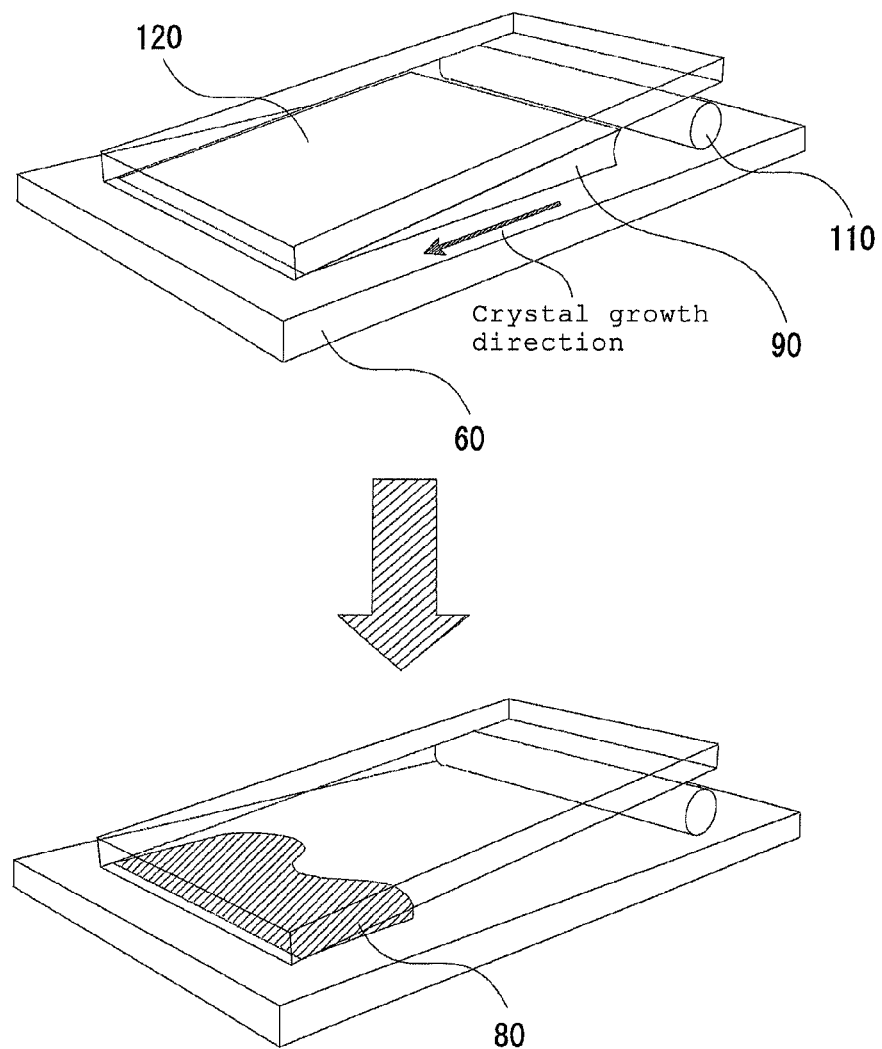
FIG. 3 is a drawing showing an outline of film formation by a gap-cast process.

In accordance with the application process (gap-cast process; Adv. Mater. 23, 1626 (2011).) developed by the present inventors, film formation and preparation of device of a bottom gate-top contact type organic FET were performed. A conceptual diagram of the process is shown in FIG. 3.

On the substrate subjected to surface treatment as used in the edge-cast process described above, a spacer was placed, and thereon, a silicon substrate subjected to surface treatment with F-SAM was stacked on the substrate as a solution holding plate to form a wedge-shaped interstice. The resulting structure was heated at 120° C. on a hot plate, and after temperature was stabilized, an o-dichlorobenzene solution of a chalcogen-containing organic compound synthesized in Examples (concentration of chalcogen-containing organic compound: 0.2% by mass) (organic semiconductor solution) was injected into the wedge-shaped interstice. The solution was held in the wedge-shaped interstice and a crystal grew with evaporation of the solvent. After evaporation of the solvent, in the state, the grown crystal was allowed to stand overnight (11 hours) under argon atmosphere at 60 to 100° C. to completely dry a crystal film (film thickness: 150 to 250 nm). Then, a device was prepared in a manner similar to the operations in the edge-cast process described above, and characteristics of FET were evaluated.

Preparation of the organic transistor device and evaluation of characteristics thereof as described above were performed on the compound obtained in Examples. The results of evaluation are shown in Table 1. Moreover, FET characteristics of the compound synthesized in Example 7 are shown in FIG. 4. According to FIG. 4, the compound synthesized in Example 7 was confirmed to show carrier mobility as high as 10 to 11 cm$^2$/vs.

On the other hand, in the compound in Comparative Example 1, preparation of a two-dimensional crystal film with high quality was not allowed according to the solution process, and film formation by the application process was difficult. As a result, with regard to the compound in Comparative Example 1, preparation of the organic transistor device by the application process and evaluation of the characteristics thereof were not allowed.

Table 1

TABLE 1

| | Organic semiconductor material | Carrier mobility (cm$^2$/V·s) | ON-OFF ratio | Film-forming method |
|---|---|---|---|---|
| Example 1 | $C_{10}H_{21}$—[structure]—$C_{10}H_{21}$ with O | 1.3 | $10^6$ | Edge cast |
| Example 2 | $C_{10}H_{21}$—[structure]—$C_{10}H_{21}$ with S | 1.0 | $10^5$ | Edge cast |
| Example 3 | $C_{10}H_{21}$—[structure]—$C_{10}H_{21}$ with O | 2.0 | $10^5$ | Edge cast |
| Example 6 | $C_{10}H_{21}$—[structure]—$C_{10}H_{21}$ with S | 6.5 | $10^7$ | Gap cast |

TABLE 1-continued

| | Organic semiconductor material | Carrier mobility (cm²/V · s) | ON-OFF ratio | Film-forming method |
|---|---|---|---|---|
| Example 7 | C$_6$H$_{13}$—[structure]—C$_6$H$_{13}$ | 11.0 | $10^7$ | Edge cast |
| Example 8 | C$_8$H$_{17}$—[structure]—C$_8$H$_{17}$ | 4.5 | $10^7$ | Gap cast |
| Example 9 | C$_4$H$_9$—[structure]—C$_4$H$_9$ | 6.0 | $10^6$ | Edge cast |
| Comparative Example 1 | [structure] | — | — | Edge cast |

Comparison of FET Characteristics by Vapor Deposition Process

Device preparation by the application process was not allowed with regard to the chalcogen-containing organic compound in Comparative Example 1. Therefore, a device was prepared by the vapor deposition process for the chalcogen-containing organic compounds in Example 6 and Comparative Example 1, and FET characteristics were compared.

Ultrasonic cleaning was applied to a silicon substrate with the thermally oxidized silicon insulating film (film thickness: 500 nm) described above for 5 minutes using acetone and 2-propanol for each, and subsequently UV ozone treatment was applied for 30 minutes. On a surface of the substrate subjected to cleaning treatment, a self-assembled monolayer of DTS was formed according to a vapor process, and then a chalcogen-containing organic compound was vapor-deposited at a vapor deposition rate of 0.4 to 0.6 Å/s to form an organic semiconductor layer having a film thickness of 75 nm. Subsequently, a carrier injection layer (film thickness: 1 nm) of tetrafluorotetracyanoquinodimethane was formed through a stainless-steel metallic mask, and subsequently a gold source electrode and a gold drain electrode (film thickness: 30 nm) were vapor-deposited to form a channel length of 100 μm and a channel width of 1 mm and to prepare a bottom gate-top contact type organic FET.

Carrier mobility and an ON-OFF ratio were measured on the thus prepared device using Semiconductor Parameter Analyzer (model number "Keithley 4200", made by Keithley Instruments Inc.). As a result, when the organic semiconductor material in Example 6 was used for formation of the organic semiconductor layer, carrier mobility was 5.5 cm²/V·s and the ON-OFF ratio was $10^7$. On the other hand, when the organic semiconductor material in Comparative Example 1 was used for formation of the organic semiconductor layer, carrier mobility was 0.4 cm²/V·s and the ON-OFF ratio was $10^6$.

From the results described above, the organic semiconductor material synthesized in each Example is clearly found: (1) to be further excellent in solubility in any solvent, and (2) to show substantially higher carrier mobility without depending on the film-forming method in comparison with the organic semiconductor material synthesized in Comparative Example.

REFERENCE SIGNS LIST

10 Source electrode
20 Drain electrode
30 Gate electrode
40 Organic semiconductor layer
50 Gate insulating film
60 Substrate
70 Carrier injection layer
80 Crystal film
90 Organic semiconductor solution
100 Solution holding structure
110 Spacer
120 Solution holding plate

What is claimed is:
1. A compound of formula (1-1) or formula (1-2):

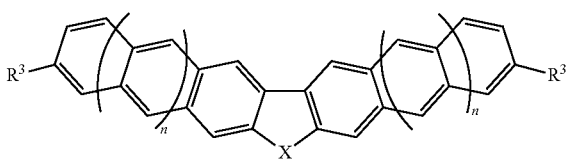

(1-1)

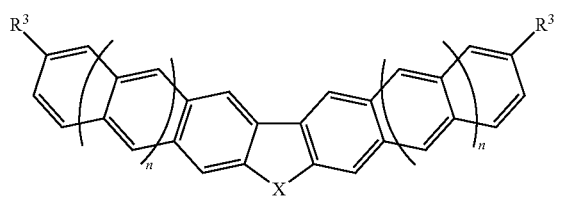

(1-2)

wherein, in formula (1-1) and formula (1-2),
X is oxygen, sulfur or selenium;
each n is independently 0 or 1;
each $R^3$ is independently fluorine, alkyl having 1 to 20 carbons, aryl, pyridyl, furyl, thienyl or thiazolyl, optionally one or more hydrogens in the alkyl is replaced by fluorine, and optionally one or more hydrogens on a ring of the aryl, the pyridyl, the furyl, the thienyl and the thiazolyl is replaced by at least one selected from the group consisting of halogen and alkyl having 1 to 10 carbons.

2. The compound according to claim 1, wherein $R^3$ in formula (1-1) and formula (1-2) is an identical group selected from the group consisting of alkyl having 4 to 15 carbons, phenyl, furyl and thienyl.

3. A method for manufacturing the compound according to claim 1, wherein, X is sulfur or selenium, comprising: a step for allowing coupling of compounds of formula (11) to obtain a compound of formula (12); a step for allowing deprotection of methoxy of the compound of formula (12) to obtain a compound of formula (13); a step for allowing the compound of formula (13) to react with N,N-dialkyl thiocarbamoyl chloride or N,N-dialkyl selenocarbamoyl chloride to obtain a compound of formula (14); and a step for heating the compound of formula (14) to obtain a compound of formula (15):

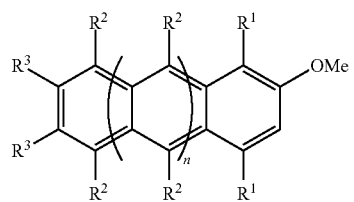

(11)

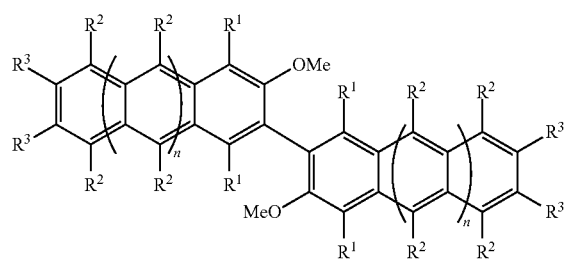

(12)

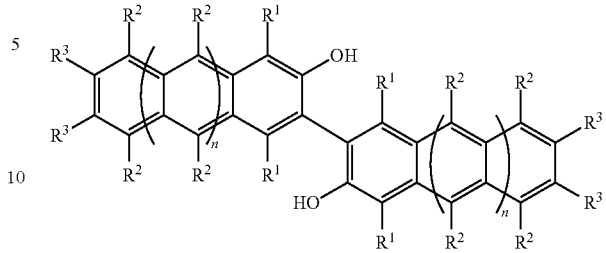

(13)

(14)

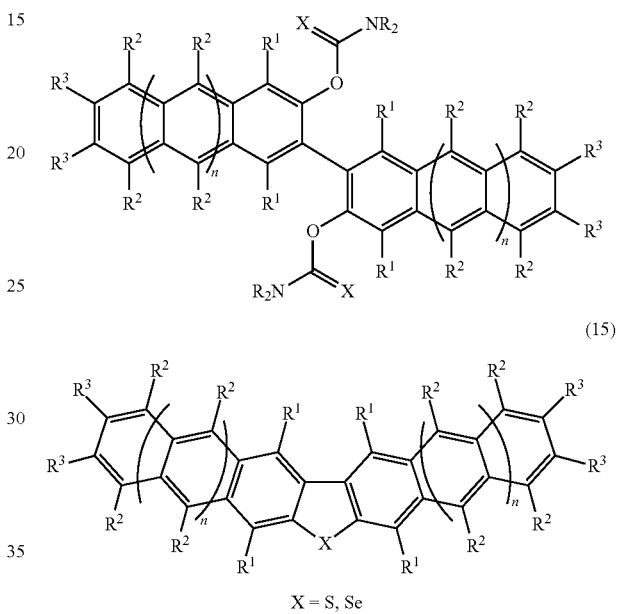

(15)

X = S, Se wherein, in formulas (11) to (15), X is sulfur or selenium, n and $R^1$ to $R^3$ each are defined in a manner identical with the definitions of an identical symbol in formula (1), Me is methyl, and in formula (14), R's are each independently alkyl having 1 to 3 carbons.

4. A method for manufacturing the compound according to claim 1, wherein, X is selenium, comprising: a step for allowing coupling of compounds of formula (11) to obtain a compound of formula (12); a step for allowing deprotection of methoxy of the compound of formula (12) to obtain a compound of formula (13); a step for allowing the compound of formula (13) to react with trifluoromethanesulfonyl chloride or trifluoromethanesulfonic anhydride to obtain a compound of formula (16); a step for allowing coupling of the compounds of formula (16) with boranes to obtain boronic ester of formula (17); a step for brominating the boronic ester of formula (17) with copper bromide to obtain a compound of formula (18); and a step for lithiating the compound of formula (18), and then allowing the resulting product to react with selenium chloride to obtain a compound of formula (15):

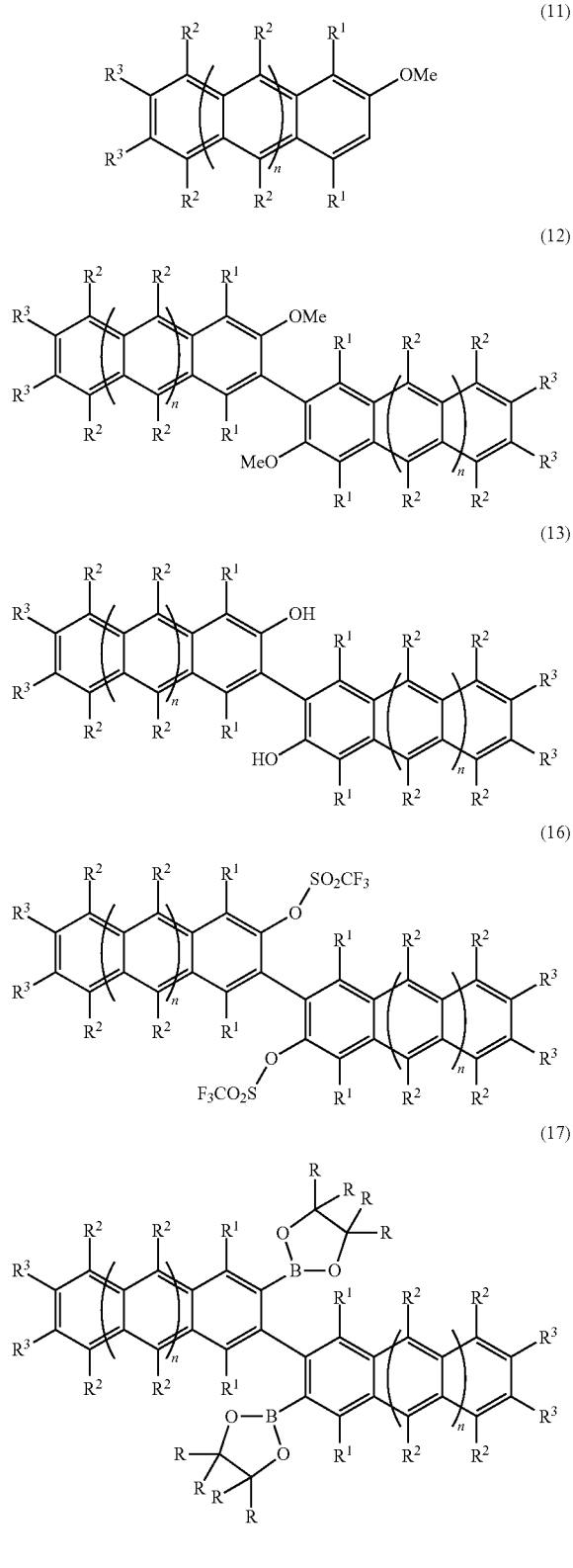

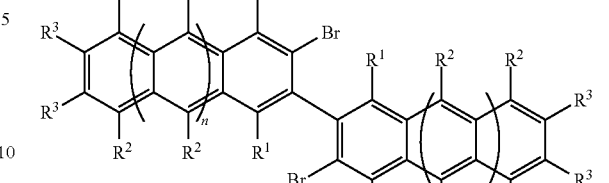

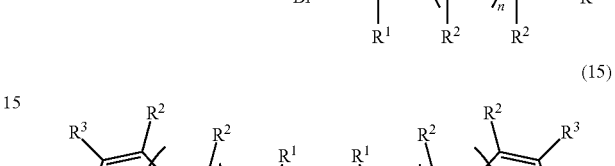

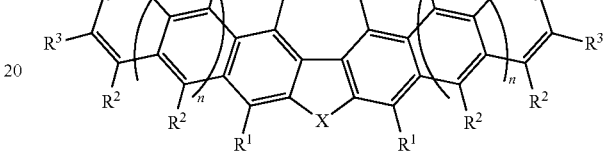

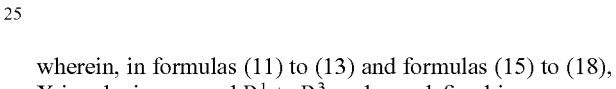

X = Se wherein, in formulas (11) to (13) and formulas (15) to (18), X is selenium, n and $R^1$ to $R^3$ each are defined in a manner identical with the definitions of an identical symbol in formula (1), Me is methyl, and in formula (17), R's are each independently alkyl having 1 to 3 carbons.

5. A method for manufacturing the compound according to claim 1, wherein, X is oxygen, comprising: a step for allowing coupling of compounds of formula (11) to obtain a compound of formula (12); a step for allowing deprotection of methoxy of the compound of formula (12) to obtain a compound of formula (13); a step for heating and dehydrating the compound of formula (13) under a zeolite catalyst to obtain a compound of formula (15):

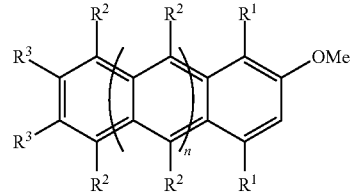

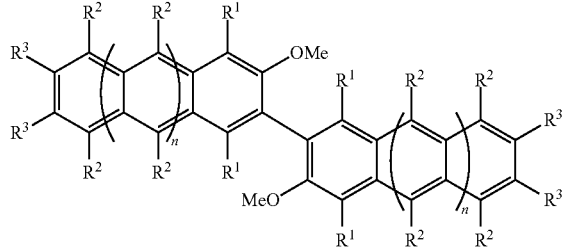

-continued

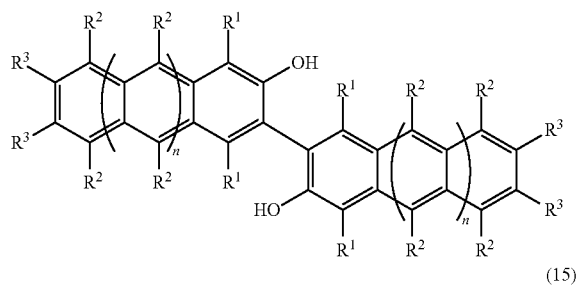

(13)

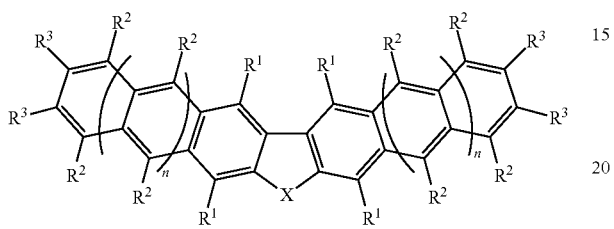

(15)

X = O wherein, in formulas (11) to (13) and (15), X is oxygen, n and $R^1$ to $R^3$ each are defined in a manner identical with the definitions of an identical symbol in formula (1), and Me is methyl.

6. An organic semiconductor material, composed of the compound according to claim 1.

7. An organic semiconductor film, including the organic semiconductor material according to claim 6.

8. An organic field effect transistor comprising a substrate, a gate electrode, a gate insulating film, a source electrode, a drain electrode and an organic semiconductor layer, wherein the organic semiconductor layer is constituted of the organic semiconductor film according to claim 7.

* * * * *